United States Patent
Mahajan

(12) 
(10) Patent No.: US 6,538,176 B1
(45) Date of Patent: Mar. 25, 2003

(54) MAIZE REPLICATION PROTEIN A AND USE

(75) Inventor: Pramod B. Mahajan, Urbandale, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/396,149

(22) Filed: Sep. 15, 1999

Related U.S. Application Data

(60) Provisional application No. 60/123,896, filed on Mar. 11, 1999, and provisional application No. 60/100,690, filed on Sep. 17, 1998.

(51) Int. Cl.⁷ .......................... A01H 5/00; C07H 21/04; C12N 15/00

(52) U.S. Cl. ........................ 800/278; 435/6; 435/320.1; 536/23.1; 536/23.6; 536/24.5; 536/24.3; 800/295; 800/300.1; 800/301

(58) Field of Search .................. 435/6, 320.1; 536/23.1, 536/23.6, 24.5, 24.3; 800/295, 300.1, 301

(56) References Cited

FOREIGN PATENT DOCUMENTS

WO    WO 97/08331    3/1997

OTHER PUBLICATIONS

Van Der Knaap et al, Expression of an Ortholog of Replication Protein A1 (RPA1) is Induced by Gibberellin in Deepwater Rice, Sep. 199, Plant Biology, vol. 94, pp. 9979–9983.*

Van Der Knap E., et al., Expression of an Ortholog of Replication Protein A1 (RPA1) is Induced by Gibberellin in Deepwater Rice, Proc. Natl. Acad. Sci., 1997, vol. 94, pp. 9979–9983.

Van Der Knap, et al., Oryza Sativa Replication Protein A1 (Os–RPA1) mRNA, complete cds, EMBL Accession No.: AF009179, Jul. 18, 1997.

Shen, et al., DBEST ID: 52849, Jul. 18, 1994, EMBL Accession No.: T23395, Jul. 21, 1994.

Churin et al., Hordeum Vulgare cv. Haisa mRNA for cp31BHv Protein, EMBL Accession No.: AJ224324, Sep. 4, 1998.

Shen et al., 5C04G01–T7 Membrane–Free Polysomes form Endosperm Zea Mays cDNA Clone 5C04G01 5' End Similar to 60s Ribosomal Protein L19 EMBL Accession No. T18701, May 14, 1994.

Ishiai M., et al., Purification, Gene Cloning, and Reconstitution of the Heterotrimeric Single–Stranded DNA–Binding Protein from Schizosaccharomyces Pombe, The Journal of Biological Chemistry, 1996, vol. 271, No. 34, pp. 20868–20878.

Ishiai M., et al., Replication Factor–A Protein 2 (Single–Stranded DNA–Binding Protein P30 Subunit), Swissprot Accession No. Q92373, Nov. 1, 1997.

Nakamura et al., *Arabidopsis Thaliana*Genomic DNA, Chromosome 5, P1 Clone: MNL12 EMBL Accession No. AB011070, Sep. 3, 1998.

Wilson R., et al., Caenorhabditis Elegans Cosmid K12C11., EMBL Accession No. AFO 43701, Jan. 23, 1998.

Walbot V., DBEST ID:2980430, Jul. 22, 1999, EMBL Accession No. AI881882, Jul. 23,1999.

Walbot V., DBEST ID: 2943612, Jul. 15, 1999, EMBL Accession No. A1855065, Jul. 22,1999.

Walbot V., et al. DBEST ID: 2970064, Jul. 21, 1999, EMBL Accession No. AI881517, Jul. 22, 1999.

Walbot V., DBEST ID: 2922893, Jul. 14, 1999. EMBL Accession No. AI834577, Jul. 16, 1999.

Walbot V., et al., 60508D02 .x2 606—Ear Tissue cDNA Library from Schmidt Lab Zea Mays cDNA, mRNA Sequence, EMBL Accession No. AI770788, Jun. 30, 1999.

Walbot, 618009B07 .x1 618—Inbred Tassel cDNA Library Zea Mays cDNA, mRNA Sequence, EMBL Accession No. AI901688, Jul. 28, 1999.

Walbot V., 605089A07 .x1 605—Endosperm cDNA Library from Schmidt Lab Zea Mays cDNA, mRNA Sequence, Jul. 14, 1999.

Walbot V., et al., 487012G02 .x1 487—Apical Meristem cDNA Library from Hake lab Zea Mays cDNA, mRNA Sequence, EMBL Accession No. AI396192, Feb. 5, 1999.

LIN X., et al.,*Arabidopsis Thaliana* Chromosome II Section 137 of 255 of the Complete Sequence, EMBL Accession No. Ac006403, Jan. 18, 1999.

Braun et al. (1997), "Role of Protein—Protein Interactions in the function of Replication Protein A (RPA): RPA Modulates the Activity of DNA Polymerase α by Multiple Mechanisms," *American Chemical Society* 36 (28):8443–8454, Department of Biochemistry, University of Iowa College of Medicine.

Bochkareva et al. (1998), "The RPA32 Subuit of Human Replication Protein A Contains a Single–stranded DNA–binding Domain," *The Journal of Biological Chemistry* 273 (7):3932–3936, Ontario Cancer Institute, University of Toronto.

Longhese et al. (1994), "Replication Factor A is Required In Vivo for DNA Replication, Repair, and Recombination," *American Society for Microbiology* 14 (12 ):7884–7890.

Loor et al. (1997), "Identification of DNA Replication and Cell Cycle Proteins that Interact with PCNA," *Nucleic Acids Research* 25 (24):5041–5046, Department of Biochemistry and Molecular Biology and Medicine, University of Miami.

(List continued on next page.)

*Primary Examiner*—Sean McGarry
(74) *Attorney, Agent, or Firm*—Alston & Bird LLP

(57) ABSTRACT

Methods and compositions for modulating DNA metabolism are provided. Nucleotide and amino acid sequences encoding a maize replication protein A subunits are provided. The sequences can be used in expression cassettes for modulating DNA replication, DNA repair, and recombination.

26 Claims, 4 Drawing Sheets

OTHER PUBLICATIONS

New et al. (1998), "Rad52 Protein Stimulates DNA Strand Exchange by Rad51 and Replication Protein A," *Nature 391* (*22*):407–410, University of California at Davis.

NIU et al. (1997),"Mapping of Amino Acid Residues in the p34 Subunit of Human Single–stranded DNA–binding Protein Phosphorylated by DNA–dependant Protein Kinase and Cdac2 Kinase in Vitro," *The Journal of Biological Chemistry 272* (*19* ): 12634–12641.

Sibenaller et al. (1998), "The 32– and 14–Kilodalton Subunits of Replication Protein A Are Responsible for Species–Specific Interactions with Single–Stranded DNA," *Biochemistry 37*:12496–12506, Department of Biochemistry, University of Iowa College of Medicine.

Wold, M. (1997), "Replication Protein A: A Heterotrimeric, Single–Stranded DNA–Binding Protein Required for Eukaryotic DNA Metabolism," *Annu. Rev. Biochem. 66*:61–92,Department of Biochemistry, University of Iowa College of Medicine.

* cited by examiner

```
                 1                                                              50
ZMRPALSH1   ~~MDAAKSVT  PGAVSYIL..  AHPSTGSDGA  VSDLVVQVLD  LKSIGMGS.R
ZMRPALSH2   ~~MDAAKLVT  PVAVSHIL..  AHPSAGSDGA  VTDLVVQVLD  LKSVGTGS.R
   024183   MDSDAAPSVT  PGAVAFVLEN  ASPDAATGVP  VPEIVLQVVD  LKPIGT...R
Rfal_Xenla  ~~~MALPQLS  EGAISA-MLG  GDSSC..KPT  LQVINIRPIN  ...TGNGPPR
Rfal_Human  ~~~~MVGQLS  EGAIAAIMQK  GDTNI..KPI  LQVINIRPIT  ...TGNSPPR
Rfal_Drome  ~~~MVLASLS  TGVIARIM.H  GEVVD..APV  LQILAIKKIN  ...SAADSER
Rfal_Schpo  ~~~~MAERLS  VGALRIINTS  DASSFPPNPI  LQVLTVKELN  SNPTSGAPKR
Rfal_Yeast  ~~~MSSVQLS  RGDFHSIFTN  KQR..YDNPT  GGVYQVYNTR  KSDGANSNRK 51                                                             100
ZMRPALSH1   FSFTASDGND  KIKA.MLPTY  FASEVHSGNL  KNFGLIRILD  YTCNSVK..G
ZMRPALSH2   FSFTATDGKD  KIKA.MLPTN  FGSEVRSGNL  KNLGLIRIID  YTCNVVK..G
   024183   FTFLASDGKD  KIKT.MLLTQ  LAPEVRSGNI  QNLGVIRVLD  YTCNTIG..E
Rfal_Xenla  YRLLMSDGLN  TLSSFMLATQ  LNSLVDNNLL  ATNCICQVSR  FIVNNL.KD.
Rfal_Human  YRLLMSDGLN  TLSSFMLATQ  LNPLVEEEQL  SSNCVCQIHR  FIVNTL.KD.
Rfal_Drome  YRILISDGKY  FNSYAMLASQ  LNVMQHNGEL  EEFTIVQLDK  YVTSLVGKDG
Rfal_Schpo  YRVVLSDSIN  YAQS.MLSTQ  LNHLVAENKL  QKGAGVQLTQ  FTVNVMKE..
Rfal_Yeast  NLIMISDGIY  HMKA.LLRNQ  AASKFQSMEL  QRGDIIRV..  IIAEPAIVRE 101                                                            150
ZMRPALSH1   NADKVLIVVK  CETVCEA..L  DAEINGEAKK  ED..PPIVLK  PKDEGSVVAE
ZMRPALSH2   KDDKVLVVIK  CELVCQA..L  DAEINGEAKK  EE..PPIVLK  PKDECVGV..
   024183   KQEKVLIITK  LEVVFKA..L  DSEIKCEAEK  QEEKPAILLS  PKEESVVLSK
Rfal_Xenla  .GRRVIIVME  LDVLKSADLV  MGKIGNPQPY  ND..GQPQPA  APAPASAPA.
Rfal_Human  .GRRVVILME  LEVLKSAEAV  GVKIGNPVPY  NEGLGQPQVA  PPAPAASPAA
Rfal_Drome  AGKRVLIISE  LTVVNPGAEV  KSKIGEPVTY  ENAAKQDLAP  KPAVTSNSKP
Rfal_Schpo  ..RKILIVLG  LNVLTELG.V  MDKIGNPAGL  ETVDALRQQQ  NEQNNASAPR
Rfal_Yeast  RKKYVLLVDD  FELVQSRADM  VNQTSTFLDN  YFSEHPNETL  KDEDITDSGN 151                                                            200
ZMRPALSH1   ETNSPP..L.  ..VMKPKQEV  KSASQIVTEQ  RGNAAPATRL  SMTRRVHPLI
ZMRPALSH2   ...TSP..L.  ..VMKPKQEV  KSASQIVTEQ  RGNAAPATRL  SMTRRVHPLI
   024183   PTNAPP..LP  PVVLKPKQEV  KSASQIVNEQ  RGNAAPAARL  AMTRRVHPLI
Rfal_Xenla  ...PAPSKLQ  NNSAPPPSMN  RGTSKLFG..  .GGSLLNTPG  GSQSKVVPIA
Rfal_Human  SSRPQPQNGS  SGMGSTVSKA  YGASKTFGKA  AGPSLSHTSG  GTQSKVVPIA
Rfal_Drome  IAKKEPSHNN  NN........  ..........  ...NIVMNSS  INSGMTHPIS
Rfal_Schpo  TGISTSTNSF  YGNNAAATAP  APPPMMKKPA  APNSL.....  ..STIIYPIE
Rfal_Yeast  VA....NQTN  ASNAGVPDML  HSNSNLNANE  RKFANENPNS  QKTRPIFAIE 201                                                            250
ZMRPALSH1   TLNPYQGNWV  IKVRVTSKGN  LRTYRNARGE  GCVFNVELTD  EDGTQIQATM
ZMRPALSH2   TLNPYQGNWV  IKVRVTSKGN  LRTYRNARGE  GCVFNVELTD  EDGTQIQATM
   024183   SLNPYQGNWI  IKVRVTSKGN  LRTYKNARGE  GCVFNVELTD  VDGTQIQATM
Rfal_Xenla  SLNPYQSKWT  VRARVTNKGQ  IRTWSNSRGE  GKLFSIEMVD  ESG EIRATA
Rfal_Human  SLTPYQSKWT  ICARVTNKSQ  IRTWSNSRGE  GKLFSLELVD  ESG EIRATA
Rfal_Drome  SLSPYQNKWV  IKARVTSKSG  IRTWSNARGE  GKLFSMDLMD  ESG EIRATA
Rfal_Schpo  GLSPYQNKWT  IRARVTNKSE  VKHWHNQRGE  GKLFSVNLLD  ESG EIRATG
Rfal_Yeast  QLSPYQNVWT  IKARVSYKGE  IKTWHNQRGD  GKLFNVNFLD  TSG EIRATA
```

TO FIG. 1B.

Comparison of eukaryotic RPA LS amino acid sequences

FIG. 1A.

FROM FIG. 1A.

```
            251                                                              300
ZMRPALSH1   FNEAAKKFYP  IFELGKVYYV  SKGSLRIANK  QFKTVKNDYE  LSLNENAIVE
ZMRPALSH2   FNDAAKKFYP  IFELGKVYYV  SKGSLRIANK  QFKTVQNDYE  MSLNENAIVE
   024183   FNEAAKKFYP  MFELGKVYYI  SKGSLRVANK  QFKTVHNDYE  MTLNENAVVE
Rfal_Xenla  FNEQADKFFS  IIEVNKVYYF  SKGTLKIANK  QYTSVKNDYE  MTFNSETSVI
Rfal_Human  FNEQVDKFFP  LIEVNKVYYF  SKGTLKIANK  QFTAVKNDYE  MTFNNETSVM
Rfal_Drome  FKEQCDKFYD  LIQVDSVYYI  SKCQLKPANK  QYSSLNNAYE  MTFSGETVVQ
Rfal_Schpo  FNDQVDAFYD  ILQEGSVYYI  SRCRVNIAKK  QYTNVQNEYE  LMFERDTEIR
Rfal_Yeast  FNDFATKFNE  ILQEGKVYYV  SKAKLQPAKP  QFTNLTHPYE  LNLDRDTVIE
            301                                                              350
ZMRPALSH1   EAE..GETFL  PPVQYNLVKI  DQLGPYVGGR  ELVDIVGVVQ  SVSPTLSVRR
ZMRPALSH2   EAE..GETCI  PQVQYNLVKI  DQLGSYVGGR  ELVDIVGVVQ  SVSPTLSVRR
   024183   EAE..GETFI  PQIQYNFVKI  DQLGPYVGGR  ELVDVIGVVQ  SVSPTLSVRR
Rfal_Xenla  PCDDSAD..V  PMVQFEFVSI  GELES.KNKD  TVLDIIGVCK  NVEEVTKVTI
Rfal_Human  PCEDDH..L   PTVQFDFTGI  DDLEN.KSKD  SLVDIIGICK  SYEDATKITV
Rfal_Drome  LCEDTDDDPI  PEIKYNLVPI  SDVSG.MENK  AAVDTIGICK  EVGELQSFVA
Rfal_Schpo  KAED..QTAV  PVAKFSFVSL  QEVGD.VAKD  AVIDVIGVLQ  NVGPVQQITS
Rfal_Yeast  ECFDESN..V  PKTHFNFIKL  DAIQN.QEVN  SNVDVLGIIQ  TINPHFELTS
            351                                                              400
ZMRPALSH1   KIDNETIPKR  DIVVADDSGK  TVTISLWNDL  ATTTGQELLD  MVDSSPVVAI
ZMRPALSH2   KIDNETIPKR  DIVVADDSGK  TVSISLVNDL  ATTTGQELLD  MADSSPVVAI
   024183   KIDNETIPKR  DIVVADDSSK  TVTISLWNDL  ATTTGQELLD  MVDSAPIIAI
Rfal_Xenla  KSNNREVSKR  SIHLMDSSGK  VVSTTLWGED  ADKFD.....  .GSRDPVVAI
Rfal_Human  RSNNREVAKR  NIYLMDTSGK  VVTATLWGED  ADKFD.....  .GSRQPVLAI
Rfal_Drome  RTTNKEFKKR  DITLVDMSNS  AISLTLWGDD  AVNFD.....  .GHVQPVILV
Rfal_Schpo  RATSRGFDKR  DITIVDQTGY  EMRVTLWGKT  AIEFS.....  .VSEESILAF
Rfal_Yeast  RA.GKKFDRR  DITIVDDSGF  SISVGLWNQQ  ALDFN.....  .LPEGSVAAI
            401                                                              450
ZMRPALSH1   KSLKVSDFQ.  GVSLSTIGRS  TLEINPDLPE  AKNLKSWYDS  EGKDTSLAPI
ZMRPALSH2   KSLKVSDFQ.  GVSLSTVGKS  TLAINPDLHE  AQNLKSWYDS  EGKDTSLAPI
   024183   KSLKVSDFQ.  GLSLSTVGRS  TIVVNPDLPE  AEQLRAWYDS  EGKGTSMASI
Rfal_Xenla  KGARLSDF.G  GRSLSVLSSS  TVMINPDIPE  AFKLRAWFDS  EGQVVEGTSI
Rfal_Human  KGARVSDF.G  GRSLSVLESSS TIIANPDIPE  AYKLRGWFDA  EGQALDGVSI
Rfal_Drome  KGTRINEFNG  GKSLSLGGGS  IMKINPDIPE  AHKLRGWFDN  GGGDSVANMV
Rfal_Schpo  KGVKVNDFQ.  GRSLSMLTSS  TMSVDPDIQE  SHLLDGWYDG  QGRGQEFAKH
Rfal_Yeast  KGVRVTDF.G  GKSLSMGFSS  TLIPNPEIPE  AYALKGWYDS  KGRNANFITL
            451                                                              500
ZMRPALSH1   SAEAGATRAG  G..FKSMYSD  RVFLSHITSD  PAMGQEKPVF  FSLYAIISHI
ZMRPALSH2   GAEMGAARAG  G..FKSTYSD  RVFLSHITSD  PAMGQEKPVF  FSLYATISHI
   024183   GSDMGASRVG  G..ARSMYSD  RVFLSHITSD  PNLGQDKPVF  FSLNAYISLI
Rfal_Xenla  SESRGG.GTG  GGN.....TN  WKSLLEVKNE  NLGHGEKADY  FTSVATIVYL
Rfal_Human  SDLKSG.GVG  GSN.....TN  WKTLYEVKSE  NLGQGDKPDY  FSSVATVVYL
Rfal_Drome  SARTGG...G  SFS.....TE  WMTLKDARAR  NLGSGDKPDY  FQCKAVVHIV
Rfal_Schpo  SVISSTLSTT  GRS.....AE  RKNIAEVQAE  HLGMSETPDY  FSLKGTIVYI
Rfal_Yeast  KQEPGMGGQS  AASLTKFIAQ  RITIARAQAE  NLGRSEKGDF  FSVKAAISFL
```

TO FIG. 1C.

Comparison of eukaryotic RPA LS amino acid sequences

FIG. 1B.

FROM FIG. 1B.

```
              501                                                                    550
ZMRPALSH1    KPDQNMWYRA  CTT..CNKKV  TEAFGSGYWC  ECCQKNDSEC  SLRYIMVIKL
ZMRPALSH2    KPDQNMWYRA  CKT..CNKKV  TETFGSGYWC  ECCQKNDSEC  SLRYIMVIKV
    024183   KPDQTMWYRA  CKT..CNKKV  TEAMGSGYWC  ECCQKNDAEC  SLRYIMVIKV
Rfal_Xenla   RKE.NCLYQA  CPSQDCNKKV  IDQQNGLFRC  EKCNKEFPNF  KYRLILSANI
Rfal_Human   REK.NCMYQA  CPTQDCNKKV  IDQQNGLYRC  EKCDTEFPNF  KYRMILSVNI
Rfal_Drome   KQE.NAFYRA  CPQSDCNKKV  VDECNDQFRC  EKCNALFPNF  KYRLLINMSI
Rfal_Schpo   RKK.NVSYPA  CPAADCNKKV  FDQG.GSWRC  EKCNKEYDAP  QYRYIITIAV
Rfal_Yeast   KVD.NFAYPA  CSNEMCNKKV  LEQPDCTWRC  EKCDTNNARP  NWRYILTISI 551                                                                    600
ZMRPALSH1    SDPTGEAWVS  VFNEHAEKII  GCSADELDRI  RKEEGDDSYV  LKLKEATWVP
ZMRPALSH2    SDPTGEAWFS  VFNEHAEKII  GCSADELDRI  RKEEGDDSYV  LKLKEATWVP
    024183   SDPTGEAWLS  LFNDQAERIV  GCSADELDRI  RKEEGDDSYL  LKLKEATWVP
Rfal_Xenla   ADFGENQWIT  CFQESAISIL  GQNATYLGEL  .KEKNEQAYD  EVFQNANFRS
Rfal_Human   ADFQENQWVT  CFQESAEAIL  GQNAAYLGEL  .KDKNEQAFE  EVFQNANFRS
Rfal_Drome   GDWTSNRWVS  SFNEVGEQLL  GHTSQEVGEA  .LENDPAKAE  QIFSALNFTS
Rfal_Schpo   GDHTGQLWLN  VFDDVGKLIM  HKTADELNDL  .QENDENAFM  NCMAEACYMP
Rfal_Yeast   IDETNQLWLT  LFDDQAKQLL  GVDANTLMSL  .KEEDPNEFT  KITQSIQMNE 601                                                                    650
ZMRPALSH1    HLFRVSVTQH  EYMNEKRQRI  TVRGEAPVDF  AAESKYLLEE  IAKLTAC*~~
ZMRPALSH2    HLFRVSVTQH  EYNNEKRQRI  TVRSEAPVEH  AAESKYLLEQ  IAKLTA***~
    024183   HLFRVSVTQN  EYMNEKRQRI  TVRSEAPVDH  AAEAKYMLEE  IAKLTGC~~~
Rfal_Xenla   YTFRARVKLE  TYNDESRIKA  TAVDVKPVDH  KEYSRRLIMN  IRKMATQGV~
Rfal_Human   FIFRVRVKVE  TYNDESRIKA  TVMDVKPVDY  REYGRRLVMS  IRRSALM~~~
Rfal_Drome   HIFKLRCKNE  VYGDMTRNKL  TVQSVAPINH  KEYNKHLLKE  LQELTGIGSS
Rfal_Schpo   YIFQCRAKQD  NFKGENRVRY  TVMSINQMDW  KEESKRLINF  IESAQ~~~~~
Rfal_Yeast   YDFRIRARED  TYNDQSRIRY  TVANLHSLNY  RAEADYLADE  LSKALLA~~~

651
ZMRPALSH1    ~
ZMRPALSH2    ~
    024183   ~
Rfal_Xenla   ~
Rfal_Human   ~
Rfal_Drome   N
Rfal_Schpo   ~
Rfal_Yeast   ~
```

Comparison of eukaryotic RPA LS amino acid sequences

FIG. 1C.

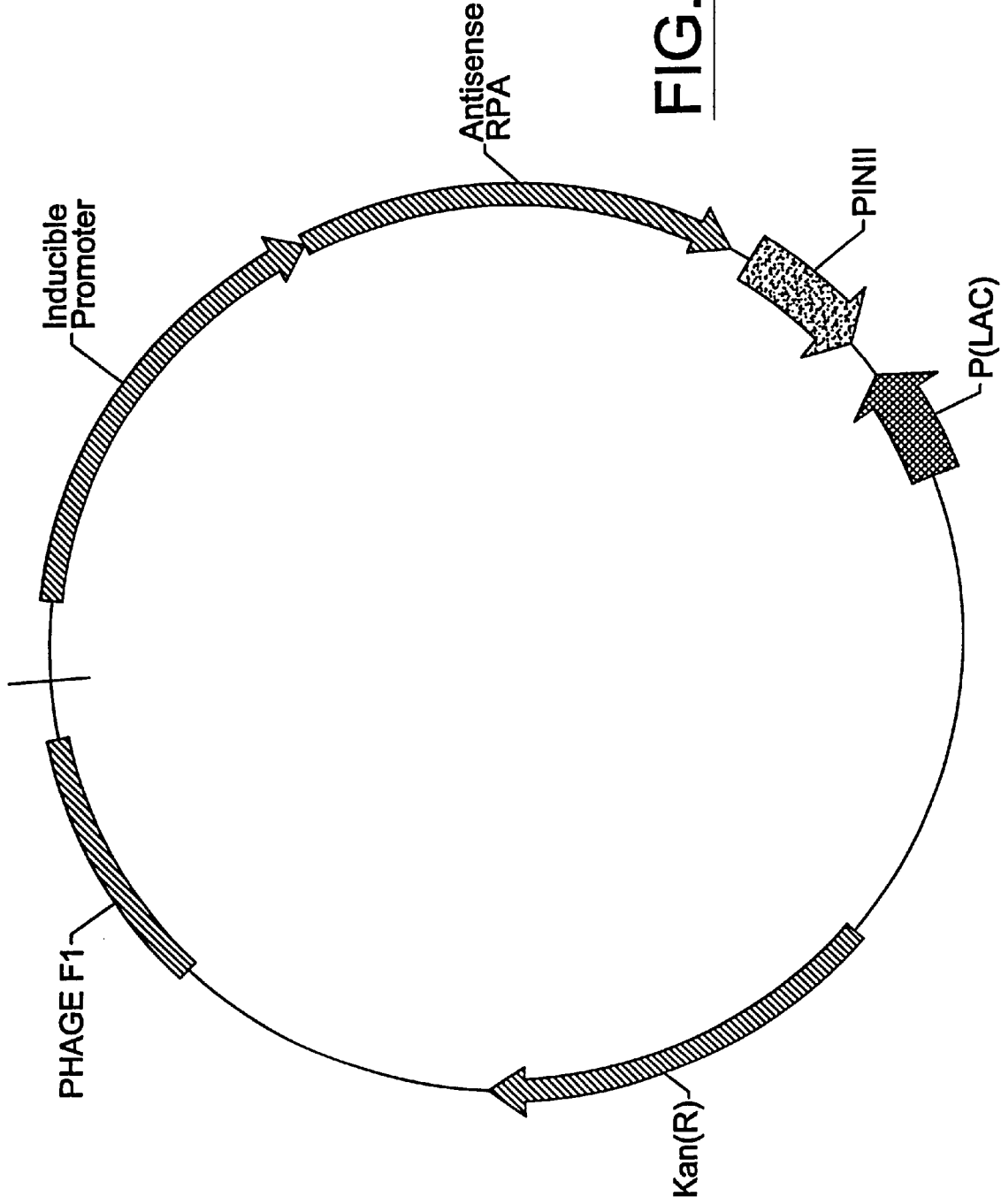

MAIZE REPLICATION PROTEIN A AND USE

CROSS-REFERENCE TO RELATED APPLICATION

This application claims the benefit of U.S. Provisional Application No. 60/100,690 filed Sep. 17, 1998 and from No. 60/123,896 filed Mar. 11, 1999.

FIELD OF THE INVENTION

The invention relates to the genetic manipulation of plants, particularly to modulating DNA metabolism in transformed plants and plant cells.

BACKGROUND OF THE INVENTION

Replication protein A (RPA) is a single-stranded DNA-binding protein that is required for multiple processes in eukaryotic cells. RPA from human cells is a stable complex of 70-, 32-, and 14-kDa subunits. Homologues of RPA have been identified in all eukaryotes examined. However, only human RPA and closely related homologues can support SV40 DNA replication.

The RPA complex appears to be highly conserved in all eukaryotes. The three RPA genes in budding yeast cells are essential for cell viability. Nevertheless, yeast RPA only partially substitutes for human RPA in the in vitro replication of simian virus 40 indicating that species-specific interactions between RPA and other replication proteins may be important for its biological activity.

RPA binds tightly to single stranded DNA as a heterotrimeric complex. The binding activity has been localized to the 70 kDa subunit. The affinity of RPA for both double-stranded DNA and RNA is at least three orders of magnitude lower than it is for single-stranded DNA. It has been reported that RPA binds preferentially to the pyrimidine-rich strand of both S. cerevisiae sequences and the SV40 origin of replication. However, studies examining the determinants of replication origins in S. cerevisiae indicate that this preferential binding is not critical for the initiation of DNA replication.

Subunits of RPA in the 70-, 32- and 14 kDa ranges have been identified from various sources. The 32 kDa subunit has also been referred to as "RPA2", "B", "small", "32 kDa", "P32", "P34", and "middle" subunit. For the purposes of this invention, the "middle" subunit is intended as the subunit having a molecular weight of about 32 kDa.

The middle subunit of RPA has a role in cell cycle regulation; single stranded DNA binding; affinity of DNA binding; species-specificity of DNA binding; DNA recombination, repair, replication and metabolism; and response to DNA damages. (Anderson (1966) Calif. Inst. Technol.; Seroussi et al. (1993) J. Biol. Chem. 268:7147–54; Kenny et al. (1989) Proc. Natl. Acad. Sci. USA 86:9757–61; Brush et al. (1995) Methods Enzymol. 262:522–48, Stigger et al. (1994) Proc. Natl. Acad. Sci. USA 91:579–83; Philipova et al. (1996) Genes Dev. 10:2222–33).

Much research has centered on the exploration of the biochemical and genetic mechanisms by which cell cycle regulation of DNA synthesis is achieved. While there have been advances in delineating the existence of cell cycle proteins, more information is needed on the mechanism of action of DNA replication, recombination, and repair. Furthermore, methods for regulating or altering the cell cycle is needed.

Related Literature

Braun et al. (1997) Biochemistry 36:8443–8454; report on the role of protein-protein interactions and the function of replication protein A. It is reported that RPA modulates the activity of DNA polymerase α by multiple mechanisms.

Loor et al. (1997) Nucleic Acids Research 25:5041–5046 report on the identification of DNA replication in cell cycle proteins that interact with proliferating cell nuclear antigen.

Longhese et al. (1994) Molecular and Cellular Biology 14:7884–7890 report that replication factor A is required for in vivo DNA replication, repair, and recombination.

Stigger et al. (1998) J. Biol. Chem. 273:9337–9343 provide a functional analysis of human replication protein A in nucleotide excision repair.

Abremova et al. (1997) Proc. Natl. Acad. Sci. USA 94:7186–7191 report that the interaction between replication protein A and p53 is disrupted after ultraviolet damage in a DNA repair-dependent manner.

New et al. (1998) Nature 391:407–410 reports that RAD52 protein stimulates DNA strand exchange by RAD51 and replication protein A. Stimulation was dependent on the concerted action of both RAD51 protein and RPA implying that specific protein-protein interactions between RAD52 protein, RAD51 protein and RPA are required.

Dutta et al. (1992) EMBO J 11(6):2189–2199 and Niu et al. (1997) J. Biol. Chem. 272(19):12634–41 report cell cycle-dependent phosphorylation of the middle subunit of RPA, implying a role for the subunit in cell cycle regulation.

Bochkareva et al. (1998) J. Biol. Chem. 273(7):3932–3936 report the formation of a single stranded DNA binding site on the human RPA middle subunit.

Mass et al. (1998) Mol. Cell. Biol. 18(11):6399–6407 report that the RPA middle subunit contacts nascent simian virus 40 DNA, particularly the early DNA chain intermediates synthesized by DNA polymerase alpha-primase (RNA-DNA primers), but not more advanced products.

Lavrik et al. (1998) Nucleic Acids Res 26(2):602–607 report on location of binding of individual subunits of human RPA to DNA primer-template complexes in various elongation reactions.

Sibenaller et al. (1998) 37(36):12496–12506 report that differences in the activity of the middle (32 kDa) and the small (14 Kda) subunits of RPA are responsible for variations in the single stranded DNA-binding properties of sacchromyces cerevisiae and human RPA, thus implying a role for the subunits in species-specificity of DNA binding of RPA.

SUMMARY OF THE INVENTION

Compositions and methods for modulating DNA metabolism in a host cell is provided. Particularly, the complete cDNA and amino acid sequence for homologues of maize replication protein A (RPA) large- and middle subunits are provided. The sequences of the invention find use in modulating DNA replication, DNA repair, and recombination.

Transformed plants can be obtained having altered metabolic states. The invention has implications in genetic transformation and gene targeting in plants. Additionally, the methods can be used to promote cell death particularly in an inducible or tissue-preferred manner.

BRIEF DESCRIPTION OF THE DRAWINGS

FIGS. 1A–C provides a comparison of eukaryotic RPA large subunit amino acid sequences. Amino acid sequences for the RPA large subunits from Sacchromyces Cerevisiae (Rfal Yeast, SEQ ID NO:10), Schizosacchromyces pombe (Rfal_Schpo, SEQ ID NO: 9), Drosophila melanogaster (Rfal_Drome, SEQ ID NO:8), Homo sapiens (Rfal_Human, SEQ ID NO: 7), Xenopus laevis (Rfa_Xenla, SEQ ID NO: 6), and *Oryza sativa* (O24183, SEQ ID NO:5) were compared with the maize RPA LS homologue 1 (ZMRPALSH1, SEQ ID NO:2) and homologue 2 (ZMPRALSH2, SEQ ID NO:4) using the GCG PileUp program utilizing default parameters. The putative zinc finger region is shown in italics.

FIG. 2 provides an expression construct for inducible expression of the maize RPA large or middle subunit antisense construct.

DETAILED DESCRIPTION OF THE INVENTION

Nucleotide sequences and proteins useful for modulating DNA metabolism are provided. The nucleotide and amino acid sequences correspond to the maize replication protein A (RPA) subunits. RPA is a single-stranded DNA-binding protein that is required for multiple processes in DNA metabolism, including DNA replication, DNA repair, and recombination. The RPA complex generally comprises subunits of approximately 70, 32, and 14 kDa. By "large subunit", "middle subunit", and "small subunit" is herein intended a RPA subunit having the approximate molecular weight of 70-, 32-, and 14 kDa respectively. The sequences of the invention comprise the large- and middle subunits of the RPA complex. The sequences of the invention additionally find use in modulating gene expression.

Compositions of the invention include RPA nucleotide and amino acid sequences that are involved in modulating DNA metabolism. In particular, the present invention provides for isolated nucleic acid molecules comprising nucleotide sequences encoding the amino acid sequences shown in SEQ ID NOs:2 and 4 for the large subunit, and SEQ ID NOs: 12, 14, 16, 18, 20, and 22 for the middle subunit. SEQ ID NO:2 and SEQ ID NO:4 correspond to the amino acid sequences for the maize RPA large subunit homologue 1 (ZmRPALSH1) and homologue 2 (ZmRPALSH2). SEQ ID NOs: 12, 14, 16, 18, 20, and 22 correspond to the amino acid sequences for the maize middle subunit homologue 1 (ZmRPAMSH1), homologues 2 and 3 (ZmRPAMSH2 and ZmRPAMSH3), homologue 4 (ZmRPAMSH4); homologue 5 (ZmRPAMSH5); homologue 6 (ZmRPAMSH6); and homologue 7 (ZmRPAMSH7) respectively.

For the large subunit, the present invention alternatively provides the nucleotide sequences encoding the DNA sequences deposited in a bacterial host as Patent Deposit Nos: 98754 and 98843. For the large subunits, further are polypeptides having an amino acid sequence encoded by a nucleic acid molecule described herein, for example those set forth in SEQ ID NOs: 1 and 3, those deposited in a bacterial host as Patent Deposit Nos: 98754 and 98843, and fragments and variants thereof.

Plasmids containing the RPA large subunit nucleotide sequences of the invention were deposited with the Patent Depository of the American Type Culture Collection (ATCC), Manassas, Va., and assigned Patent Deposit NOs: 98754 and 98843. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

Nucleotide sequences encoding the amino acid sequences for the maize RPA large subunit homologue 1 (ZmRPALSH1) and homologue 2 (ZmRPALSH2) are set forth in SEQ ID NOs 1 and 3. Nucleotide sequences encoding the amino acid sequences for the maize RPA middle subunit homologue 1 (ZmRPAMSH1); homologues 2 and 3 (ZmRPAMSH2 and ZmRPAMSH3); homologue 4 (ZmRPAMSH4); homologue 5 (ZmRPAMSH5); homologue 6 (ZmRPAMSH6); and homologue 7 (ZmRPAMSH7) are set forth in SEQ ID NOs: 11, 13, 15, 17, 19, and 21 respectively.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

RPA binds tightly to single-stranded DNA (ssDNA). The affinity of binding to double-stranded DNA (dsDNA) is three to four orders of magnitude lower than the binding affinity for ssDNA. Because RPA has been found to bind specifically to certain dsDNA sequences that seem to be involved in the regulation of transcription, modulation of gene expression may be affected by an increase or decrease in RPA expression in the host cell.

RPA has a wide range of activity and therefore uses relating to DNA metabolism and cell cycle. RPA interacts specifically with several proteins required for nucleotide excision repair. Interactions with repair proteins indicate that RPA may be important for efficient damage recognition and cleavage. RPA additionally interacts with RAD52 protein, a protein that is essential for dsDNA-break repair. This interaction appears to be essential for homologous recombination. In this manner, expression of the nucleotides of the invention may promote homologous recombination by recruiting factors which are essential for recombination to occur. Thus, the methods and compositions of the invention find use in promoting homologous recombination.

In one embodiment, genetic manipulation by homologous recombination can be improved by either expression of the RPA coding sequences of the invention during transformation, or by providing RPA protein. RPA protein, for example, may be provided as a coating to particles during particle bombardment. Alternatively, DNA constructs providing for the expression of RPA may be included with the DNA to be transformed. The increase in RPA during transformation, particularly integration of polynucleotides by homologous recombination, promotes integration and insertion of the DNA sequences of interest into the plant genome.

In the same manner, it may be beneficial to inhibit the expression or presence of the RPA protein to encourage non-specific recombination events. In this manner, antibodies, peptides, antisense oligonucleotides and the like may be utilized to inhibit the activity of RPA. Alternatively, antisense constructs may be provided to inhibit the expression of RPA and encourage non-specific recombination.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al. (1988) *Nature* 334:585–591.

A variety of cross-linking agents, alkylating agents and radical generating species as pendant groups on polynucleotides of the present invention can be used to bind, label, detect, and/or cleave nucleic acids. For example, Vlassov, V. V. et al. (1986) *Nucleic Acids Res.* 14:4065–4076, describe covalent bonding of a single-stranded DNA fragment with alkylating derivatives of nucleotides complementary to target sequences. A report of similar work by the same group is that by Knorre et al. (1985) *Biochimie* 67:785–789. Iverson and Dervan also showed sequence-specific cleavage of single-stranded DNA mediated by incorporation of a modified nucleotide which was capable of activating cleavage (1987) *J. Am. Chem. Soc.* 109:1241–1243). Meyer et al. (1989) *J. Am. Chem. Soc.* 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee et al. (1988) *Biochem.* 27:3197–3203. Use of crosslinking in triple-helix forming probes was also disclosed by Home et al. (1990) *J. Am. Chem. Soc.* 112:2435–2437. Use of N4, N4-ethanocytosine as an alkylating agent to crosslink to single-stranded oligonucleotides has also been described by Webb et al. (1986) *J. Am. Chem. Soc.* 108:2764–2765; Webb et al. (1986) *Nucleic Acids Res.* 14:7661–7674; Feteritz et al. (1991) *J. Am. Chem. Soc.* 113:4000. Various compounds to bind, detect, label, and/or cleave nucleic acids are known in the art. See, for example, U.S. Pat. Nos. 5,543,507; 5,672,593; 5,484,908; 5,256,648; and 5,681,941.

RPA is required for the replication of chromosomal DNA. Inhibition of endogenous RPA expression is deleterious to the cell, organism, or plant. Thus, the constructs of the invention can be used to selectively kill target cells or tissues. This can be accomplished through the use of inducible or tissue-preferred promoters. In this manner, the sequences of the invention may find use in enhancing pathogen resistance. An antisense construct for the RPA coding sequence is operably linked to a pathogen-inducible promoter. Upon contact with the pathogen, the RPA antisense construct is expressed resulting in cell death and effectively preventing the invasion of the pathogen.

The invention is drawn to compositions and methods for inducing resistance in a plant to plant pests. Accordingly, the compositions and methods are also useful in protecting plants against fungal pathogens, viruses, nematodes, insects and the like.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened. The methods of the invention can be utilized to protect plants from disease, particularly those diseases that are caused by plant pathogens.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Scierotium roltsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines Fusarium solani;* Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata;* Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae;* Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo*

*tragopogonis;* Corn: *Fusarium moniliforme* var. *subglutinans, Erwinia stewartii, Fusarium moniliforme, Gibberella zeae (Fusarium graminearum), Stenocarpella maydi (Diplodia maydis), Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora,* Corn stunt spiroplasma, *Diplodia macrospora, Sclerophihora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola (Glomerella graminicola), Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Nematodes include parasitic nematodes such as root-knot, cyst, and lesion nematodes, including Heterodera and Globodera spp; particularly *Globodera rostochiensis* and *globodera pailida* (potato cyst nematodes); *Heterodera glycines* (soybean cyst nematode); *Heterodera schachtii* (beet cyst nematode); and *Heterodera avenae* (cereal cyst nematode).

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis,* European corn borer; *Agrotis ipsilon,* black cutworm; *Helicoverpa zea,* corn earworm; *Spodoptera frugiperda,* fall armyworm; *Diatraea grandiosella,* southwestern corn borer; *Elasmopalpus lignosellus,* lesser cornstalk borer; *Diatraea saccharalis,* surgarcane borer; *Diabrotica virgifera,* western corn rootworm; *Diabrotica longicornis barberi,* northern corn rootworm; *Diabrotica undecimpunctata howardi,* southern corn rootworm; Melanotus spp., wireworms; *Cyclocephala borealis,* northern masked chafer (white grub); *Cyclocephala immaculata,* southern masked chafer (white grub); *Popillia japonica,* Japanese beetle; *Chaetocnema pulicaria,* corn flea beetle; *Sphenophorus maidis,* maize billbug; *Rhopalosiphum maidis,* corn leaf aphid; *Anuraphis maidiradicis,* corn root aphid; *Blissus leucopterus leucopterus,* chinch bug; *Melanoplus femurrubrum,* redlegged grasshopper; *Melanoplus sanguinipes,* migratory grasshopper; *Hylemya platura,* seedcorn maggot; *Agromyza parvicornis,* corn blot leafminer; *Anaphothrips obscrurus,* grass thrips; *Solenopsis milesta,* thief ant; *Tetranychus urticae,* twospotted spider mite; Sorghum: *Chilo partellus,* sorghum borer; *Spodoptera frugiperda,* fall armyworm; *Helicoverpa zea,* corn earworm; *Elasmopalpus lignosellus,* lesser cornstalk borer; *Feltia subterranea,* granulate cutworm; *Phyllophaga crinita,* white grub; Eleodes, Conoderus, and Aeolus spp.; wireworms; *Oulema melanopus,* cereal leaf beetle; *Chaetocnema pulicaria,* corn flea beetle; *Sphenophorus maidis,* maize bilibug; *Rhopalosiphum maidis;* corn leaf aphid; *Sipha flava,* yellow sugarcane aphid; *Blissus leucopterus leucopterus,* chinch bug; *Contarinia sorghicola,* sorghum midge; *Tetranychus cinnabarinuis,* carmine spider mite; *Tetranychus urticae,* twospotted spider mite; Wheat: *Pseudaletia unipunctata,* army worm; *Spodoptera frugiperda,* fall armyworm; *Elasmopalpus lignosellus,* lesser cornstalk borer; *Agrotis orthogonia,* western cutworm; *Elasmopalpus lignosellus,* lesser cornstalk borer; *Oulema melanopus,* cereal leaf beetle; *Hypera punctata,* clover leaf weevil; *Diabrotica undecimpunctata howardi,* southern corn rootworm; Russian wheat aphid; *Schizaphis graminum,* greenbug; *Macrosiphum avenae,* English grain aphid; *Melanoplus femurrubrum,* redlegged grasshopper; *Melanoplus differentialis,* differential grasshopper; *Melanoplus sanguinipes,* migratory grasshopper; *Mayetiola destructor,* Hessian fly; *Sitodiplosis mosellana,* wheat midge; *Meromyza americana,* wheat stem maggot; *Hylemya coarciata,* wheat bulb fly; *Frankliniella fusca,* tobacco thrips; *Cephus cinctus,* wheat stem sawfly; *Aceria tulipae,* wheat curl mite; Sunflower: *Suleima helianthana,* sunflower bud moth; *Homoeosoma electellum,* sunflower moth; *zygogramma exclamationis,* sunflower beetle; *Bothyrus gibbosus,* carrot beetle; *Neolasioptera murtfeldtiana,* sunflower seed midge; Cotton: *Heliothis virescens,* cotton budworm; *Helicoverpa zea,* cotton bollworm; *Spodoptera exigua,* beet armyworm; *Pectinophora gossypiella,* pink bollworm; *Anthonomus grandis grandis,* boll weevil; *Aphis gossypii,* cotton aphid; *Pseudatomoscelis seriatus,* cotton fleahopper; *Trialeurodes abutilonea,* bandedwinged whitefly; *Lygus lineolaris,* tarnished plant bug; *Melanoplus femurrubrum,* redlegged grasshopper; *Melanoplus differentialis,* differential grasshopper; *Thrips tabaci,* onion thrips; *Franklinkiella fusca,* tobacco thrips; *Tetranychus cinnabarinus,* carmine spider mite; *Tetranychus urticae,* twospotted spider mite; Rice: *Diatraea saccharalis,* sugarcane borer; *Spodoptera frugiperda,* fall armyworm; *Helicoverpa zea,* corn earworm; *Colaspis brunnea,* grape colaspis; *Lissorhoptrus oryzophilus,* rice water weevil, *Sitophilus oryzae,* rice weevil; *Nephotettix nigropictus,* rice leafhopper; *Blissus leucopterus leucopterus,* chinch bug; *Acrosternum hilare,* green stink bug; Soybean: *Pseudoplusia includens,* soybean looper; *Anticarsia gemmatalis,* velvetbean caterpillar; *Plathypena scabra,* green cloverworm; *Ostrinia nubilalis,* European corn borer; *Agrotis ipsilon,* black cutworm; *Spodoptera exigua,* beet armyworm; *Heliothis virescens,* cotton budworm; *Helicoverpa zea,* cotton bollworm; *Epilachna*

*varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly, *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; Delia ssp., Root maggots.

A number of promoters can be used in the practice of the invention. The promoters can be selected based on the desired outcome. The nucleic acids can be combined with constitutive, tissue-preferred, or other promoters for expression in plants.

A plant promoter can be employed which will direct expression of a polynucleotide of the present invention in all tissues of a regenerated plant. Such promoters are referred to herein as "constitutive" promoters and are active under most environmental conditions and states of development or cell differentiation. Such constitutive promoters include, for example, the core promoter of the Rsyn7 (WO 99/43838); the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Alternatively, the plant promoter can direct expression of a polynucleotide of present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adhl promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds, or flowers. An exemplary promoter is the anther specific promoter 5126 (U.S. Pat. Nos. 5,689,049 and 5,689,051). The operation of a promoter may also vary depending on its location in the genome. Thus, an inducible promoter may become fully or partially constitutive in certain locations.

The promoters can be selected based on the desired outcome. When the genes are expressed at levels to cause cell death, an inducible promoter or tissue specific promoters can be used to drive the expression of the genes of the invention. The inducible promoter must be tightly regulated to prevent unnecessary cell death, yet be expressed in the presence of a pathogen to prevent infection and disease symptoms. Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. See also the copending application entitled "Inducible Maize Promoters", U.S. application Ser. No. 09/257,583, filed Feb. 25, 1999, herein incorporated by reference.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331, Somsisch et al. (1986) *Proc. Natl. Acad. Sci. USA* 83:2427–2430; Somsisch et al. (1988) *Mol. Gen. Genet.* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189–200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425–449; Duan et al. (1996) *Nature Biotechnology* 14:494–498), wun1 and wun2, U.S. Pat. No. 5,428,148; win1 and win2 (Stanford et al. (1989) *Mol. Gen. Genet.* 215:200–208); systemin (McGurl et al. (1992) *Science* 225:1570–1573); WIP1 (Rohmeier et al. (1993) *Plant Mol Biol.* 22:783–792; Eckelkamp et al. (1993) *FEBS Letters* 323:73–76); MPI gene (Corderok et al. (1994) *Plant J.* 6(2):141–150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

Where low level expression is desired, weak promoters will be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 (WO 99/43838), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, the copending application entitled "Constitutive Maize Promoters", U.S. application Ser. No. 09/257,584, filed Feb. 25, 1999, and herein incorporated by reference.

Tissue-preferred promoters can be utilized to target enhanced RPA expression within a particular plant tissue. In this aspect of the invention, the antisense constructs are useful for tissue-preferred expression. Male or female sterility may be affected by use of the antisense constructs with tissue-preferred promoters. Although not a limitation, of particular interest are promoters for male sterility. For example, the anther-preferred promoter 5126 can be used. See, for example, U.S. Pat. Nos. 5,689,049 and 5,689,051, herein incorporated by reference.

Tissue-preferred promoters include Yamamoto et al. (1997) *Plant J.* 12(2)255–265; Kawamata et al. (1997) *Plant Cell Physiol.* 38(7):792–803; Hansen et al. (1997) *Mol. Gen Genet.* 254(3):337–343, Russell et al. (1997) *Transgenic Res.* 6(2):157–168, Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol Biol.* 23(6):1129–1138; Matsuoka et al. (1993) *Proc Natl. Acad. Sci. USA* 90(20):9586–9590; and Guevara-Garcia et al. (1993) *Plant J.* 4(3):495–505. Such promoters can be modified, if necessary, for weak expression.

Leaf-specific promoters are known in the art. See, for example, Yamamoto et al. (1997) *Plant J.* 12(2):255–265; Kwon et al. (1994) *Plant Physiol.* 105:357–67; Yamamoto et al. (1994) *Plant Cell Physiol.* 35(5):773–778; Gotor et al. (1993) *Plant J.* 3:509–18; Orozco et al. (1993) *Plant Mol. Biol.* 23(6):1129–1138; and Matsuoka et al. (1993) *Proc. Natl. Acad. Sci. USA* 90(20):9586–9590.

Root-specific promoters are known and can be selected from the many available from the literature or isolated de novo from various compatible species. See, for example, Hire et al. (1992) *Plant Mol. Biol.* 20(2): 207–218 (soybean root-specific glutamine synthetase gene); Keller and Baumgartner (1991) *Plant Cell* 3(10):1051–1061 (root-specific control element in the GRP 1.8 gene of French bean); Sanger et al. (1990) *Plant Mol. Biol.* 14(3):433–443 (root-specific promoter of the mannopine synthase (MAS) gene of *Agrobacterium tumefaciens*); and Miao et al. (1991) *Plant Cell* 3(1):11–22 (full-length cDNA clone encoding cytosolic glutamine synthetase (GS), which is expressed in roots and root nodules of soybean). See also Bogusz et al. (1990) *Plant Cell* 2(7):633–641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus,* and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69–76). They concluded that enhancer and tissue-preferred DNA determinants are dissociated in those promoters. Teeri et al. (1989) used gene fusion to lacZ to show that the Agrobacterium T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343–350). The TR1' gene, fused to nptII (neomycin phosphotransferase II) showed similar characteristics. Additional root-preferred promoters include the VfENOD-GRP3 gene promoter (Kuster et a. (1995) *Plant Mol. Biol.* 29(4):759–772); and rolB promoter (Capana et al. (1994) *Plant Mol. Biol.* 25(4):681–691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see the copending application entitled "Seed-Preferred Promoters," U.S. application Ser. No. 60/097,233, filed Aug. 20, 1998, herein incorporated by reference. Gama-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter RPA content and/or composition in a desired tissue, or to generate sterile plants. Optionally, RPA nucleic acids from a variety of sources, as discussed above can be employed to create male sterile plants. In optional embodiments, the RPA gene or cDNA is operably linked to an anther-specific promoter such as 5126, as discussed above. Preferably, the male sterile plant is maize.

Thus, in some embodiments, the nucleic acid construct will comprise a promoter functional in a plant cell, such as in *Zea mays,* operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a RPA gene so as to control the expression of the gene. Gene expression can be modulated under conditions suitable for plant growth so as to alter RPA content and/or composition. Thus, the present invention provides compositions, and methods for making, heterologous promoters and/or enhancers operably linked to a native, endogenous (i.e., non-heterologous) form of a polynucleotide of the present invention.

Methods for identifying promoters with a particular expression pattern, in terms of e.g., tissue type, cell type, stage of development, and/or environmental conditions, are well known in the art. See, e.g., *The Maize Handbook*, Chapters 114–115, Freeling and Walbot, eds., Springer, New York (1994); *Corn and Corn Improvement*, $3^{rd}$ edition, Chapter 6, Sprague and Dudley, eds., American Society of Agronomy, Madison, Wis. (1988). A typical step in promoter isolation methods is identification of gene products that are expressed with some degree of specificity in the target tissue. Amongst the range of methodologies are: differential hybridization to cDNA libraries; subtractive hybridization; differential display; differential 2-D protein gel electrophoresis; DNA probe arrays; and isolation of proteins known to be expressed with some specificity in the target tissue. Such methods are well known to those of skill in the art. Commercially available products for identifying promoters are known in the art such as Clontech's (Palo Alto, Calif.) Universal GenomeWalker Kit.

For the protein-based methods, it is helpful to obtain the amino acid sequence for at least a portion of the identified protein, and then to use the protein sequence as the basis for preparing a nucleic acid that can be used as a probe to identify either genomic DNA directly, or preferably, to identify a cDNA clone from a library prepared from the target tissue. Once such a cDNA clone has been identified, that sequence can be used to identify the sequence at the 5' end of the transcript of the indicated gene. For differential hybridization, subtractive hybridization and differential display, the nucleic acid sequence identified as enriched in the target tissue is used to identify the sequence at the 5' end of the transcript of the indicated gene. Once such sequences are identified, starting either from protein sequences or nucleic acid sequences, any of these sequences identified as being from the gene transcript can be used to screen a genomic library prepared from the target organism. Methods for identifying and confirming the transcriptional start site are well known in the art.

In the process of isolating promoters expressed under particular environmental conditions or stresses, or in specific tissues, or at particular developmental stages, a number of genes are identified that are expressed under the desired circumstances, in the desired tissue, or at the desired stage. Further analysis will reveal expression of each particular gene in one or more other tissues of the plant. One can identify a promoter with activity in the desired tissue or condition but that do not have activity in any other common tissue.

To identify the promoter sequence, the 5' portions of the clones described here are analyzed for sequences characteristic of promoter sequences. For instance, promoter sequence elements include the TATA box consensus sequence (TATAAT), which is usually an AT-rich stretch of 5–10 bp located approximately 20 to 40 base pairs upstream of the transcription start site. Identification of the TATA box is well known in the art. For example, one way to predict the location of this element is to identify the transcription start site using standard RNA-mapping techniques such as primer extension, S1 analysis, and/or RNase protection. To confirm the presence of the AT-rich sequence, a structure-function analysis can be performed involving mutagenesis of the putative region and quantification of the mutation's effect on expression of a linked downstream reporter gene. See, e.g., *The Maize Handbook*, Chapter 114, Freeling and Walbot, eds., Springer, New York (1994).

In plants, further upstream from the TATA box, at positions −80 to −100, there is typically a promoter element (i.e., the CAAT box) with a series of adenines surrounding the trinucleotide G (or T) N G. J. Messing et al., in *Genetic Engineering in Plants*, Kosage, Meredith and Hollaender, eds., pp. 221–227 (1983). In maize, there no well-conserved CAAT box but there are several short, conserved protein-binding motifs upstream of the TATA box. These include motifs for the transacting transcription factors involved in light regulation, anaerobic induction, hormonal regulation, or anthocyanin biosynthesis, as appropriate for each gene.

Once promoter and/or gene sequences are known, a region of suitable size is selected from the genomic DNA that is 5' to the transcriptional start, or the translational start site, and such sequences are then linked to a coding sequence. If the transcriptional start site is used as the point of fusion, any of a number of possible 5' untranslated regions can be used in between the transcriptional start site and the partial coding sequence. If the translational start site at the 3' end of the specific promoter is used, then it is linked directly to the methionine start codon of a coding sequence.

If polypeptide expression is desired, it is generally desirable to include apolyadenylation region at the 3'-end of a polynucleotide coding region. The polyadenylation region can be derived from the natural gene, from a variety of other plant genes, or from T-DNA. The 3' end sequence to be added can be derived from, example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman et al. (1988) *Mol. Cell Biol.* 8:4395–4405; Callis et al. (1987) *Genes Dev.* 1:1183–1200. Such intron enhancement of gene expression is typically greatest when placed near the 5' end of the transcription unit. Use of maize introns Adhl-S intron 1, 2, and 6, the Bronze-1 intron are known in the art. See generally, *The Maize Handbook*, Chapter 116, Freeling and Walbot, eds., Springer, New York (1994).

The vector comprising the sequences from a polynucleotide of the present invention could comprise a selectable marker gene for the selection of transformed cells or tissues. Selectable marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72;

Reznikoff (1992) *Mol. Microbiol.* 6:2419–2422; Barkley et al. (1980) in *The Operon,* pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356;Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162, Degenkolb et al. (1991) *Antimicrob. Agents Chemother.* 35:1 591–1595; Kleinschnidt et al. (1988) *Biochemistry* 27:1094–1104, Bonin (1993) Ph.D. Thesis, University of Heidelberg; Gossen et al. (1992) *Proc. Natl. Acad Sci. USA* 89:5547–5551; Oliva et al. (1992) *Antimicrob. Agents Chemother.* 36:913–919; Hlavka et al. (1985) *Handbook of Experimental Pharmacology,* Vol. 78 ( Springer-Verlag, Berlin); Gill et al. (1988) *Nature* 334:721–724. Such disclosures are herein incorporated by reference.

The above list of selectable marker genes is not meant to be limiting. Any selectable marker gene can be used in the present invention.

Typical vectors useful for expression of genes in higher plants are well known in the art and include vectors derived from the tumor-inducing (Ti) plasmid of *Agrobacterium tumefaciens* described by Rogers et al. (1987) *Meth. in Enzymol.* 153:253–277. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al. (1987) *Gene* 61:1–11 and Berger et al. (1989) *Proc. Natl. Acad. Sci. (USA)* 86:8402–8406. Another useful vector herein is plasmid pBI101.2 that is available from Clontech Laboratories, Inc. (Palo Alto, Calif.).

As discussed above, a polynucleotide of the present invention can be expressed in either sense or antisense orientation as desired. It will be appreciated that control of gene expression in either sense or antisense orientation can have a direct impact on the observable plant characteristics. Antisense technology can be conveniently used for gene expression in plants. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy et al. (1988) *Proc. Natl. Acad. Sci. (USA)* 85:8805–8809; and Hiatt et al., U.S. Pat. No. 4,801,340.

In the methods of the invention, it is recognized that the entire coding sequence for the RPA construct may be utilized. Alternatively, portions or fragments of the sequence may be used in DNA constructs.

Fragments and variants of the disclosed nucleotide sequences and proteins encoded thereby are encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence modulate DNA metabolism. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a RPA nucleotide sequence that encodes a biologically active portion of a RPA protein of the invention will encode at least 15, 25, 30, 50, 100, 150, 200, or 250 contiguous amino acids, or up to the total number of amino acids present in a full-length RPA protein of the invention (for example, 623, 617, 273, 273, 273, 318, 273, 273 amino acids for SEQ ID NOs: 2, 4, 12, 14, 16, 18, 20, and 22 respectively. Fragments of a RPA nucleotide sequence that are useful as hybridization probes for PCR primers generally need not encode a biologically active portion of a RPA protein.

Thus, a fragment of a RPA nucleotide sequence may encode a biologically active portion of a RPA protein, or it may be a fragment that can be used as a hybridization probe or PCR primer using methods disclosed below. A biologically active portion of a RPA protein can be prepared by isolating a portion of one of the RPA nucleotide sequences of the invention, expressing the encoded portion of the RPA protein (e.g., by recombinant expression in vitro), and assessing the activity of the encoded portion of the RPA protein. Nucleic acid molecules that are fragments of a RPA nucleotide sequence comprise at least 16, 20, 50, 75, 100, 150, 200, 250, 300, 30 350, 400, 450, 500, 550, 600, 650, 700, 800, 900, 1,000 nucleotides, or up to the number of nucleotides present in a full-length RPA nucleotide sequence disclosed herein (for example, 2497, 2202, 1124, 979, 1051, 1087, 1074, and 1231 nucleotides for SEQ ID NOs: 1, 3, 11, 13, 15, 17, 19, and 21 respectively).

By "variants" is intended substantially similar sequences. For nucleotide sequences, conservative variants include those sequences that, because of the degeneracy of the genetic code, encode the amino acid sequence of one of the RPA polypeptides of the invention. Such naturally occurring variants including naturally occurring allelic variants, can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a RPA protein of the invention. Generally, variants of a particular nucleotide sequence of the invention will have at least 40%, 50%, 60%, 70%, generally at least 75%, 80%, 85%, preferably about 90% to 95% or more, and more preferably about 98% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, modulating DNA metabolism as described herein. Such variants may result from, for example, genetic polymorphism or from human manipulation. Biologically active variants of a native RPA protein of the invention will have at least 40%, 50%, 60%, 70%, generally at least 75%, 80%, 85%, preferably about 90% to 95% or more, and more preferably about 98% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the RPA proteins can be prepared by mutations in the DNA. Methods for mutagenesis and nucleotide sequence alterations are well known in the art. See, for example, Kunkel (1985) *Proc. Natl. Acad Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof Such variants will continue to possess the desired activity in influencing DNA metabolism. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequence encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assessing DNA binding, recombination, repair and replication. See, for example, Braun et al. (1997) *Biochemistry* 36:8443–8454; Longhese et al. (1994) *Molecular and Cellular Biology* 14:7884–7890; Stigger et al. (1998) *J. Biol. Chem.* 273:9337–9343; Abremova et al. (1997) *Proc. Natl. Acad. Sci. USA* 94:7186–7191; New et al. (1998) *Nature* 391:407–410; Bochkareva et al. (1998) *J. Biol. Chem.* 273(7):3932–6Mass et al. (1998) *Mol. Cell. Biol.* 18(11):6399–407; Lavrik et al. (1998) *Nucleic Acids Res* 26(2):602–7; Sibenaller et al. (1998) 37(36):12496–506; Matsunaga et al. (1996) *J. Biol. Chem.* 271(19): 11047–50; and Sung (1997) *Genes & Development* 11: 1111–21, herein incorporated by reference.

Variant nucleotide sequences and proteins also encompass nucleotide sequences and proteins derived. from a mutagenic and recombinogenic procedure such as DNA shuffling. With such a procedure, one or more different RPA coding sequences can be manipulated to create a new RPA possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the RPA gene of the invention and other known RPA genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–1075 1 Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

It is recognized that with these nucleotide sequences, antisense constructions, complementary to at least a portion of the messenger RNA (mRNA) for the RPA sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence similarity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034, 323; herein incorporated by reference.

Use of the polypeptides and proteins, and fragments and variants thereof, for producing antibodies are also encompassed by the invention. The invention also encompasses using such antibodies to determine RPA protein levels, and to modulate one or more biological activities or interactions of RPA. Methods for the production of antibodies are known in the art. See, for example, Harlow and Lane, antibodies, A Laboratory Manual, Cold Spring Harbor Publications, New York (1988); and the reference is cited therein.

The RPA sequences of the invention may be optimized for enhanced expression in plants of interest. See, for example, EPA0359472; WO91/16432; Perlak et al. (1991) *Proc. Natl Acad. Sci. USA* 88:3324–3328; and Murray et al. (1989) *Nucleic Acids Res.* 17:477–498. In this manner, the genes can be synthesized utilizing plant-preferred condons. See, for example, Murray et al. (1989) *Nucleic Acids Res.* 17:477–498, the disclosure of which is incorporated herein by reference. In this manner, synthetic genes can also be made based on the distribution of codons a particular host uses for a particular amino acid. Thus, the nucleotide sequences can be optimized for expression in any plant. It is recognized that all or any part of the gene sequence may be optimized or synthetic. That is, synthetic or partially optimized sequences may also be used.

Thus nucleotide sequences of the invention and the proteins encoded thereby include the native forms as well as variants thereof The variant proteins will be substantially homologous and functionally equivalent to the native proteins. A variant of a native protein is "substantially homologous" to the native protein when at least about 80%, more preferably at least about 90%, and most preferably at least about 95% of its amino acid sequence is identical to the amino acid sequence of the native protein. By "functionally equivalent" is intended that the sequence of the variant defines a chain that produces a protein having substantially the same biological effect as the native protein of interest. Such functionally equivalent variants that comprise substantial sequence variations are also encompassed by the invention.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequence set forth herein. Sequences isolated based on their sequence identity to the entire RPA sequences set forth herein or to fragments thereof are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the RPA sequences of the invention. Methods for preparation of probes for hybridization and for construction of cDNA and genomic libraries are generally known in the art and are disclosed in Sambrook et al. (1 989) *Molecular Cloning: A Laboratory Manual* (2d ed., Cold Spring Harbor Laboratory Press, Plainview, N.Y.).

For example, the entire RPA sequence disclosed herein, or one or more portions thereof, may be used as a probe capable of specifically hybridizing to corresponding RPA sequences and messenger RNAs. To achieve specific hybridization under a variety of conditions, such probes include sequences that are unique among RPA sequences and are preferably at least about 10 nucleotides in length, and most preferably at least about 20 nucleotides in length. Such probes may be used to amplify corresponding RPA sequences from a chosen plant by PCR. This technique may be used to isolate additional coding sequences from a desired plant or as a diagnostic assay to determine the presence of coding sequences in a plant Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching, thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology— Hybridization with Nucleic Acid Probes,* Part I, Chapter 2 (Elsevier, New York); and Ausubel et al., eds. (1995) *Current Protocols in Molecular Biology,* Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that have promoter activity or encode for a RPA protein and which hybridize under stringent conditions to the RPA sequences disclosed herein, or to fragments thereof, are encompassed by the present invention. Such sequences will be at least 40% to 50% homologous, about 60% to 70% homologous, and even about 75%, 80%, 85%, 90%, 95% to 98% homologous or more with the disclosed sequences. That is, the sequence identity of sequences may range, sharing at least 40% to 50%, about 60% to 70%, and even about 75%, 80%, 85%, 90%, 95% to 98% or more sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins el al. (1988) *Gene* 73:237–244 (1988); Higgins et al. (1 989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection. Alignment may also be performed manually by inspection.

For purposes of the present invention, comparison of nucleotide or protein sequences for determination of percent sequence identity to the RPA sequences disclosed herein is preferably made using the GCG PileUp program, version 10.00, with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably.at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed. by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Prokaryotic cells may be used as hosts for expression. Prokaryotes most frequently are represented by various strains of *E. coli;* however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang el al. (1977) *Nature* 198:1056), the tryptophan (trp) promoter system (Goeddel et al. (1980) *Nucleic Acids Res.* 8:4057) and the lambda-derived P L promoter and N-gene ribosome binding site (Shimatake et al. (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva et al. (1983) *Gene* 22:229–235; Mosbach et al. (1983) *Nature* 302:543–545).

A variety of eukaryotic expression systems such as yeast, insect cell lines, plant and mammalian cells, are known to those of skill in the art. The sequences of the present invention can be expressed in these eukaryotic systems. In some embodiments, transformed/transfected plant cells are employed as expression systems for production of the proteins of the instant invention.

Synthesis of heterologous proteins in yeast is well known. Sherman, F. et al. (1982) *Methods in Yeast Genetics,* Cold Spring Harbor Laboratory is a well recognized work describing the various methods available to produce the protein in yeast. Two widely utilized yeast for production of eukaryotic proteins are *Saccharomyces cerevisia* and *Pichia pastoris*. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase promoter)), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th edition, 1992).

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See Schneider et al. (1987) *J. Embryol. Exp. Morphol.* 27: 353–365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague et al. (1983) *J. Virol.* 45:773–781). Additionally, gene sequences to control replication in the host cell may be incorporated into the vector such as those found in bovine papilloma virus-type vectors. Saveria-Campo, M., Bovine Papilloma Virus DNA a Eukaryotic Cloning Vector in *DNA Cloning Vol. II a Practical Approach,* D. M. Glover, ed., IRL Press, Arlington, Va. pp. 213–238 (1985).

The sequences of the invention can be introduced into any plant of interest, and used for transformation of any plant species. The sequences to be introduced may be used in expression cassettes for expression in the particular plant of interest.

Plants of interest include, but are not limited to corn (*Zea mays*), Brassica sp. (e.g., *B. napus, B. rapa, B. juncea*), particularly those Brassica species useful as sources of seed oil, alfalfa (*Medicago saliva*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum,* peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (Saccharum spp.), oats, barley, vegetables, ornamentals, and conifers.

Vegetables include tomatoes (*Lycopersicon esculentum*), lettuce (e.g., *Lactuca saliva*), green beans (*Phaseolus vulgaris*), lima beans (*Phaseolus limensis*), peas (Lathyrus spp.), and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pimus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*), true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The RPA coding and antisense sequences of the invention are provided in expression cassettes for expression in the plant of interest. The cassette will include 5' and 3' regulatory sequences operably linked to a RPA sequence of the invention. The cassette may additionally contain at least one additional gene to be cotransformed into the organism. Alternatively, the additional gene(s) can be provided on another expression cassette. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

Such an expression cassette is provided with a plurality of restriction sites for insertion of the RPA sequence to be under the transcriptional regulation of the regulatory regions. The expression cassette may additionally contain selectable marker genes.

The expression cassette will include in the 5'-3' direction of transcription, a transcriptional and translational initiation region, a RPA DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of RPA in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens,* such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *GenesDev.* 5:141–149; Mogen et al. (1990) *Plant Cell* 2:1261–1272; Munroe et al. (1990) *Gene*91:151–158; Ballas et al. (1989) *Nucleic Acids Res.* 17:7891–7903; and Joshi et al. (1987) *Nucleic Acid Res.* 15:9627–9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA,* ed. Cech (Liss, New York), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward.this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The sequences of the present invention can be used to transform or transfect any plant. In this manner, genetically modified plants, plant cells, plant tissue, seed, and the like can be obtained. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods,* ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods,* ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature (London)* 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues,* ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered RPA expression relative to a control plant (i.e., native, non-transgenic). Backcrossing to a parental plant and outcrossing with a non-transgenic plant are also contemplated.

The present invention farther provides a method for modulating (i.e., increasing or decreasing) RPA levels in a plant or part thereof. Modulation can be effected by increasing or decreasing the total amount of RPA (i.e., its content) and/or the ratio of various RPA subunit proteins (i.e., its composition) in the plant. The method comprises transforming a plant cell with a recombinant expression cassette comprising a polynucleotide of the present invention as described above to obtain a transformed plant cell, growing the transformed plant cell under plant forming conditions, and inducing expression of a polynucleotide of the present invention in the plant for a time sufficient to modulate RPA content and/or composition in the plant or plant part.

In some embodiments, RPA in a plant may be modulated by altering, in vivo or in vitro, the promoter of a non-isolated RPA gene to up- or down-regulate gene expression. In some embodiments, the coding regions of native RPA genes an be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate RPA content and/or composition in the plant. Plant forming conditions are well known in the art and discussed briefly, supra.

In general, content or composition is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds that activate expression from these promoters are well known in the art. In preferred embodiments, RPA is modulated in monocots, particularly maize.

The ability of RPA to interact with multiple proteins or protein complexes allows it to participate and regulate these multiple pathways of DNA metabolism. For example, it has been shown in mammalian systems that are RPA interacts with DNA polymerase alpha (Barun el al. (1997) *Biochemistry* 36:8443–8454), p53 (Dutta et al. (1993) *Nature* 365:79–82), RAD 62 (Park et al. (1996) *J. Biol. Chem.* 271:18996–19000).

Participation of the middle subunit of RPA in protein-protein interactions has also been shown. Examples of such interactions include, but are not limited to interactions with XPA protein and RAD 52 (He et al. (1995) *Nature* 374:566–69; Matsuda et al. (1995) *J. Biol. Chem.* 270:4152–57; Li et al. (1995) *Mol. Cell. Biol.* 15:5396–402, Park et al. (1996) *J. Biol. Chem.* 271:18996–19000); and PCNA (Shivji et al. (1995) *Biochemistry* 34:5011–5017).

Similarly, yeast RPA has been shown to be involved in multiple functions in DNA metabolism (Umezu et al. (1998) *Genetics* 148:989–1005). Therefore, the proteins of the invention may be useful as a ligand to purify and clone other proteins involved in DNA recombination, repair, and replication. Particularly, the maize proteins may be useful to purify other maize proteins involved in DNA metabolism. For example, the RPA proteins of the invention may be insolubilized on a solid matrix (e.g. agrose or nylon beads) for affinity purification, or the RPA cDNA may be used as a bait in a yeast to-hybrid system. In this manner, other proteins may be used identified and isolated.

The following examples are offered by way of illustration and not by way of limitation.

EXPERIMENTAL

EXAMPLE 1 cDNA Cloning

Total RNA was isolated from corn tissues with TRIzol Reagent (Life Technology, Inc. Gaithersburg, Md.) using a modification of the guanidine isothiocyanate/acid-phenol procedure described by Chomozynski and Sacchi (Chomczynski et al. (1987) *Anal. Biochem.* 162:156). In brief, plant tissue samples were pulverized in liquid nitrogen before the addition of the TRIzol Reagent, and then were further homogenized with a mortar and pestle. Addition of chloroform by centrifugation was conducted for separation of an aqueous phase and an organic phase. The total RNA was recovered by precipitation with isopropyl alcohol from the aqueous phase.

The selection of poly(A)+RNA from total RNA was performed using PolyATract system (Promega Corporation, Madison, Wis.). In brief, biotinylated oligo (dT) primers were used to hybridize to the 3' poly(A) tails on mRNA. The hybrids were captured using streptavidin coupled to paramagnetic particles and a magnetic separation stand. The mRNA was washed at high stringent condition and cluted by Rnase-free deionized water.

Synthesis of the cDNA was performed and unidirectional cDNA libraries were constructed using the SuperScript Plasmid System (Life Technology, Inc., Gaithersburg, Md.). First strand of CDNA was synthesized by priming an oligo(dT) primer containing a Not I site. The reaction was catalyzed by SuperScript Reverse Transcriptase II at 45° C. The second strand of cDNA was labeled with $\alpha$-$^{32}$P-dCTP and portions of the molecules smaller than 500 base pairs and unligated adapters were removed by Sephacryl-S400 chromatography. The selected cDNA molecules were ligated into pSPORT1 reference vector between the Not I and Sal I sites.

Individual colonies were picked and DNA was prepared either by PCR with M13 forward primers and M13 reverse primers, or by plasmid miniprep isolation. All the cDNA clones were sequenced using M13 reverse primers.

Two maize homologues for RPA large subunit (ZmRPALSH) have been isolated. The genes map to two different chromosomes as shown below in Table 1. The amino acid and nucleotide sequences for the two homologues are set forth in SEQ ID NOs: 1–4.

TABLE 1

Maize RPA Large Subunit Genes Map to Two Different Chromosomes

| Clone ID | Chromosome No. | Homologue |
|---|---|---|
| CBPBS68 | c9 | ZmRPALSH1 |
| CCRBJ83 | c9 | ZmRPALSH1 |
| CDPGS47 | c9 | ZmRPALSH1 |
| CHCLE65 | c9 | ZmRPALSH1 |
| CJLPL35 | c9 | ZmRPALSH1 |
| COMGE67 | c9 | ZmRPALSH1 |
| CBAAK06 | c9 | ZmRPALSH2 |
| CDPGS46 | c9 | ZmRPALSH2 |
| CERAG93 | c9 | ZmRPALSH2 |
| COMFY67 | c9 | ZmRPALSH2 |

Ten ESTs, which form two different contigs for maize RPA large subunit, were used as probes for mapping experiments. Each contig represents one maize homologue for RPALS.

Seven maize homologues for RPA middle subunit (ZmRPAMSH) have been isolated. The genes map to chromosomes 5 as shown below in Table 2. The nucleotide and amino acid sequences of the seven homologues are set forth in SEQ ID NOs: 11–22.

TABLE 2

Maize Homologues of Eukaryotic Replication Protein A Middle Subunit

| Clone ID | Homologue | Library | Map Position |
|---|---|---|---|
| CCRBK63 | ZmRPAMSH-1 | P0026 | C5 |
| CGEUZ26 | ZmRPAMSH-2 | P0002 | TBD |
| CGEVJ74 | ZmRPAMSH-3 | P0002 | TBD |
| CHSBX01 | ZmRPABMS-4 | P0118 | C5 |
| CIMME04 | ZmRPAMSH-5 | P0114 | C5 |
| CRTBB78 | ZmRPAMSH-6 | P0041 | C5 |
| CVRAP89 | ZmRPAMSH-7 | P0057 | C5 |

TBD = To be determined.

EXAMPLE 2

Transformation and Regeneration of Transgenic Plants

Immature maize embryos from greenhouse donor plants are bombarded with a plasmid containing the RPA antisense sequence of the invention operably linked to a pathogen-inducible promoter (FIG. 2) plus a plasmid containing the selectable marker gene PAT (Wohlleben et al. (1988) *Gene* 70:25–37) that confers resistance to the herbicide Bialaphos. Transformation is performed as follows. All media recipes are in the Appendix.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the RPA sequence of the invention operably linked to a ubiquitin promoter is made. This plasmid DNA plus plasmid DNA containing a PAT selectable marker is precipitated onto 1.1 $\mu$m (average diameter) tungsten pellets using a CaCl$_2$ precipitation procedure as follows.

100 μl prepared tungsten particles in water
10 μl (1 μg) DNA in TrisEDTA buffer (1 μg total)
100 μl 2.5 M CaCl$_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for expression of the RPA gene of interest.

APPENDIX

272 V

| Ingredient | Amount | Unit |
| --- | --- | --- |
| D-I H$_2$O | 950.000 | Ml |
| MS Salts (GIBCO 11117-074) | 4.300 | G |
| Myo-Inositol | 0.100 | G |
| MS Vitamins Stock Solution ## | 5.000 | Ml |
| Sucrose | 40.000 | G |
| Bacto-Agar @ | 6.000 | G |

Directions
@=Add after bringing up to volume
Dissolve ingredients in polished D-I H$_2$O in sequence
Adjust to pH 5.6
Bring up to volume with polished D-I H$_2$O after adjusting pH
Sterilize and cool to 60° C.
=Dissolve 0.100 g of Nicotinic Acid; 0.020 g of Thiamine.HCL; 0.100 g of Pyridoxine.HCL; and 0.400 g of Glycine in 875.00 ml of polished D-I H$_2$O in sequence. Bring up to volume with polished D-I H$_2$O. Make in 400 ml portions. Thiamine.HCL & Pyridoxine.HCL are in Dark Desiccator. Store for one month, unless contamination or precipitation occurs, then make fresh stock.
Total Volume (L)=1.00

288 J

| Ingredient | Amount | Unit |
| --- | --- | --- |
| D-I H$_2$O | 950.000 | Ml |
| MS Salts | 4.300 | G |
| Myo-Inositol | 0.100 | G |
| MS Vitamins Stock Solution ## | 5.000 | Ml |
| Zeatin .5 mg/ml | 1.000 | Ml |
| Sucrose | 60.000 | G |
| Gelrite @ | 3.000 | G |
| Indoleacetic Acid 0.5 mg/ml # | 2.000 | Ml |
| 0.1 mM Abscisic Acid | 1.000 | Ml |
| Bialaphos 1 mg/ml # | 3.000 | Ml |

Directions
@=Add after bringing up to volume
Dissolve ingredients in polished D-I H$_2$O in sequence
Adjust to pH 5.6
Bring up to volume with polished D-I H$_2$O after adjusting pH
Sterilize and cool to 60° C.
Add 3.5 g/L of Gelrite for cell biology.
=Dissolve 0.100 g of Nicotinic Acid; 0.020 g of Thiamine.HCL; 0.100 g of Pyridoxine.HCL; and 0.400 g of Glycine in 875.00 ml of polished D-I H$_2$O in sequence. Bring up to volume with polished D-I H$_2$O. Make in 400 ml portions. Thiamine.HCL & Pyridoxine.HCL are in Dark Desiccator. Store for one month, unless contamination or precipitation occurs, then make fresh stock.
Total Volume (L)=1.00

560 R

| Ingredient | Amount | Unit |
| --- | --- | --- |
| D-I Water, Filtered | 950.000 | Ml |
| CHU (N6) Basal Salts (SIGMA C-1416) | 4.000 | G |
| Eriksson's Vitamin Mix (1000X SIGMA-1511) | 1.000 | Ml |
| Thiamine HCL 0.4 mg/ml | 1.250 | Ml |
| Sucrose | 30.000 | G |
| 2,4-D 0.5 mg/ml | 4.000 | Ml |
| Gelrite @ | 3.000 | G |
| Silver Nitrate 2 mg/ml # | 0.425 | Ml |
| Bialaphos 1 mg/ml # | 3.000 | Ml |

Directions
@=Add after bringing up to volume
=Add after sterilizing and cooling to temp.
Dissolve ingredients in D-I H$_2$O in sequence
Adjust to pH 5.8 with KOH
Bring up to volume with D-I H$_2$O
Sterilize and cool to room temp.
Total Volume (L)=1.00

560 Y

| Ingredient | Amount | Unit |
| --- | --- | --- |
| D-I Water, Filtered | 950.000 | Ml |
| CHU (N6) Basal Salts (SIGMA C-1416) | 4.000 | G |
| Eriksson's Vitamin Mix (1000X SIGMA-1511 | 1.000 | Ml |

-continued

560 Y

| Ingredient | Amount | Unit |
|---|---|---|
| Thiamine HCL 0.4 mg/ml | 1.250 | Ml |
| Sucrose | 120.000 | G |
| 2,4-D 0.5 mg/ml | 2.000 | Ml |
| L-Proline | 2.880 | G |
| Gelrite @ | 2.000 | G |
| Silver Nitrate 2 mg/ml # | 4.250 | Ml |

Directions
@=Add after bringing up to volume
=Add after sterilizing and cooling to temp.
Dissolve ingredients in D-I H$_2$O in sequence
Adjust to pH 5.8 with KOH Bring up to volume with D-I H$_2$O
Sterilize and cool to room temp.
 Autoclave less time because of increased sucrose
Total Volume (L)=1.00

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated nucleotide sequence selected from the group consisting of:
   a) nucleotide sequence set forth in SEQ ID NO: 1 or SEQ ID NO: 3;
   b) a nucleotide sequence that encodes an amino acid sequence set forth in SEQ ID NO: 2 or SEQ ID NO: 4; and,
   c) an antisense nucleotide sequence corresponding to a nucleotide sequence of a) or b).

2. A DNA construct comprising a nucleotide sequence according to claim 1 wherein said nucleotide sequence is operably linked to a promoter that drives expression in a plant cell.

3. The DNA construct of claim 2, wherein said promoter is a tissue-preferred promoter.

4. The DNA construct of claim 3, wherein said promoter is a pathogen-inducible promoter.

5. The DNA construct of claim 4, wherein said nucleotide sequence is an antisense sequence.

6. The DNA construct of claim 2, wherein said promoter is a constitutive promoter.

7. A method for enhancing homologous recombination in a plant cell, said method comprising transforming said plant cell with at least one nucleotide sequence operably linked to a heterologous promoter that drives expression in a plant cell, wherein said nucleotide sequence is selected from the group consisting of:
  a) a nucleotide sequence set forth in SEQ ID NO: 1 or SEQ ID NO: 3; and,
  b) a nucleotide sequence that encodes an amino acid sequence set forth in SEQ ID NO: 2 or SEQ ID NO: 4.

8. The method of claim 7, wherein said promoter is a constitutive promoter.

9. The method of claim 8, wherein said promoter is an ubiquitin promoter.

10. A method for increasing pathogen resistance in a plant cell, said method comprising transforming said plant cell with at least one nucleotide sequence operably linked to a pathogen-inducible promoter, wherein said nucleotide sequence is selected from the group consisting of:
  a) an antisense nucleotide sequence corresponding to the nucleotide sequence set forth in SEQ ID NO: 1 or SEQ ID NO: 3; and
  b) an antisense nucleotide sequence corresponding to the nucleotide sequence that encodes an amino acid sequence set forth in SEQ ID NO: 2 or SEQ ID NO: 4.

11. A transformed plant cell having stably incorporated into its genome at least one nucleotide sequence, said nucleotide sequence operably linked to a heterologous promoter that drives expression in a plant cell, wherein said nucleotide sequence is selected from the group consisting of:
  a) a nucleotide sequence set forth in SEQ ID NO: 1 or SEQ ID NO: 3;
  b) a nucleotide sequence that encodes an amino acid sequence set forth in SEQ ID NO: 2 or SEQ ID NO: 4; and,
  c) an antisense nucleotide sequence corresponding to a nucleotide sequence of a) or b).

12. A transformed plant having stably incorporated into its genome at least one nucleotide sequence, said nucleotide sequence operably linked to a heterologous promoter that drives expression in a plant cell, wherein said nucleotide sequence is selected from the group consisting of:
  a) a nucleotide sequence set forth in SEQ ID NO: 1 or SEQ ID NO: 3;
  b) a nucleotide sequence that encodes an amino acid sequence set forth in SEQ ID NO: 2 or SEQ ID NO: 4; and,
  c) an antisense nucleotide sequence corresponding to a nucleotide sequence of a) or b).

13. Seed of the plant of claim 12.

14. The plant of claim 12, wherein said plant is a monocot.

15. The plant of claim 14, wherein said monocot is maize, wheat, rice, barley, sorghum, or rye.

16. The plant of claim 12, wherein said plant is a dicot.

17. The plant of claim 16, wherein said dicot is selected from the group consisting of soybean, canola, sunflower, alfalfa, or safflower.

18. Seed of the plant of claim 16.

19. A method for modulating DNA metabolism in a plant cell, said method comprising transforming said plant cell with at least one nucleotide sequence operably linked to a promoter, wherein said nucleotide sequence is selected from the group consisting of:
  a) a nucleotide sequence set forth in SEQ ID NO: 1 and SEQ ID NO: 3;
  b) a nucleotide sequence that encodes an amino acid sequence set forth in SEQ ID NO: 2 and SEQ ID NO: 4; and,
  c) an antisense nucleotide sequence corresponding to a nucleotide sequence of a) or b).

20. A method for influencing cell cycle in a plant cell, said method comprising transforming said plant cell with at least one nucleotide sequence operably linked to a promoter, wherein said nucleotide sequence is selected from the group consisting of:
  a) a nucleotide sequence set forth in SEQ ID NO: 1 and SEQ ID NO: 3;
  b) a nucleotide sequence that encodes an amino acid sequence set forth in SEQ ID NO: 2 and SEQ ID NO: 4; and,
  c) an antisense nucleotide sequence corresponding to a nucleotide sequence of a) or b).

21. A nucleotide sequence having at least 95% identity to a full-length nucleotide sequence set forth in SEQ ID NO: 1 or SEQ ID NO: 3, wherein said nucleotide sequence encodes a polypeptide having replication protein A activity.

22. A method for enhancing homologous recombination in a plant cell, said method comprising transforming said plant cell with at least one nucleotide sequence operably linked to a heterologous promoter that drives expression in a plant cell, wherein said nucleotide sequence is selected from the group consisting of:
  a) a nucleotide sequence having at least 95% identity to a full-length nucleotide sequence set forth in SEQ ID NO: 1 or SEQ ID NO: 3 wherein said nucleotide sequence encodes a polypeptide having replication protein A activity; and,
  b) a nucleotide sequence having at least 95% identity to a full-length nucleotide sequence that encodes an amino acid sequence set forth in SEQ ID NO: 2 or SEQ ID NO: 4 wherein said nucleotide sequence encodes a polypeptide having replication protein A activity.

23. A method for increasing pathogen resistance in a plant cell, said method comprising transforming said plant cell with at least one nucleotide sequence operably linked to a pathogen-inducible promoter, wherein said nucleotide sequence is selected from the group consisting of:
  a) an antisense nucleotide sequence corresponding to a nucleotide sequence having at least 95% identity to a nucleotide sequence set forth in SEQ ID NO: 1 or SEQ ID NO: 3;
  b) an antisense nucleotide sequence corresponding to a nucleotide sequence having at least 95% identity to a nucleotide sequence that encodes an amino acid sequence set forth in SEQ ID NO: 2 or SEQ ID NO: 4.

24. A transformed plant cell having stably incorporated into its genome at least one nucleotide sequence, said nucleotide sequence operably linked to a heterologous promoter that drives expression in a plant cell, wherein said nucleotide sequence is selected from the group consisting of:
  a) a nucleotide sequence having at least 95% identity to a full-length nucleotide sequence set forth in SEQ ID NO: 1 or SEQ ID NO: 3, wherein said nucleotide sequence encodes a polypeptide having replication protein A activity;

b) a nucleotide sequence having at least 95% identity to a full-length nucleotide sequence that encodes an amino acid sequence set forth in SEQ ID NO: 2 or SEQ ID NO: 4, wherein said nucleotide sequence encodes a polypeptide having replication protein A activity; and, c) an antisense nucleotide sequence corresponding to a nucleotide sequence of a) or b).

25. A transformed plant having stably incorporated into its genome at least one nucleotide sequence, said nucleotide sequence operably linked to a heterologous promoter that drives expression in a plant cell, wherein said nucleotide sequence is selected from the group consisting of:

a) a nucleotide sequence having at least 95% identity to a full-length nucleotide sequence set forth in SEQ ID NO: 1 or SEQ ID NO: 3, wherein said nucleotide sequence encodes a polypeptide having replication protein A activity;

b) a nucleotide sequence having at least 95% identity to a full-length nucleotide sequence that encodes an amino acid sequence set forth in SEQ ID NO: 2 or SEQ ID NO: 4, wherein said nucleotide sequence encodes a polypeptide having replication protein A activity; and, c) an antisense nucleotide sequence corresponding to a nucleotide sequence of a) or b).

26. Seed of the plant of claim 25.

* * * * *

SEQUENCE LISTING

```
<160> NUMBER OF SEQ ID NOS: 22

<210> SEQ ID NO 1
<211> LENGTH: 2497
<212> TYPE: DNA
<213> ORGANISM: Zea Mays
<220> FEATURE:
<221> NAME/KEY: CDS
<222> LOCATION: (157)...(2025)
<223> OTHER INFORMATION: Coding sequence for the Maize RPA Large Subunit
      Homologue-1
<220> FEATURE:
<221> NAME/KEY: misc_feature
<222> LOCATION: (0)...(0)
<223> OTHER INFORMATION: Maize RPA Large subunit Homologue-1

<400> SEQUENCE: 1
ccttatcata ttataagcgc gcgtagcctt ggcagctcga cgcatcttcg cctccgctca      60
acgctcgccc acgcccccag ccccaccga tccacgagaa accttctcgc ctccgcggga     120
cgattcgcca gggagagcaa aggtagcaga ggcgcc atg gac gct gcc aag tcg     174
                                        Met Asp Ala Ala Lys Ser
                                         1               5 gtg acg ccg ggc gcc gtg tcc tac atc ctg gcg cac ccg tct acg ggc      222
Val Thr Pro Gly Ala Val Ser Tyr Ile Leu Ala His Pro Ser Thr Gly
             10                  15                  20 tcc gat ggc gcc gtg tcg gat ctc gtc gtt cag gtc ctc gat ctc aag      270
Ser Asp Gly Ala Val Ser Asp Leu Val Val Gln Val Leu Asp Leu Lys
         25                  30                  35 tcc atc ggc atg ggc agc cgg ttc agt ttc acg gca tcc gat ggg aac      318
Ser Ile Gly Met Gly Ser Arg Phe Ser Phe Thr Ala Ser Asp Gly Asn
     40                  45                  50 gac aaa atc aag gcg atg ctc ccc act tac ttt gcg tcg gag gtc cac      366
Asp Lys Ile Lys Ala Met Leu Pro Thr Tyr Phe Ala Ser Glu Val His
 55                  60                  65                  70 tcc ggc aat ctg aag aat ttc ggt ctc atc cgc atc ctc gac tac act      414
Ser Gly Asn Leu Lys Asn Phe Gly Leu Ile Arg Ile Leu Asp Tyr Thr
                 75                  80                  85 tgc aac tcc gtc aaa ggc aac gct gac aaa gtc ctg att gtc gtc aaa      462
Cys Asn Ser Val Lys Gly Asn Ala Asp Lys Val Leu Ile Val Val Lys
             90                  95                 100 tgc gag act gtg tgc gaa gcg ctc gac gcc gag atc aac ggc gag gcc      510
Cys Glu Thr Val Cys Glu Ala Leu Asp Ala Glu Ile Asn Gly Glu Ala
        105                 110                 115
```

-continued

| | |
|---|---|
| aag aaa gag gat cct cca att gtg ctg aag cct aaa gac gaa ggc tca<br>Lys Lys Glu Asp Pro Pro Ile Val Leu Lys Pro Lys Asp Glu Gly Ser<br>120                        125                        130 | 558 |
| gtc gtg gct gag gaa aca aat tct ccc cca ctc gtg atg aag cct aag<br>Val Val Ala Glu Glu Thr Asn Ser Pro Pro Leu Val Met Lys Pro Lys<br>135                        140                        145                        150 | 606 |
| caa gag gtg aag tcc gcg tcc cag atc gtg act gag cag cgt gga aat<br>Gln Glu Val Lys Ser Ala Ser Gln Ile Val Thr Glu Gln Arg Gly Asn<br>                        155                        160                        165 | 654 |
| gct gct cct gcc acg cgc ctt tcc atg aca agg agg gtc cat ccc ttg<br>Ala Ala Pro Ala Thr Arg Leu Ser Met Thr Arg Arg Val His Pro Leu<br>                  170                        175                        180 | 702 |
| atc act ctg aac ccc tac cag ggt aac tgg gtc att aag gtg cgg gtc<br>Ile Thr Leu Asn Pro Tyr Gln Gly Asn Trp Val Ile Lys Val Arg Val<br>                  185                        190                        195 | 750 |
| acg agc aaa ggc aat ctg aga acc tac agg aat gct cgt gga gaa ggc<br>Thr Ser Lys Gly Asn Leu Arg Thr Tyr Arg Asn Ala Arg Gly Glu Gly<br>200                        205                        210 | 798 |
| tgc gtc ttc aac gta gag ctt act gat gag gat ggc acc cag atc cag<br>Cys Val Phe Asn Val Glu Leu Thr Asp Glu Asp Gly Thr Gln Ile Gln<br>215                        220                        225                        230 | 846 |
| gcc acc atg ttt aac gag gct gca aag aag ttc tat cca att ttt gag<br>Ala Thr Met Phe Asn Glu Ala Ala Lys Lys Phe Tyr Pro Ile Phe Glu<br>                  235                        240                        245 | 894 |
| ctg gga aag gtc tat tat gtc tca aaa gga tct ctt aga att gcc aac<br>Leu Gly Lys Val Tyr Tyr Val Ser Lys Gly Ser Leu Arg Ile Ala Asn<br>                  250                        255                        260 | 942 |
| aag cag ttc aag aca gtc aaa aat gac tat gag ttg tca cta aac gag<br>Lys Gln Phe Lys Thr Val Lys Asn Asp Tyr Glu Leu Ser Leu Asn Glu<br>                  265                        270                        275 | 990 |
| aat gct att gtt gaa gaa gca gag ggg gag act ttc ctt cca cca gtg<br>Asn Ala Ile Val Glu Glu Ala Glu Gly Glu Thr Phe Leu Pro Pro Val<br>280                        285                        290 | 1038 |
| caa tac aac ctt gtc aag att gat cag cta gga cca tac gtc ggt ggc<br>Gln Tyr Asn Leu Val Lys Ile Asp Gln Leu Gly Pro Tyr Val Gly Gly<br>295                        300                        305                        310 | 1086 |
| agg gag ctt gta gat att gtt ggt gtg gtt cag agc gta tct ccc aca<br>Arg Glu Leu Val Asp Ile Val Gly Val Val Gln Ser Val Ser Pro Thr<br>                  315                        320                        325 | 1134 |
| ctc agt gtt agg aga aag att gac aac gag aca ata ccg aag cgt gac<br>Leu Ser Val Arg Arg Lys Ile Asp Asn Glu Thr Ile Pro Lys Arg Asp<br>                  330                        335                        340 | 1182 |
| att gtt gta gca gac gac tct ggc aaa act gtt act att tct ctc tgg<br>Ile Val Val Ala Asp Asp Ser Gly Lys Thr Val Thr Ile Ser Leu Trp<br>                  345                        350                        355 | 1230 |
| aat gat ctt gct act acg act ggc caa gag ctt ttg gac atg gtt gac<br>Asn Asp Leu Ala Thr Thr Thr Gly Gln Glu Leu Leu Asp Met Val Asp<br>360                        365                        370 | 1278 |
| agt tcg cct gtt gtt gcg ata aag agc cta aaa gta tct gac ttc caa<br>Ser Ser Pro Val Val Ala Ile Lys Ser Leu Lys Val Ser Asp Phe Gln<br>375                        380                        385                        390 | 1326 |
| ggc gtg tct ctt tca act att ggc aga agt act ctc gag att aat cct<br>Gly Val Ser Leu Ser Thr Ile Gly Arg Ser Thr Leu Glu Ile Asn Pro<br>                  395                        400                        405 | 1374 |
| gac ctg cct gag gct aag aat ctt aag tcc tgg tat gac tct gaa ggc<br>Asp Leu Pro Glu Ala Lys Asn Leu Lys Ser Trp Tyr Asp Ser Glu Gly<br>                  410                        415                        420 | 1422 |
| aaa gat act tca ctg gca cca atc agt gca gaa gcg ggt gcc aca cgc<br>Lys Asp Thr Ser Leu Ala Pro Ile Ser Ala Glu Ala Gly Ala Thr Arg | 1470 |

-continued

```
              425                 430                 435
gct ggt ggt ttc aag tcc atg tat tct gat aga gtt ttt ctg tct cac      1518
Ala Gly Gly Phe Lys Ser Met Tyr Ser Asp Arg Val Phe Leu Ser His
    440                 445                 450 atc acc agt gat cct gct atg ggc cag gaa aag cct gtt ttc ttc agt      1566
Ile Thr Ser Asp Pro Ala Met Gly Gln Glu Lys Pro Val Phe Phe Ser
455                 460                 465                 470 ctg tac gcc atc ata agc cac atc aag cct gat cag aat atg tgg tac      1614
Leu Tyr Ala Ile Ile Ser His Ile Lys Pro Asp Gln Asn Met Trp Tyr
                475                 480                 485 cgt gct tgc acg acc tgt aac aag aag gtg act gaa gct ttt ggg tct      1662
Arg Ala Cys Thr Thr Cys Asn Lys Lys Val Thr Glu Ala Phe Gly Ser
            490                 495                 500 gga tac tgg tgc gag ggg tgc caa aag aat gac tct gag tgc tcg ctg      1710
Gly Tyr Trp Cys Glu Gly Cys Gln Lys Asn Asp Ser Glu Cys Ser Leu
        505                 510                 515 agg tac atc atg gtg atc aag ctc tcc gat ccc act ggt gag gct tgg      1758
Arg Tyr Ile Met Val Ile Lys Leu Ser Asp Pro Thr Gly Glu Ala Trp
    520                 525                 530 gtg tcc gtg ttc aac gag cat gcg gag aag atc att ggc tgc agc gcc      1806
Val Ser Val Phe Asn Glu His Ala Glu Lys Ile Ile Gly Cys Ser Ala
535                 540                 545                 550 gac gag ctt gat cgg atc agg aaa gag gag ggg gac gac agc tac gtt      1854
Asp Glu Leu Asp Arg Ile Arg Lys Glu Glu Gly Asp Asp Ser Tyr Val
                555                 560                 565 ctc aag ctc aag gaa gcc acc tgg gtt cct cac ctg ttc cgc gtc agc      1902
Leu Lys Leu Lys Glu Ala Thr Trp Val Pro His Leu Phe Arg Val Ser
            570                 575                 580 gtc aca cag cat gaa tac atg aac gag aag agg cag aga atc acc gtg      1950
Val Thr Gln His Glu Tyr Met Asn Glu Lys Arg Gln Arg Ile Thr Val
        585                 590                 595 agg ggt gaa gca ccg gtc gac ttc gca gct gag tcc aag tac ttg ctt      1998
Arg Gly Glu Ala Pro Val Asp Phe Ala Ala Glu Ser Lys Tyr Leu Leu
    600                 605                 610 gaa gag atc gcg aag ctc acc gct tgc tagaagacgc agtctttctg            2045
Glu Glu Ile Ala Lys Leu Thr Ala Cys
615                 620 gtggttcttg aaggactggc ccccgatatg tctccctctc agttttttctt ttgagctcca   2105 gtaacttgat tactgttctg tgtgttgctc tcactgggtt ttagcacttc tgtaaggtat    2165
atgtagatgc tagtttacct tggtgtcaag gaacagatgc tattataagc cttgcaaaat    2225
tgcagttcca attccgtgta tctgcaacct tgagcaaata gggaaagatt atgagtacta    2285
attgatgatg ttaggtcgct gcagctaaca agtgtttggt ttttagtgac tactgtttag    2345
tccctatatt ttattctatt ttagtattta aggttgcgtt tggttgcgtc gactagacat    2405
gttgtgcgtg tccgatgagt ctattattga agcacaaaat tgggaataaa aaaaaaaaa    2465 aaaaaaaaaa aaaaaaaaa aaaaaaaaa aa                                   2497
```

<210> SEQ ID NO 2
<211> LENGTH: 623
<212> TYPE: PRT
<213> ORGANISM: Zea Mays

<400> SEQUENCE: 2

```
Met Asp Ala Ala Lys Ser Val Thr Pro Gly Ala Val Ser Tyr Ile Leu
1               5                   10                  15

Ala His Pro Ser Thr Gly Ser Asp Gly Ala Val Ser Asp Leu Val Val
            20                  25                  30
```

-continued

```
Gln Val Leu Asp Leu Lys Ser Ile Gly Met Gly Ser Arg Phe Ser Phe
             35                  40                  45

Thr Ala Ser Asp Gly Asn Asp Lys Ile Lys Ala Met Leu Pro Thr Tyr
     50                  55                  60

Phe Ala Ser Glu Val His Ser Gly Asn Leu Lys Asn Phe Gly Leu Ile
 65                  70                  75                  80

Arg Ile Leu Asp Tyr Thr Cys Asn Ser Val Lys Gly Asn Ala Asp Lys
                 85                  90                  95

Val Leu Ile Val Val Lys Cys Glu Thr Val Cys Glu Ala Leu Asp Ala
            100                 105                 110

Glu Ile Asn Gly Glu Ala Lys Lys Glu Asp Pro Pro Ile Val Leu Lys
            115                 120                 125

Pro Lys Asp Glu Gly Ser Val Val Ala Glu Glu Thr Asn Ser Pro Pro
    130                 135                 140

Leu Val Met Lys Pro Lys Gln Glu Val Lys Ser Ala Ser Gln Ile Val
145                 150                 155                 160

Thr Glu Gln Arg Gly Asn Ala Ala Pro Ala Thr Arg Leu Ser Met Thr
                165                 170                 175

Arg Arg Val His Pro Leu Ile Thr Leu Asn Pro Tyr Gln Gly Asn Trp
            180                 185                 190

Val Ile Lys Val Arg Val Thr Ser Lys Gly Asn Leu Arg Thr Tyr Arg
        195                 200                 205

Asn Ala Arg Gly Glu Gly Cys Val Phe Asn Val Glu Leu Thr Asp Glu
    210                 215                 220

Asp Gly Thr Gln Ile Gln Ala Thr Met Phe Asn Glu Ala Ala Lys Lys
225                 230                 235                 240

Phe Tyr Pro Ile Phe Glu Leu Gly Lys Val Tyr Tyr Val Ser Lys Gly
                245                 250                 255

Ser Leu Arg Ile Ala Asn Lys Gln Phe Lys Thr Val Lys Asn Asp Tyr
            260                 265                 270

Glu Leu Ser Leu Asn Glu Asn Ala Ile Val Glu Glu Ala Glu Gly Glu
        275                 280                 285

Thr Phe Leu Pro Pro Val Gln Tyr Asn Leu Val Lys Ile Asp Gln Leu
    290                 295                 300

Gly Pro Tyr Val Gly Gly Arg Glu Leu Val Asp Ile Val Gly Val Val
305                 310                 315                 320

Gln Ser Val Ser Pro Thr Leu Ser Val Arg Arg Lys Ile Asp Asn Glu
                325                 330                 335

Thr Ile Pro Lys Arg Asp Ile Val Ala Asp Asp Ser Gly Lys Thr
            340                 345                 350

Val Thr Ile Ser Leu Trp Asn Asp Leu Ala Thr Thr Thr Gly Gln Glu
        355                 360                 365

Leu Leu Asp Met Val Asp Ser Ser Pro Val Val Ala Ile Lys Ser Leu
    370                 375                 380

Lys Val Ser Asp Phe Gln Gly Val Ser Leu Ser Thr Ile Gly Arg Ser
385                 390                 395                 400

Thr Leu Glu Ile Asn Pro Asp Leu Pro Glu Ala Lys Asn Leu Lys Ser
                405                 410                 415

Trp Tyr Asp Ser Glu Gly Lys Asp Thr Ser Leu Ala Pro Ile Ser Ala
            420                 425                 430

Glu Ala Gly Ala Thr Arg Ala Gly Gly Phe Lys Ser Met Tyr Ser Asp
        435                 440                 445
```

```
Arg Val Phe Leu Ser His Ile Thr Ser Asp Pro Ala Met Gly Gln Glu
    450                 455                 460

Lys Pro Val Phe Phe Ser Leu Tyr Ala Ile Ile Ser His Ile Lys Pro
465                 470                 475                 480

Asp Gln Asn Met Trp Tyr Arg Ala Cys Thr Thr Cys Asn Lys Lys Val
                    485                 490                 495

Thr Glu Ala Phe Gly Ser Gly Tyr Trp Cys Glu Gly Cys Gln Lys Asn
                500                 505                 510

Asp Ser Glu Cys Ser Leu Arg Tyr Ile Met Val Ile Lys Leu Ser Asp
            515                 520                 525

Pro Thr Gly Glu Ala Trp Val Ser Val Phe Asn Glu His Ala Glu Lys
        530                 535                 540

Ile Ile Gly Cys Ser Ala Asp Glu Leu Asp Arg Ile Arg Lys Glu Glu
545                 550                 555                 560

Gly Asp Asp Ser Tyr Val Leu Lys Leu Lys Glu Ala Thr Trp Val Pro
                565                 570                 575

His Leu Phe Arg Val Ser Val Thr Gln His Glu Tyr Met Asn Glu Lys
                580                 585                 590

Arg Gln Arg Ile Thr Val Arg Gly Glu Ala Pro Val Asp Phe Ala Ala
            595                 600                 605

Glu Ser Lys Tyr Leu Leu Glu Glu Ile Ala Lys Leu Thr Ala Cys
        610                 615                 620

<210> SEQ ID NO 3
<211> LENGTH: 2202
<212> TYPE: DNA
<213> ORGANISM: Zea Mays
<220> FEATURE:
<221> NAME/KEY: CDS
<222> LOCATION: (91)...(1941)
<223> OTHER INFORMATION: Coding Region for Maize RPA Large Subunit
      Homologue-2
<220> FEATURE:
<221> NAME/KEY: misc_feature
<222> LOCATION: (0)...(0)
<223> OTHER INFORMATION: Maize RPA Large Subunit Homologue-2

<400> SEQUENCE: 3
```

| | | |
|---|---|---|
| acgttccccc cacgccccaa cctatccacg cgaaaccttc ttttccccgg gagacgattc | | 60 |
| gtcagggaga ggaaagaggc aagagggggcc atg gac gct gcc aag ttg gtg acg<br>                                              Met Asp Ala Ala Lys Leu Val Thr<br>                                                1          5 | | 114 |
| ccg gtc gct gtg tct cac att ctg gcg cac ccg tcg gcg ggc tcc gac<br>Pro Val Ala Val Ser His Ile Leu Ala His Pro Ser Ala Gly Ser Asp<br>     10                 15                 20 | | 162 |
| ggc gca gtg acc gat ctc gtc gtt cag gtc ctc gac ctg aag tcc gtc<br>Gly Ala Val Thr Asp Leu Val Val Gln Val Leu Asp Leu Lys Ser Val<br> 25                   30                 35                 40 | | 210 |
| ggc acg ggc agc cgg ttc agt ttc aca gca act gac ggg aag gat aag<br>Gly Thr Gly Ser Arg Phe Ser Phe Thr Ala Thr Asp Gly Lys Asp Lys<br>               45                 50                 55 | | 258 |
| atc aag gcg atg ctt ccc acc aac ttc ggg tcg gag gtc cgc tct ggc<br>Ile Lys Ala Met Leu Pro Thr Asn Phe Gly Ser Glu Val Arg Ser Gly<br>           60                 65                 70 | | 306 |
| aac ctg aag aac ctc ggc ctc atc cgc atc atc gac tac act tgc aac<br>Asn Leu Lys Asn Leu Gly Leu Ile Arg Ile Ile Asp Tyr Thr Cys Asn<br>       75                 80                 85 | | 354 |
| gtc gtc aaa ggc aaa gat gac aaa gtc ttg gtt gtc atc aaa tgc gag<br>Val Val Lys Gly Lys Asp Asp Lys Val Leu Val Val Ile Lys Cys Glu<br>     90                 95                 100 | | 402 |

```
ctt gtg tgc caa gcg ctt gac gcc gag atc aac ggc gag gcc aaa aaa      450
Leu Val Cys Gln Ala Leu Asp Ala Glu Ile Asn Gly Glu Ala Lys Lys
105                 110                 115                 120 gag gag cct cca att gtg ctg aag cct aag gac gaa tgc gtg ggc gtg      498
Glu Glu Pro Pro Ile Val Leu Lys Pro Lys Asp Glu Cys Val Gly Val
            125                 130                 135 act tcc cca ctc gct atg aag ccc aag cag gag gtg aag tct gcg tcc      546
Thr Ser Pro Leu Ala Met Lys Pro Lys Gln Glu Val Lys Ser Ala Ser
        140                 145                 150 cag atc gtg aat gag cag cgt gga aat act gct cct gtc aag ccc ctt      594
Gln Ile Val Asn Glu Gln Arg Gly Asn Thr Ala Pro Val Lys Pro Leu
    155                 160                 165 tcc atg aca aag agg gtc cat cct ttg atc act ctg aac ccc tac cag      642
Ser Met Thr Lys Arg Val His Pro Leu Ile Thr Leu Asn Pro Tyr Gln
170                 175                 180 ggt aac tgg gtc att aag gtg cgg gtc acg agc aaa ggc aac ctg aga      690
Gly Asn Trp Val Ile Lys Val Arg Val Thr Ser Lys Gly Asn Leu Arg
185                 190                 195                 200 acc tac agg aat gct cgc gga gaa ggc tgt gtc ttc aat gta gag ctc      738
Thr Tyr Arg Asn Ala Arg Gly Glu Gly Cys Val Phe Asn Val Glu Leu
            205                 210                 215 acc gat gag gat ggc acc cag atc caa gcc acc atg ttt aat gac gct      786
Thr Asp Glu Asp Gly Thr Gln Ile Gln Ala Thr Met Phe Asn Asp Ala
        220                 225                 230 gca aag aag ttc tat ccg att ttt gag ctg gga aag gtc tat tat gtc      834
Ala Lys Lys Phe Tyr Pro Ile Phe Glu Leu Gly Lys Val Tyr Tyr Val
    235                 240                 245 tca aaa gga tct ctt aga att gct aac aag cag ttc aag act gtc caa      882
Ser Lys Gly Ser Leu Arg Ile Ala Asn Lys Gln Phe Lys Thr Val Gln
250                 255                 260 aat gac tac gag atg tca cta aac gag aat gct att gtt gaa gaa gca      930
Asn Asp Tyr Glu Met Ser Leu Asn Glu Asn Ala Ile Val Glu Glu Ala
265                 270                 275                 280 gag ggg gag act tgc att ccg caa gtg caa tac aac ctt gtc aag att      978
Glu Gly Glu Thr Cys Ile Pro Gln Val Gln Tyr Asn Leu Val Lys Ile
            285                 290                 295 gat caa cta gga tca tat gtc ggt ggc agg gaa ctt gta gat att gtt     1026
Asp Gln Leu Gly Ser Tyr Val Gly Gly Arg Glu Leu Val Asp Ile Val
        300                 305                 310 ggt gtg gtt cag agc gta tct ccc aca ctc agt gtc agg aga aag att     1074
Gly Val Val Gln Ser Val Ser Pro Thr Leu Ser Val Arg Arg Lys Ile
    315                 320                 325 gac aac gag aca ata ccg aag cgt gac att gtt gtg gcg gat gac tct     1122
Asp Asn Glu Thr Ile Pro Lys Arg Asp Ile Val Val Ala Asp Asp Ser
330                 335                 340 ggc aaa act gtt agt atc tct ctt tgg aat gat ctt gct act acg act     1170
Gly Lys Thr Val Ser Ile Ser Leu Trp Asn Asp Leu Ala Thr Thr Thr
345                 350                 355                 360 ggg caa gag ctt ttg gac atg gct gac agt tcg cct gtt gtt gcg ata     1218
Gly Gln Glu Leu Leu Asp Met Ala Asp Ser Ser Pro Val Val Ala Ile
            365                 370                 375 aag agc cta aaa gtg tct gac ttt caa ggc gtg tct ctt tct act gta     1266
Lys Ser Leu Lys Val Ser Asp Phe Gln Gly Val Ser Leu Ser Thr Val
        380                 385                 390 ggc aaa agt act ctt gcg att aat cct gat cta cac gag gct cag aat     1314
Gly Lys Ser Thr Leu Ala Ile Asn Pro Asp Leu His Glu Ala Gln Asn
    395                 400                 405 ctc aag tca tgg tat gac tct gaa ggc aaa gat act tcg ctg gca cca     1362
Leu Lys Ser Trp Tyr Asp Ser Glu Gly Lys Asp Thr Ser Leu Ala Pro
```

-continued

|     |     |     | 410 |     |     |     |     | 415 |     |     |     |     | 420 |     |     |      |
|-----|-----|-----|-----|-----|-----|-----|-----|-----|-----|-----|-----|-----|-----|-----|-----|------|
| att | ggt | gca | gaa | atg | ggt | gcc | gca | cgg | gcc | ggt | ggc | ttc | aag | tcc | acg | 1410 |
| Ile | Gly | Ala | Glu | Met | Gly | Ala | Ala | Arg | Ala | Gly | Gly | Phe | Lys | Ser | Thr |      |
| 425 |     |     |     |     | 430 |     |     |     |     | 435 |     |     |     |     | 440 |      |

| tat | tct | gat | aga | gtt | ttt | ctg | tct | cac | att | act | agt | gat | cct | gcc | atg | 1458 |
|-----|-----|-----|-----|-----|-----|-----|-----|-----|-----|-----|-----|-----|-----|-----|-----|------|
| Tyr | Ser | Asp | Arg | Val | Phe | Leu | Ser | His | Ile | Thr | Ser | Asp | Pro | Ala | Met |      |
|     |     |     |     | 445 |     |     |     |     | 450 |     |     |     |     | 455 |     |      |

| ggc | cag | gaa | aag | cct | gtt | ttc | ttc | agt | ttg | tat | gcc | acc | ata | agc | cac | 1506 |
|-----|-----|-----|-----|-----|-----|-----|-----|-----|-----|-----|-----|-----|-----|-----|-----|------|
| Gly | Gln | Glu | Lys | Pro | Val | Phe | Phe | Ser | Leu | Tyr | Ala | Thr | Ile | Ser | His |      |
|     |     |     | 460 |     |     |     |     | 465 |     |     |     |     | 470 |     |     |      |

| atc | aag | cct | gac | cag | aac | atg | tgg | tac | cgt | gct | tgc | aag | acc | tgc | aac | 1554 |
|-----|-----|-----|-----|-----|-----|-----|-----|-----|-----|-----|-----|-----|-----|-----|-----|------|
| Ile | Lys | Pro | Asp | Gln | Asn | Met | Trp | Tyr | Arg | Ala | Cys | Lys | Thr | Cys | Asn |      |
|     |     | 475 |     |     |     |     | 480 |     |     |     |     | 485 |     |     |     |      |

| aag | aag | gtg | act | gaa | act | ttt | gga | tct | gga | tac | tgg | tgc | gag | gga | tgc | 1602 |
|-----|-----|-----|-----|-----|-----|-----|-----|-----|-----|-----|-----|-----|-----|-----|-----|------|
| Lys | Lys | Val | Thr | Glu | Thr | Phe | Gly | Ser | Gly | Tyr | Trp | Cys | Glu | Gly | Cys |      |
|     | 490 |     |     |     |     | 495 |     |     |     |     | 500 |     |     |     |     |      |

| caa | aag | aat | gac | tcg | gaa | tgc | tca | ctg | aga | tac | atc | atg | gtc | atc | aag | 1650 |
|-----|-----|-----|-----|-----|-----|-----|-----|-----|-----|-----|-----|-----|-----|-----|-----|------|
| Gln | Lys | Asn | Asp | Ser | Glu | Cys | Ser | Leu | Arg | Tyr | Ile | Met | Val | Ile | Lys |      |
| 505 |     |     |     |     | 510 |     |     |     |     | 515 |     |     |     |     | 520 |      |

| gtc | tcc | gat | cct | act | ggc | gag | gca | tgg | ttc | tct | gtg | ttc | aac | gag | cat | 1698 |
|-----|-----|-----|-----|-----|-----|-----|-----|-----|-----|-----|-----|-----|-----|-----|-----|------|
| Val | Ser | Asp | Pro | Thr | Gly | Glu | Ala | Trp | Phe | Ser | Val | Phe | Asn | Glu | His |      |
|     |     |     |     | 525 |     |     |     |     | 530 |     |     |     |     | 535 |     |      |

| gca | gag | aag | atc | att | ggc | tgc | agc | gcc | gac | gag | ctt | gat | cgg | atc | agg | 1746 |
|-----|-----|-----|-----|-----|-----|-----|-----|-----|-----|-----|-----|-----|-----|-----|-----|------|
| Ala | Glu | Lys | Ile | Ile | Gly | Cys | Ser | Ala | Asp | Glu | Leu | Asp | Arg | Ile | Arg |      |
|     |     | 540 |     |     |     |     | 545 |     |     |     |     | 550 |     |     |     |      |

| aaa | gag | gag | ggg | gac | gac | agt | tat | gtt | ctg | aag | ctc | aag | gaa | gcc | acc | 1794 |
|-----|-----|-----|-----|-----|-----|-----|-----|-----|-----|-----|-----|-----|-----|-----|-----|------|
| Lys | Glu | Glu | Gly | Asp | Asp | Ser | Tyr | Val | Leu | Lys | Leu | Lys | Glu | Ala | Thr |      |
|     | 555 |     |     |     |     | 560 |     |     |     |     | 565 |     |     |     |     |      |

| tgg | gtt | cct | cac | ctg | ttc | cgc | gtc | agc | gtc | aca | cag | cat | gaa | tac | aat | 1842 |
|-----|-----|-----|-----|-----|-----|-----|-----|-----|-----|-----|-----|-----|-----|-----|-----|------|
| Trp | Val | Pro | His | Leu | Phe | Arg | Val | Ser | Val | Thr | Gln | His | Glu | Tyr | Asn |      |
| 570 |     |     |     |     | 575 |     |     |     |     | 580 |     |     |     |     |     |      |

| aac | gag | aaa | agg | cag | aga | atc | act | gtg | agg | agt | gaa | gcg | ccg | gtc | gag | 1890 |
|-----|-----|-----|-----|-----|-----|-----|-----|-----|-----|-----|-----|-----|-----|-----|-----|------|
| Asn | Glu | Lys | Arg | Gln | Arg | Ile | Thr | Val | Arg | Ser | Glu | Ala | Pro | Val | Glu |      |
| 585 |     |     |     |     | 590 |     |     |     |     | 595 |     |     |     |     | 600 |      |

| cac | gca | gct | gaa | tcc | aag | tac | ctg | ctt | gaa | cag | ata | gcg | aag | ctt | act | 1938 |
|-----|-----|-----|-----|-----|-----|-----|-----|-----|-----|-----|-----|-----|-----|-----|-----|------|
| His | Ala | Ala | Glu | Ser | Lys | Tyr | Leu | Leu | Glu | Gln | Ile | Ala | Lys | Leu | Thr |      |
|     |     |     | 605 |     |     |     |     | 610 |     |     |     |     | 615 |     |     |      |

| gct tgatagtaga agatgcaacc ttactgcaaa tagcgaggat tattaggact | 1991 |
|-----|---|
| Ala |   |

| aattgatggt gtcaggtcat tgcggcccta agctttagct ctctatcagc agtcagatgt | 2051 |
| attaccatt ccctgctcta atagtcatct atcagcagtc agatgtattt aaccaaaaaa | 2111 |
| aaaaaaaaaa aaaaaaaaaa aaaaaaaaaa aaaaaaaaaa aaaagggcgg ccgctctaga | 2171 |
| ggatccaagc ttacgtacgc gtgcatgcga c | 2202 |

<210> SEQ ID NO 4
<211> LENGTH: 617
<212> TYPE: PRT
<213> ORGANISM: Zea Mays

<400> SEQUENCE: 4

Met Asp Ala Ala Lys Leu Val Thr Pro Val Ala Val Ser His Ile Leu
1               5                   10                  15

Ala His Pro Ser Ala Gly Ser Asp Gly Ala Val Thr Asp Leu Val Val
                20                  25                  30

Gln Val Leu Asp Leu Lys Ser Val Gly Thr Gly Ser Arg Phe Ser Phe
            35                  40                  45

Thr Ala Thr Asp Gly Lys Asp Lys Ile Lys Ala Met Leu Pro Thr Asn

```
         50                  55                  60
     Phe Gly Ser Glu Val Arg Ser Gly Asn Leu Lys Asn Leu Gly Leu Ile
     65                  70                  75                  80
     Arg Ile Ile Asp Tyr Thr Cys Asn Val Val Lys Gly Lys Asp Asp Lys
                         85                  90                  95
     Val Leu Val Val Ile Lys Cys Glu Leu Val Cys Gln Ala Leu Asp Ala
                     100                 105                 110
     Glu Ile Asn Gly Glu Ala Lys Lys Glu Glu Pro Pro Ile Val Leu Lys
                 115                 120                 125
     Pro Lys Asp Glu Cys Val Gly Val Thr Ser Pro Leu Ala Met Lys Pro
     130                 135                 140
     Lys Gln Glu Val Lys Ser Ala Ser Gln Ile Val Asn Glu Gln Arg Gly
     145                 150                 155                 160
     Asn Thr Ala Pro Val Lys Pro Leu Ser Met Thr Lys Arg Val His Pro
                     165                 170                 175
     Leu Ile Thr Leu Asn Pro Tyr Gln Gly Asn Trp Val Ile Lys Val Arg
                     180                 185                 190
     Val Thr Ser Lys Gly Asn Leu Arg Thr Tyr Arg Asn Ala Arg Gly Glu
                 195                 200                 205
     Gly Cys Val Phe Asn Val Glu Leu Thr Asp Glu Asp Gly Thr Gln Ile
             210                 215                 220
     Gln Ala Thr Met Phe Asn Asp Ala Ala Lys Lys Phe Tyr Pro Ile Phe
     225                 230                 235                 240
     Glu Leu Gly Lys Val Tyr Tyr Val Ser Lys Gly Ser Leu Arg Ile Ala
                     245                 250                 255
     Asn Lys Gln Phe Lys Thr Val Gln Asn Asp Tyr Glu Met Ser Leu Asn
                 260                 265                 270
     Glu Asn Ala Ile Val Glu Glu Ala Gly Glu Thr Cys Ile Pro Gln
                 275                 280                 285
     Val Gln Tyr Asn Leu Val Lys Ile Asp Gln Leu Gly Ser Tyr Val Gly
     290                 295                 300
     Gly Arg Glu Leu Val Asp Ile Val Gly Val Gln Ser Val Ser Pro
     305                 310                 315                 320
     Thr Leu Ser Val Arg Arg Lys Ile Asp Asn Glu Thr Ile Pro Lys Arg
                     325                 330                 335
     Asp Ile Val Ala Asp Asp Ser Gly Lys Thr Val Ser Ile Ser Leu
                 340                 345                 350
     Trp Asn Asp Leu Ala Thr Thr Thr Gly Gln Glu Leu Leu Asp Met Ala
                 355                 360                 365
     Asp Ser Ser Pro Val Val Ala Ile Lys Ser Leu Lys Val Ser Asp Phe
             370                 375                 380
     Gln Gly Val Ser Leu Ser Thr Val Gly Lys Ser Thr Leu Ala Ile Asn
     385                 390                 395                 400
     Pro Asp Leu His Glu Ala Gln Asn Leu Lys Ser Trp Tyr Asp Ser Glu
                     405                 410                 415
     Gly Lys Asp Thr Ser Leu Ala Pro Ile Gly Ala Glu Met Gly Ala Ala
                 420                 425                 430
     Arg Ala Gly Gly Phe Lys Ser Thr Tyr Ser Asp Arg Val Phe Leu Ser
             435                 440                 445
     His Ile Thr Ser Asp Pro Ala Met Gly Gln Glu Lys Pro Val Phe Phe
             450                 455                 460
     Ser Leu Tyr Ala Thr Ile Ser His Ile Lys Pro Asp Gln Asn Met Trp
     465                 470                 475                 480
```

```
Tyr Arg Ala Cys Lys Thr Cys Asn Lys Val Thr Glu Thr Phe Gly
                485                 490                 495

Ser Gly Tyr Trp Cys Glu Gly Cys Gln Lys Asn Asp Ser Glu Cys Ser
            500                 505                 510

Leu Arg Tyr Ile Met Val Ile Lys Val Ser Asp Pro Thr Gly Glu Ala
            515                 520                 525

Trp Phe Ser Val Phe Asn Glu His Ala Glu Lys Ile Ile Gly Cys Ser
        530                 535                 540

Ala Asp Glu Leu Asp Arg Ile Arg Lys Glu Gly Asp Asp Ser Tyr
545                 550                 555                 560

Val Leu Lys Leu Lys Glu Ala Thr Trp Val Pro His Leu Phe Arg Val
            565                 570                 575

Ser Val Thr Gln His Glu Tyr Asn Asn Glu Lys Arg Gln Arg Ile Thr
            580                 585                 590

Val Arg Ser Glu Ala Pro Val Glu His Ala Ala Glu Ser Lys Tyr Leu
            595                 600                 605

Leu Glu Gln Ile Ala Lys Leu Thr Ala
            610                 615
```

<210> SEQ ID NO 5
<211> LENGTH: 630
<212> TYPE: PRT
<213> ORGANISM: Oryza sativa

<400> SEQUENCE: 5

```
Met Asp Ser Asp Ala Ala Pro Ser Val Thr Pro Gly Ala Val Ala Phe
1               5                   10                  15

Val Leu Glu Asn Ala Ser Pro Asp Ala Ala Thr Gly Val Pro Val Pro
            20                  25                  30

Glu Ile Val Leu Gln Val Asp Leu Lys Pro Ile Gly Thr Arg Phe
            35                  40                  45

Thr Phe Leu Ala Ser Asp Gly Lys Asp Lys Ile Lys Thr Met Leu Leu
    50                  55                  60

Thr Gln Leu Ala Pro Glu Val Arg Ser Gly Asn Ile Gln Asn Leu Gly
65                  70                  75                  80

Val Ile Arg Val Leu Asp Tyr Thr Cys Asn Thr Ile Gly Glu Lys Gln
            85                  90                  95

Glu Lys Val Leu Ile Ile Thr Lys Leu Glu Val Phe Lys Ala Leu
            100                 105                 110

Asp Ser Glu Ile Lys Cys Glu Ala Glu Lys Gln Glu Lys Pro Ala
            115                 120                 125

Ile Leu Leu Ser Pro Lys Glu Ser Val Val Leu Ser Lys Pro Thr
    130                 135                 140

Asn Ala Pro Pro Leu Pro Pro Val Val Leu Lys Pro Lys Gln Glu Val
145                 150                 155                 160

Lys Ser Ala Ser Gln Ile Val Asn Glu Gln Arg Gly Asn Ala Ala Pro
            165                 170                 175

Ala Ala Arg Leu Ala Met Thr Arg Arg Val His Pro Leu Ile Ser Leu
            180                 185                 190

Asn Pro Tyr Gln Gly Asn Trp Ile Ile Lys Val Arg Val Thr Ser Lys
            195                 200                 205

Gly Asn Leu Arg Thr Tyr Lys Asn Ala Arg Gly Glu Gly Cys Val Phe
            210                 215                 220

Asn Val Glu Leu Thr Asp Val Asp Gly Thr Gln Ile Gln Ala Thr Met
```

```
225                 230                 235                 240
Phe Asn Glu Ala Ala Lys Lys Phe Tyr Pro Met Phe Glu Leu Gly Lys
                245                 250                 255
Val Tyr Tyr Ile Ser Lys Gly Ser Leu Arg Val Ala Asn Lys Gln Phe
                260                 265                 270
Lys Thr Val His Asn Asp Tyr Glu Met Thr Leu Asn Glu Asn Ala Val
                275                 280                 285
Val Glu Glu Ala Glu Gly Glu Thr Phe Ile Pro Gln Ile Gln Tyr Asn
                290                 295                 300
Phe Val Lys Ile Asp Gln Leu Gly Pro Tyr Val Gly Gly Arg Glu Leu
305                 310                 315                 320
Val Asp Val Ile Gly Val Val Gln Ser Val Ser Pro Thr Leu Ser Val
                325                 330                 335
Arg Arg Lys Ile Asp Asn Glu Thr Ile Pro Lys Arg Asp Ile Val Val
                340                 345                 350
Ala Asp Asp Ser Ser Lys Thr Val Thr Ile Ser Leu Trp Asn Asp Leu
                355                 360                 365
Ala Thr Thr Thr Gly Gln Glu Leu Leu Asp Met Val Asp Ser Ala Pro
                370                 375                 380
Ile Ile Ala Ile Lys Ser Leu Lys Val Ser Asp Phe Gln Gly Leu Ser
385                 390                 395                 400
Leu Ser Thr Val Gly Arg Ser Thr Ile Val Val Asn Pro Asp Leu Pro
                405                 410                 415
Glu Ala Glu Gln Leu Arg Ala Trp Tyr Asp Ser Glu Gly Lys Gly Thr
                420                 425                 430
Ser Met Ala Ser Ile Gly Ser Asp Met Gly Ala Ser Arg Val Gly Gly
                435                 440                 445
Ala Arg Ser Met Tyr Ser Asp Arg Val Phe Leu Ser His Ile Thr Ser
                450                 455                 460
Asp Pro Asn Leu Gly Gln Asp Lys Pro Val Phe Phe Ser Leu Asn Ala
465                 470                 475                 480
Tyr Ile Ser Leu Ile Lys Pro Asp Gln Thr Met Trp Tyr Arg Ala Cys
                485                 490                 495
Lys Thr Cys Asn Lys Lys Val Thr Glu Ala Met Gly Ser Gly Tyr Trp
                500                 505                 510
Cys Glu Gly Cys Gln Lys Asn Asp Ala Glu Cys Ser Leu Arg Tyr Ile
                515                 520                 525
Met Val Ile Lys Val Ser Asp Pro Thr Gly Glu Ala Trp Leu Ser Leu
530                 535                 540
Phe Asn Asp Gln Ala Glu Arg Ile Val Gly Cys Ser Ala Asp Glu Leu
545                 550                 555                 560
Asp Arg Ile Arg Lys Glu Glu Gly Asp Asp Ser Tyr Leu Leu Lys Leu
                565                 570                 575
Lys Glu Ala Thr Trp Val Pro His Leu Phe Arg Val Ser Val Thr Gln
                580                 585                 590
Asn Glu Tyr Met Asn Glu Lys Arg Gln Arg Ile Thr Val Arg Ser Glu
                595                 600                 605
Ala Pro Val Asp His Ala Ala Glu Ala Lys Tyr Met Leu Glu Glu Ile
                610                 615                 620
Ala Lys Leu Thr Gly Cys
625                 630

<210> SEQ ID NO 6
```

```
<211> LENGTH: 609
<212> TYPE: PRT
<213> ORGANISM: Xenopus laevis

<400> SEQUENCE: 6

Met Ala Leu Pro Gln Leu Ser Glu Gly Ala Ile Ser Ala Met Leu Gly
 1               5                  10                  15

Gly Asp Ser Ser Cys Lys Pro Thr Leu Gln Val Ile Asn Ile Arg Pro
            20                  25                  30

Ile Asn Thr Gly Asn Gly Pro Pro Arg Tyr Arg Leu Leu Met Ser Asp
        35                  40                  45

Gly Leu Asn Thr Leu Ser Ser Phe Met Leu Ala Thr Gln Leu Asn Ser
    50                  55                  60

Leu Val Asp Asn Asn Leu Leu Ala Thr Asn Cys Ile Cys Gln Val Ser
65                  70                  75                  80

Arg Phe Ile Val Asn Asn Leu Lys Asp Gly Arg Arg Val Ile Ile Val
                85                  90                  95

Met Glu Leu Asp Val Leu Lys Ser Ala Asp Leu Val Met Gly Lys Ile
            100                 105                 110

Gly Asn Pro Gln Pro Tyr Asn Asp Gly Gln Pro Gln Ala Ala Pro
        115                 120                 125

Ala Pro Ala Ser Ala Pro Ala Pro Ser Lys Leu Gln Asn Asn
130                 135                 140

Ser Ala Pro Pro Ser Met Asn Arg Gly Thr Ser Lys Leu Phe Gly
145                 150                 155                 160

Gly Gly Ser Leu Leu Asn Thr Pro Gly Gly Ser Gln Ser Lys Val Val
                165                 170                 175

Pro Ile Ala Ser Leu Asn Pro Tyr Gln Ser Lys Trp Thr Val Arg Ala
            180                 185                 190

Arg Val Thr Asn Lys Gly Gln Ile Arg Thr Trp Ser Asn Ser Arg Gly
        195                 200                 205

Glu Gly Lys Leu Phe Ser Ile Glu Met Val Asp Glu Ser Gly Glu Ile
    210                 215                 220

Arg Ala Thr Ala Phe Asn Glu Gln Ala Asp Lys Phe Phe Ser Ile Ile
225                 230                 235                 240

Glu Val Asn Lys Val Tyr Tyr Phe Ser Lys Gly Thr Leu Lys Ile Ala
                245                 250                 255

Asn Lys Gln Tyr Thr Ser Val Lys Asn Asp Tyr Glu Met Thr Phe Asn
            260                 265                 270

Ser Glu Thr Ser Val Ile Pro Cys Asp Asp Ser Ala Asp Val Pro Met
        275                 280                 285

Val Gln Phe Glu Phe Val Ser Ile Gly Glu Leu Glu Ser Lys Asn Lys
    290                 295                 300

Asp Thr Val Leu Asp Ile Ile Gly Val Cys Lys Asn Val Glu Glu Val
305                 310                 315                 320

Thr Lys Val Thr Ile Lys Ser Asn Asn Arg Glu Val Ser Lys Arg Ser
                325                 330                 335

Ile His Leu Met Asp Ser Ser Gly Lys Val Val Ser Thr Thr Leu Trp
            340                 345                 350

Gly Glu Asp Ala Asp Lys Phe Asp Gly Ser Arg Gln Pro Val Val Ala
        355                 360                 365

Ile Lys Gly Ala Arg Leu Ser Asp Phe Gly Gly Arg Ser Leu Ser Val
    370                 375                 380

Leu Ser Ser Ser Thr Val Met Ile Asn Pro Asp Ile Pro Glu Ala Phe
385                 390                 395                 400
```

-continued

```
Lys Leu Arg Ala Trp Phe Asp Ser Glu Gly Gln Val Val Glu Gly Thr
                405                 410                 415
Ser Ile Ser Glu Ser Arg Gly Gly Thr Gly Gly Gly Asn Thr Asn
            420                 425                 430
Trp Lys Ser Leu Leu Glu Val Lys Asn Glu Asn Leu Gly His Gly Glu
                435                 440                 445
Lys Ala Asp Tyr Phe Thr Ser Val Ala Thr Ile Val Tyr Leu Arg Lys
            450                 455                 460
Glu Asn Cys Leu Tyr Gln Ala Cys Pro Ser Gln Asp Cys Asn Lys Lys
465                 470                 475                 480
Val Ile Asp Gln Gln Asn Gly Leu Phe Arg Cys Glu Lys Cys Asn Lys
                485                 490                 495
Glu Phe Pro Asn Phe Lys Tyr Arg Leu Ile Leu Ser Ala Asn Ile Ala
                500                 505                 510
Asp Phe Gly Glu Asn Gln Trp Ile Thr Cys Phe Gln Glu Ser Ala Glu
            515                 520                 525
Ser Ile Leu Gly Gln Asn Ala Thr Tyr Leu Gly Glu Leu Lys Glu Lys
            530                 535                 540
Asn Glu Gln Ala Tyr Asp Glu Val Phe Gln Asn Ala Asn Phe Arg Ser
545                 550                 555                 560
Tyr Thr Phe Arg Ala Arg Val Lys Leu Glu Thr Tyr Asn Asp Glu Ser
                565                 570                 575
Arg Ile Lys Ala Thr Ala Val Asp Val Lys Pro Val Asp His Lys Glu
            580                 585                 590
Tyr Ser Arg Arg Leu Ile Met Asn Ile Arg Lys Met Ala Thr Gln Gly
            595                 600                 605
Val
```

<210> SEQ ID NO 7
<211> LENGTH: 616
<212> TYPE: PRT
<213> ORGANISM: Homo sapiens

<400> SEQUENCE: 7

```
Met Val Gly Gln Leu Ser Glu Gly Ala Ile Ala Ala Ile Met Gln Lys
1               5                   10                  15
Gly Asp Thr Asn Ile Lys Pro Ile Leu Gln Val Ile Asn Ile Arg Pro
            20                  25                  30
Ile Thr Thr Gly Asn Ser Pro Pro Arg Tyr Arg Leu Leu Met Ser Asp
        35                  40                  45
Gly Leu Asn Thr Leu Ser Ser Phe Met Leu Ala Thr Gln Leu Asn Pro
    50                  55                  60
Leu Val Glu Glu Glu Gln Leu Ser Ser Asn Cys Val Cys Gln Ile His
65                  70                  75                  80
Arg Phe Ile Val Asn Thr Leu Lys Asp Gly Arg Arg Val Val Ile Leu
                85                  90                  95
Met Glu Leu Glu Val Leu Lys Ser Ala Glu Ala Val Gly Val Lys Ile
            100                 105                 110
Gly Asn Pro Val Pro Tyr Asn Glu Gly Leu Gly Gln Pro Gln Val Ala
        115                 120                 125
Pro Pro Ala Pro Ala Ala Ser Pro Ala Ala Ser Ser Arg Pro Gln Pro
    130                 135                 140
Gln Asn Gly Ser Ser Gly Met Gly Ser Thr Val Ser Lys Ala Tyr Gly
145                 150                 155                 160
```

```
Ala Ser Lys Thr Phe Gly Lys Ala Ala Gly Pro Ser Leu Ser His Thr
            165                 170                 175

Ser Gly Gly Thr Gln Ser Lys Val Val Pro Ile Ala Ser Leu Thr Pro
            180                 185                 190

Tyr Gln Ser Lys Trp Thr Ile Cys Ala Arg Val Thr Asn Lys Ser Gln
            195                 200                 205

Ile Arg Thr Trp Ser Asn Ser Arg Gly Glu Gly Lys Leu Phe Ser Leu
210                 215                 220

Glu Leu Val Asp Glu Ser Gly Glu Ile Arg Ala Thr Ala Phe Asn Glu
225                 230                 235                 240

Gln Val Asp Lys Phe Phe Pro Leu Ile Glu Val Asn Lys Val Tyr Tyr
            245                 250                 255

Phe Ser Lys Gly Thr Leu Lys Ile Ala Asn Lys Gln Phe Thr Ala Val
            260                 265                 270

Lys Asn Asp Tyr Glu Met Thr Phe Asn Asn Glu Thr Ser Val Met Pro
            275                 280                 285

Cys Glu Asp Asp His His Leu Pro Thr Val Gln Phe Asp Phe Thr Gly
            290                 295                 300

Ile Asp Asp Leu Glu Asn Lys Ser Lys Asp Ser Leu Val Asp Ile Ile
305                 310                 315                 320

Gly Ile Cys Lys Ser Tyr Glu Asp Ala Thr Lys Ile Thr Val Arg Ser
            325                 330                 335

Asn Asn Arg Glu Val Ala Lys Arg Asn Ile Tyr Leu Met Asp Thr Ser
            340                 345                 350

Gly Lys Val Val Thr Ala Thr Leu Trp Gly Glu Asp Ala Asp Lys Phe
            355                 360                 365

Asp Gly Ser Arg Gln Pro Val Leu Ala Ile Lys Gly Ala Arg Val Ser
            370                 375                 380

Asp Phe Gly Gly Arg Ser Leu Ser Val Leu Ser Ser Ser Thr Ile Ile
385                 390                 395                 400

Ala Asn Pro Asp Ile Pro Glu Ala Tyr Lys Leu Arg Gly Trp Phe Asp
            405                 410                 415

Ala Glu Gly Gln Ala Leu Asp Gly Val Ser Ile Ser Asp Leu Lys Ser
            420                 425                 430

Gly Gly Val Gly Gly Ser Asn Thr Asn Trp Lys Thr Leu Tyr Glu Val
            435                 440                 445

Lys Ser Glu Asn Leu Gly Gln Gly Asp Lys Pro Asp Tyr Phe Ser Ser
450                 455                 460

Val Ala Thr Val Val Tyr Leu Arg Lys Glu Asn Cys Met Tyr Gln Ala
465                 470                 475                 480

Cys Pro Thr Gln Asp Cys Asn Lys Lys Val Ile Asp Gln Gln Asn Gly
            485                 490                 495

Leu Tyr Arg Cys Glu Lys Cys Asp Thr Glu Phe Pro Asn Phe Lys Tyr
            500                 505                 510

Arg Met Ile Leu Ser Val Asn Ile Ala Asp Phe Gln Glu Asn Gln Trp
            515                 520                 525

Val Thr Cys Phe Gln Glu Ser Ala Glu Ala Ile Leu Gly Gln Asn Ala
            530                 535                 540

Ala Tyr Leu Gly Glu Leu Lys Asp Lys Asn Glu Gln Ala Phe Glu Glu
545                 550                 555                 560

Val Phe Gln Asn Ala Asn Phe Arg Ser Phe Ile Phe Arg Val Arg Val
            565                 570                 575
```

-continued

Lys Val Glu Thr Tyr Asn Asp Glu Ser Arg Ile Lys Ala Thr Val Met
            580                 585                 590

Asp Val Lys Pro Val Asp Tyr Arg Glu Tyr Gly Arg Arg Leu Val Met
            595                 600                 605

Ser Ile Arg Arg Ser Ala Leu Met
            610                 615

<210> SEQ ID NO 8
<211> LENGTH: 603
<212> TYPE: PRT
<213> ORGANISM: Drosophila melanogaster

<400> SEQUENCE: 8

Met Val Leu Ala Ser Leu Ser Thr Gly Val Ile Ala Arg Ile Met His
  1               5                  10                  15

Gly Glu Val Val Asp Ala Pro Val Leu Gln Ile Leu Ala Ile Lys Lys
                 20                  25                  30

Ile Asn Ser Ala Ala Asp Ser Glu Arg Tyr Arg Ile Leu Ile Ser Asp
            35                  40                  45

Gly Lys Tyr Phe Asn Ser Tyr Ala Met Leu Ala Ser Gln Leu Asn Val
  50                  55                  60

Met Gln His Asn Gly Glu Leu Glu Glu Phe Thr Ile Val Gln Leu Asp
 65                  70                  75                  80

Lys Tyr Val Thr Ser Leu Val Gly Lys Asp Gly Ala Gly Lys Arg Val
                 85                  90                  95

Leu Ile Ile Ser Glu Leu Thr Val Val Asn Pro Gly Ala Glu Val Lys
            100                 105                 110

Ser Lys Ile Gly Glu Pro Val Thr Tyr Glu Asn Ala Ala Lys Gln Asp
            115                 120                 125

Leu Ala Pro Lys Pro Ala Val Thr Ser Asn Ser Lys Pro Ile Ala Lys
130                 135                 140

Lys Glu Pro Ser His Asn Asn Asn Asn Ile Val Met Asn Ser Ser
145                 150                 155                 160

Ile Asn Ser Gly Met Thr His Pro Ile Ser Ser Leu Ser Pro Tyr Gln
                165                 170                 175

Asn Lys Trp Val Ile Lys Ala Arg Val Thr Ser Lys Ser Gly Ile Arg
            180                 185                 190

Thr Trp Ser Asn Ala Arg Gly Glu Gly Lys Leu Phe Ser Met Asp Leu
            195                 200                 205

Met Asp Glu Ser Gly Glu Ile Arg Ala Thr Ala Phe Lys Glu Gln Cys
        210                 215                 220

Asp Lys Phe Tyr Asp Leu Ile Gln Val Asp Ser Val Tyr Tyr Ile Ser
225                 230                 235                 240

Lys Cys Gln Leu Lys Pro Ala Asn Lys Gln Tyr Ser Ser Leu Asn Asn
                245                 250                 255

Ala Tyr Glu Met Thr Phe Ser Gly Glu Thr Val Val Gln Leu Cys Glu
            260                 265                 270

Asp Thr Asp Asp Asp Pro Ile Pro Glu Ile Lys Tyr Asn Leu Val Pro
            275                 280                 285

Ile Ser Asp Val Ser Gly Met Glu Asn Lys Ala Ala Val Asp Thr Ile
        290                 295                 300

Gly Ile Cys Lys Glu Val Gly Glu Leu Gln Ser Phe Val Ala Arg Thr
305                 310                 315                 320

Thr Asn Lys Glu Phe Lys Lys Arg Asp Ile Thr Leu Val Asp Met Ser
                325                 330                 335

```
Asn Ser Ala Ile Ser Leu Thr Leu Trp Gly Asp Asp Ala Val Asn Phe
            340                 345                 350

Asp Gly His Val Gln Pro Val Ile Leu Val Lys Gly Thr Arg Ile Asn
            355                 360                 365

Glu Phe Asn Gly Gly Lys Ser Leu Ser Leu Gly Gly Gly Ser Ile Met
            370                 375                 380

Lys Ile Asn Pro Asp Ile Pro Glu Ala His Lys Leu Arg Gly Trp Phe
385                 390                 395                 400

Asp Asn Gly Gly Asp Ser Val Ala Asn Met Val Ser Ala Arg Thr
            405                 410                 415

Gly Gly Gly Ser Phe Ser Thr Glu Trp Met Thr Leu Lys Asp Ala Arg
            420                 425                 430

Ala Arg Asn Leu Gly Ser Gly Asp Lys Pro Asp Tyr Phe Gln Cys Lys
            435                 440                 445

Ala Val His Ile Val Lys Gln Glu Asn Ala Phe Tyr Arg Ala Cys
            450                 455                 460

Pro Gln Ser Asp Cys Asn Lys Lys Val Asp Glu Gly Asn Asp Gln
465                 470                 475                 480

Phe Arg Cys Glu Lys Cys Asn Ala Leu Phe Pro Asn Phe Lys Tyr Arg
            485                 490                 495

Leu Leu Ile Asn Met Ser Ile Gly Asp Trp Thr Ser Asn Arg Trp Val
            500                 505                 510

Ser Ser Phe Asn Glu Val Gly Glu Gln Leu Leu Gly His Thr Ser Gln
            515                 520                 525

Glu Val Gly Glu Ala Leu Glu Asn Asp Pro Ala Lys Ala Glu Gln Ile
            530                 535                 540

Phe Ser Ala Leu Asn Phe Thr Ser His Ile Phe Lys Leu Arg Cys Lys
545                 550                 555                 560

Asn Glu Val Tyr Gly Asp Met Thr Arg Asn Lys Leu Thr Val Gln Ser
            565                 570                 575

Val Ala Pro Ile Asn His Lys Glu Tyr Asn Lys His Leu Leu Lys Glu
            580                 585                 590

Leu Gln Glu Leu Thr Gly Ile Gly Ser Ser Asn
            595                 600

<210> SEQ ID NO 9
<211> LENGTH: 609
<212> TYPE: PRT
<213> ORGANISM: Schizosaccharomyces pombe

<400> SEQUENCE: 9

Met Ala Glu Arg Leu Ser Val Gly Ala Leu Arg Ile Ile Asn Thr Ser
1               5                   10                  15

Asp Ala Ser Ser Phe Pro Pro Asn Pro Ile Leu Gln Val Leu Thr Val
            20                  25                  30

Lys Glu Leu Asn Ser Asn Pro Thr Ser Gly Ala Pro Lys Arg Tyr Arg
        35                  40                  45

Val Val Leu Ser Asp Ser Ile Asn Tyr Ala Gln Ser Met Leu Ser Thr
    50                  55                  60

Gln Leu Asn His Leu Val Ala Glu Asn Lys Gln Lys Gly Ala Phe
65                  70                  75                  80

Val Gln Leu Thr Gln Phe Thr Val Asn Val Met Lys Glu Arg Lys Ile
            85                  90                  95

Leu Ile Val Leu Gly Leu Asn Val Leu Thr Glu Leu Gly Val Met Asp
```

-continued

```
                100                 105                 110
Lys Ile Gly Asn Pro Ala Gly Leu Glu Thr Val Asp Ala Leu Arg Gln
            115                 120                 125

Gln Gln Asn Glu Gln Asn Ala Ser Ala Pro Arg Thr Gly Ile Ser
130                 135                 140

Thr Ser Thr Asn Ser Phe Tyr Gly Asn Asn Ala Ala Thr Ala Pro
145                 150                 155                 160

Ala Pro Pro Met Met Lys Lys Pro Ala Ala Pro Asn Ser Leu Ser
                165                 170                 175

Thr Ile Ile Tyr Pro Ile Glu Gly Leu Ser Pro Tyr Gln Asn Lys Trp
            180                 185                 190

Thr Ile Arg Ala Arg Val Thr Asn Lys Ser Glu Val Lys His Trp His
            195                 200                 205

Asn Gln Arg Gly Glu Gly Lys Leu Phe Ser Val Asn Leu Leu Asp Glu
210                 215                 220

Ser Gly Glu Ile Arg Ala Thr Gly Phe Asn Asp Gln Val Asp Ala Phe
225                 230                 235                 240

Tyr Asp Ile Leu Gln Glu Gly Ser Val Tyr Tyr Ile Ser Arg Cys Arg
                245                 250                 255

Val Asn Ile Ala Lys Lys Gln Tyr Thr Asn Val Gln Asn Glu Tyr Glu
                260                 265                 270

Leu Met Phe Glu Arg Asp Thr Glu Ile Arg Lys Ala Glu Asp Gln Thr
            275                 280                 285

Ala Val Pro Val Ala Lys Phe Ser Phe Val Ser Leu Gln Glu Val Gly
            290                 295                 300

Asp Val Ala Lys Asp Ala Val Ile Asp Val Ile Gly Val Leu Gln Asn
305                 310                 315                 320

Val Gly Pro Val Gln Gln Ile Thr Ser Arg Ala Thr Ser Arg Gly Phe
                325                 330                 335

Asp Lys Arg Asp Ile Thr Ile Val Asp Gln Thr Gly Tyr Glu Met Arg
                340                 345                 350

Val Thr Leu Trp Gly Lys Thr Ala Ile Glu Phe Ser Val Ser Glu Glu
            355                 360                 365

Ser Ile Leu Ala Phe Lys Gly Val Lys Val Asn Asp Phe Gln Gly Arg
370                 375                 380

Ser Leu Ser Met Leu Thr Ser Thr Met Ser Val Asp Pro Asp Ile
385                 390                 395                 400

Gln Glu Ser His Leu Leu Lys Gly Trp Tyr Asp Gly Gln Gly Arg Gly
                405                 410                 415

Gln Glu Phe Ala Lys His Ser Val Ile Ser Ser Thr Leu Ser Thr Thr
                420                 425                 430

Gly Arg Ser Ala Glu Arg Lys Asn Ile Ala Glu Val Gln Ala Glu His
            435                 440                 445

Leu Gly Met Ser Glu Thr Pro Asp Tyr Phe Ser Leu Lys Gly Thr Ile
            450                 455                 460

Val Tyr Ile Arg Lys Lys Asn Val Ser Tyr Pro Ala Cys Pro Ala Ala
465                 470                 475                 480

Asp Cys Asn Lys Lys Val Phe Asp Gln Gly Gly Ser Trp Arg Cys Glu
                485                 490                 495

Lys Cys Asn Lys Glu Tyr Asp Ala Pro Gln Tyr Arg Tyr Ile Ile Thr
                500                 505                 510

Ile Ala Val Gly Asp His Thr Gly Gln Leu Trp Leu Asn Val Phe Asp
            515                 520                 525
```

```
Asp Val Gly Lys Leu Ile Met His Lys Thr Ala Asp Glu Leu Asn Asp
        530                 535                 540

Leu Gln Glu Asn Asp Glu Asn Ala Phe Met Asn Cys Met Ala Glu Ala
545                 550                 555                 560

Cys Tyr Met Pro Tyr Ile Phe Gln Cys Arg Ala Lys Gln Asp Asn Phe
                565                 570                 575

Lys Gly Glu Met Arg Val Arg Tyr Thr Val Met Ser Ile Asn Gln Met
                580                 585                 590

Asp Trp Lys Glu Glu Ser Lys Arg Leu Ile Asn Phe Ile Glu Ser Ala
            595                 600                 605
Gln

<210> SEQ ID NO 10
<211> LENGTH: 621
<212> TYPE: PRT
<213> ORGANISM: Saccharomyces cerevisiae

<400> SEQUENCE: 10

Met Ser Ser Val Gln Leu Ser Arg Gly Asp Phe His Ser Ile Phe Thr
  1                 5                  10                  15

Asn Lys Gln Arg Tyr Asp Asn Pro Thr Gly Gly Val Tyr Gln Val Tyr
                 20                  25                  30

Asn Thr Arg Lys Ser Asp Gly Ala Asn Ser Asn Arg Lys Asn Leu Ile
             35                  40                  45

Met Ile Ser Asp Gly Ile Tyr His Met Lys Ala Leu Leu Arg Asn Gln
 50                  55                  60

Ala Ala Ser Lys Phe Gln Ser Met Glu Leu Gln Arg Gly Asp Ile Ile
65                  70                  75                  80

Arg Val Ile Ile Ala Glu Pro Ala Ile Val Arg Glu Arg Lys Lys Tyr
                 85                  90                  95

Val Leu Leu Val Asp Asp Phe Glu Leu Val Gln Ser Arg Ala Asp Met
                100                 105                 110

Val Asn Gln Thr Ser Thr Phe Leu Asp Asn Tyr Phe Ser Glu His Pro
            115                 120                 125

Asn Glu Thr Leu Lys Asp Glu Asp Ile Thr Asp Ser Gly Asn Val Ala
130                 135                 140

Asn Gln Thr Asn Ala Ser Asn Ala Gly Val Pro Asp Met Leu His Ser
145                 150                 155                 160

Asn Ser Asn Leu Asn Ala Asn Glu Arg Lys Phe Ala Asn Glu Asn Pro
                165                 170                 175

Asn Ser Gln Lys Thr Arg Pro Ile Phe Ala Ile Glu Gln Leu Ser Pro
            180                 185                 190

Tyr Gln Asn Val Trp Thr Ile Lys Ala Arg Val Ser Tyr Lys Gly Glu
            195                 200                 205

Ile Lys Thr Trp His Asn Gln Arg Gly Asp Gly Lys Leu Phe Asn Val
210                 215                 220

Asn Phe Leu Asp Thr Ser Gly Glu Ile Arg Ala Thr Ala Phe Asn Asp
225                 230                 235                 240

Phe Ala Thr Lys Phe Asn Glu Ile Leu Gln Glu Gly Lys Val Tyr Tyr
                245                 250                 255

Val Ser Lys Ala Lys Leu Gln Pro Ala Lys Pro Gln Phe Thr Asn Leu
            260                 265                 270

Thr His Pro Tyr Glu Leu Asn Leu Asp Arg Asp Thr Val Ile Glu Glu
        275                 280                 285
```

```
Cys Phe Asp Glu Ser Asn Val Pro Lys Thr His Phe Asn Phe Ile Lys
    290                 295                 300

Leu Asp Ala Ile Gln Asn Gln Glu Val Asn Ser Asn Val Asp Val Leu
305                 310                 315                 320

Gly Ile Ile Gln Thr Ile Asn Pro His Phe Glu Leu Thr Ser Arg Ala
                325                 330                 335

Gly Lys Lys Phe Asp Arg Arg Asp Ile Thr Ile Val Asp Asp Ser Gly
                340                 345                 350

Phe Ser Ile Ser Val Gly Leu Trp Asn Gln Gln Ala Leu Asp Phe Asn
                355                 360                 365

Leu Pro Glu Gly Ser Val Ala Ala Ile Lys Gly Val Arg Val Thr Asp
370                 375                 380

Phe Gly Gly Lys Ser Leu Ser Met Gly Phe Ser Ser Thr Leu Ile Pro
385                 390                 395                 400

Asn Pro Glu Ile Pro Glu Ala Tyr Ala Leu Lys Gly Trp Tyr Asp Ser
                405                 410                 415

Lys Gly Arg Asn Ala Asn Phe Ile Thr Leu Lys Gln Glu Pro Gly Met
                420                 425                 430

Gly Gly Gln Ser Ala Ala Ser Leu Thr Lys Phe Ile Ala Gln Arg Ile
                435                 440                 445

Thr Ile Ala Arg Ala Gln Ala Glu Asn Leu Gly Arg Ser Glu Lys Gly
                450                 455                 460

Asp Phe Phe Ser Val Lys Ala Ala Ile Ser Phe Leu Lys Val Asp Asn
465                 470                 475                 480

Phe Ala Tyr Pro Ala Cys Ser Asn Glu Asn Cys Asn Lys Lys Val Leu
                485                 490                 495

Glu Gln Pro Asp Gly Thr Trp Arg Cys Glu Lys Cys Asp Thr Asn Asn
                500                 505                 510

Ala Arg Pro Asn Trp Arg Tyr Ile Leu Thr Ile Ser Ile Ile Asp Glu
                515                 520                 525

Thr Asn Gln Leu Trp Leu Thr Leu Phe Asp Asp Gln Ala Lys Gln Leu
                530                 535                 540

Leu Gly Val Asp Ala Asn Thr Leu Met Ser Leu Lys Glu Glu Asp Pro
545                 550                 555                 560

Asn Glu Phe Thr Lys Ile Thr Gln Ser Ile Gln Met Asn Glu Tyr Asp
                565                 570                 575

Phe Arg Ile Arg Ala Arg Glu Asp Thr Tyr Asn Asp Gln Ser Arg Ile
                580                 585                 590

Arg Tyr Thr Val Ala Asn Leu His Ser Leu Asn Tyr Arg Ala Glu Ala
                595                 600                 605

Asp Tyr Leu Ala Asp Glu Leu Ser Lys Ala Leu Leu Ala
610                 615                 620

<210> SEQ ID NO 11
<211> LENGTH: 1124
<212> TYPE: DNA
<213> ORGANISM: Zea mays
<220> FEATURE:
<221> NAME/KEY: misc_feature
<222> LOCATION: (0)...(0)
<223> OTHER INFORMATION: Maize RPA Middle Subunit Homologue-1
<220> FEATURE:
<221> NAME/KEY: CDS
<222> LOCATION: (76)...(894)

<400> SEQUENCE: 11
```

```
tcgacccacg cgtccgatcc tcccatctgc gcaccgcaa gcctattcgc cgcacctcct      60
caggtgaccg ggaag atg atg ccg ttg agc caa acc gac ttc tcg ccg tcg     111
              Met Met Pro Leu Ser Gln Thr Asp Phe Ser Pro Ser
               1               5                   10 cag ttc acc tcc tcc cag aat gcc gcc gcc gac tcc acc acg cct tcc     159
Gln Phe Thr Ser Ser Gln Asn Ala Ala Ala Asp Ser Thr Thr Pro Ser
         15                  20                  25 aag atg cgc ggc gcg tcc agc acc atg ccg ctc acc gtg aag cag gtc     207
Lys Met Arg Gly Ala Ser Ser Thr Met Pro Leu Thr Val Lys Gln Val
 30                  35                  40 gtc gac gcg cag cag tct ggc acg ggc gag aag ggc gct ccg ttc atc     255
Val Asp Ala Gln Gln Ser Gly Thr Gly Glu Lys Gly Ala Pro Phe Ile
 45                  50                  55                  60 gtc aat ggc gtc gag atg gct aac att cga ctt gtg ggg atg gtc aat     303
Val Asn Gly Val Glu Met Ala Asn Ile Arg Leu Val Gly Met Val Asn
             65                  70                  75 gcc aag gtg gag cgg acg acc gat gtg acc ttc acg ctc gac gat ggc     351
Ala Lys Val Glu Arg Thr Thr Asp Val Thr Phe Thr Leu Asp Asp Gly
         80                  85                  90 acc ggc cgc ctc gat ttc atc aga tgg gtg aat gat gct tca gat tct     399
Thr Gly Arg Leu Asp Phe Ile Arg Trp Val Asn Asp Ala Ser Asp Ser
         95                  100                 105 ttt gaa act gct gct att cag aat ggt atg tac att gcg gtc att gga     447
Phe Glu Thr Ala Ala Ile Gln Asn Gly Met Tyr Ile Ala Val Ile Gly
    110                 115                 120 agc ctc aag gga ctg caa gag agg aag cgt gct act gct ttc tca atc     495
Ser Leu Lys Gly Leu Gln Glu Arg Lys Arg Ala Thr Ala Phe Ser Ile
125                 130                 135                 140 agg cct ata acc gat ttc aat gag gtt acg ctg cat ttc att cag tgt     543
Arg Pro Ile Thr Asp Phe Asn Glu Val Thr Leu His Phe Ile Gln Cys
                145                 150                 155 gtt cgg atg cat ata gag aac att gaa tta aag gct ggc agt cct gca     591
Val Arg Met His Ile Glu Asn Ile Glu Leu Lys Ala Gly Ser Pro Ala
            160                 165                 170 cga atc agt tct tct atg gga gtg tca ttc tca aat gga ttc agt gaa     639
Arg Ile Ser Ser Ser Met Gly Val Ser Phe Ser Asn Gly Phe Ser Glu
        175                 180                 185 tca agc aca ccg aca tct ttg aaa tcc agt ccc gca ccg gtg acc agc     687
Ser Ser Thr Pro Thr Ser Leu Lys Ser Ser Pro Ala Pro Val Thr Ser
    190                 195                 200 ggg tca tcc gat act gat ctg cac acg cag gtc ctg aat ttt ttt aat     735
Gly Ser Ser Asp Thr Asp Leu His Thr Gln Val Leu Asn Phe Phe Asn
205                 210                 215                 220 gaa cca gcg aac ctc gag agt gag cat ggg gtg cac gtt gat gaa gta     783
Glu Pro Ala Asn Leu Glu Ser Glu His Gly Val His Val Asp Glu Val
                225                 230                 235 ctc aag cgg ttc aaa ctt ttg ccg aag aag cag atc acg gat gct att     831
Leu Lys Arg Phe Lys Leu Leu Pro Lys Lys Gln Ile Thr Asp Ala Ile
            240                 245                 250 gat tac aat atg gac tcg ggg cgt ctt tac tca aca att gat gaa ttc     879
Asp Tyr Asn Met Asp Ser Gly Arg Leu Tyr Ser Thr Ile Asp Glu Phe
        255                 260                 265 cac tac aag gca act taaccgattt gaaggccagc tgctggaaa tggcagagga     934
His Tyr Lys Ala Thr
    270 ctaagtatca cttgtactaa accaaagtct ggaaatgtca tgttgtgtca tgaaatgcat    994 ggttggttta tggaaacatt tatatcttgt atcaactagt tgatttgtat ctcgtgtcaa   1054 cttaatgact gagccaagaa aaggaagatg tagaggccga cagaaaaaaa aaaaaaaaa    1114
```
aaaaaaaaaa                                                          1124

<210> SEQ ID NO 12
<211> LENGTH: 273
<212> TYPE: PRT
<213> ORGANISM: Zea mays

<400> SEQUENCE: 12

```
Met Met Pro Leu Ser Gln Thr Asp Phe Ser Pro Ser Gln Phe Thr Ser
 1               5                  10                  15

Ser Gln Asn Ala Ala Asp Ser Thr Thr Pro Ser Lys Met Arg Gly
             20                  25                  30

Ala Ser Ser Thr Met Pro Leu Thr Val Lys Gln Val Val Asp Ala Gln
         35                  40                  45

Gln Ser Gly Thr Gly Glu Lys Gly Ala Pro Phe Ile Val Asn Gly Val
     50                  55                  60

Glu Met Ala Asn Ile Arg Leu Val Gly Met Val Asn Ala Lys Val Glu
 65                  70                  75                  80

Arg Thr Thr Asp Val Thr Phe Thr Leu Asp Asp Gly Thr Gly Arg Leu
                 85                  90                  95

Asp Phe Ile Arg Trp Val Asn Asp Ala Ser Asp Ser Phe Glu Thr Ala
            100                 105                 110

Ala Ile Gln Asn Gly Met Tyr Ile Ala Val Ile Gly Ser Leu Lys Gly
        115                 120                 125

Leu Gln Glu Arg Lys Arg Ala Thr Ala Phe Ser Ile Arg Pro Ile Thr
    130                 135                 140

Asp Phe Asn Glu Val Thr Leu His Phe Ile Gln Cys Val Arg Met His
145                 150                 155                 160

Ile Glu Asn Ile Glu Leu Lys Ala Gly Ser Pro Ala Arg Ile Ser Ser
                165                 170                 175

Ser Met Gly Val Ser Phe Ser Asn Gly Phe Ser Glu Ser Ser Thr Pro
            180                 185                 190

Thr Ser Leu Lys Ser Ser Pro Ala Pro Val Thr Ser Gly Ser Ser Asp
        195                 200                 205

Thr Asp Leu His Thr Gln Val Leu Asn Phe Asn Glu Pro Ala Asn
    210                 215                 220

Leu Glu Ser Glu His Gly Val His Val Asp Glu Val Leu Lys Arg Phe
225                 230                 235                 240

Lys Leu Leu Pro Lys Lys Gln Ile Thr Asp Ala Ile Asp Tyr Asn Met
                245                 250                 255

Asp Ser Gly Arg Leu Tyr Ser Thr Ile Asp Glu Phe His Tyr Lys Ala
            260                 265                 270
Thr
```

<210> SEQ ID NO 13
<211> LENGTH: 979
<212> TYPE: DNA
<213> ORGANISM: Zea mays
<220> FEATURE:
<221> NAME/KEY: misc_feature
<222> LOCATION: (0)...(0)
<223> OTHER INFORMATION: Maize RPA Middle Subunit Homologue-2 and 3
<220> FEATURE:
<221> NAME/KEY: CDS
<222> LOCATION: (37)...(855)

<400> SEQUENCE: 13
ttcggcacga gcgcacctcc tcaggtgacc gggaag atg atg ccg ttg agc caa         54

```
                                    Met Met Pro Leu Ser Gln
                                     1               5
acc gac ttc tcg ccg tcg cag ttc acc tcc tcc cag aat gcc gcc gcc    102
Thr Asp Phe Ser Pro Ser Gln Phe Thr Ser Ser Gln Asn Ala Ala Ala
            10                  15                  20 gac tcc acc acg cct tcc aag atg cgc ggc gcg tcc agc acc atg ccg    150
Asp Ser Thr Thr Pro Ser Lys Met Arg Gly Ala Ser Ser Thr Met Pro
        25                  30                  35 ctc acc gtg aag cag gtc gtc gac gcg cag cag tct ggc acg ggc gac    198
Leu Thr Val Lys Gln Val Val Asp Ala Gln Gln Ser Gly Thr Gly Asp
    40                  45                  50 aag ggc gct ccg ttc atc gtc aat ggc gtc gag atg gct aac att cga    246
Lys Gly Ala Pro Phe Ile Val Asn Gly Val Glu Met Ala Asn Ile Arg
55                  60                  65                  70 ctt gtg ggg atg gtc aat gcc aag gtg gag cgg acg acc gat gtg acc    294
Leu Val Gly Met Val Asn Ala Lys Val Glu Arg Thr Thr Asp Val Thr
                75                  80                  85 ttc acg ctc gac gat ggc acc ggc cgc ctc gat ttc atc aga tgg gtg    342
Phe Thr Leu Asp Asp Gly Thr Gly Arg Leu Asp Phe Ile Arg Trp Val
            90                  95                 100 aat gat gct tca gat tct ttt gaa act gct gct att cag aat ggt atg    390
Asn Asp Ala Ser Asp Ser Phe Glu Thr Ala Ala Ile Gln Asn Gly Met
        105                 110                 115 tac att gcg gtc att gga agc ctc aag gga ctg caa gag agg aag cgt    438
Tyr Ile Ala Val Ile Gly Ser Leu Lys Gly Leu Gln Glu Arg Lys Arg
    120                 125                 130 gct act gct ttc tca atc agg cct ata acc gat ttc aat gag gtt acg    486
Ala Thr Ala Phe Ser Ile Arg Pro Ile Thr Asp Phe Asn Glu Val Thr
135                 140                 145                 150 ctg cat ttc att cag tgt gtt cgg atg cat ata gag aac att gaa tta    534
Leu His Phe Ile Gln Cys Val Arg Met His Ile Glu Asn Ile Glu Leu
                155                 160                 165 aag gct ggc agt cct gca cga atc agt tct tct atg gga gtg tca ttc    582
Lys Ala Gly Ser Pro Ala Arg Ile Ser Ser Ser Met Gly Val Ser Phe
            170                 175                 180 tca aat gga ttc agt gaa tca agc aca ccg aca tct ttg aaa tcc agt    630
Ser Asn Gly Phe Ser Glu Ser Ser Thr Pro Thr Ser Leu Lys Ser Ser
        185                 190                 195 ccc gca ccg gtg acc agc ggg tca tcc gat act gat ctg cac acg cag    678
Pro Ala Pro Val Thr Ser Gly Ser Ser Asp Thr Asp Leu His Thr Gln
    200                 205                 210 gtc ctg aat ttt ttt aat gaa cca gcg aac ctc gag agt gag cat ggg    726
Val Leu Asn Phe Phe Asn Glu Pro Ala Asn Leu Glu Ser Glu His Gly
215                 220                 225                 230 gtg cac gtt gat gaa gta ctc aag cgg ttc aaa ctt ttg ccg aag aag    774
Val His Val Asp Glu Val Leu Lys Arg Phe Lys Leu Leu Pro Lys Lys
                235                 240                 245 cag atc acg gat gct att gat tac aat atg gac tcg ggg cgt ctt tac    822
Gln Ile Thr Asp Ala Ile Asp Tyr Asn Met Asp Ser Gly Arg Leu Tyr
            250                 255                 260 tca aca att gat gaa ttc cac tac aag gca act taaccgattt gaaggccagc    875
Ser Thr Ile Asp Glu Phe His Tyr Lys Ala Thr
        265                 270 ctgctggaaa tggcagagga ctaagtatca cttgtactaa accaaagtct ggaaatgtca    935
tgttgtgtca tgaaatgcat ggttggttta tggaaacaaa aaaa                    979

<210> SEQ ID NO 14
<211> LENGTH: 273
<212> TYPE: PRT
```

<213> ORGANISM: Zea mays

<400> SEQUENCE: 14

```
Met Met Pro Leu Ser Gln Thr Asp Phe Ser Pro Ser Gln Phe Thr Ser
  1               5                  10                  15

Ser Gln Asn Ala Ala Asp Ser Thr Thr Pro Ser Lys Met Arg Gly
         20                  25                  30

Ala Ser Ser Thr Met Pro Leu Thr Val Lys Gln Val Asp Ala Gln
         35                  40                  45

Gln Ser Gly Thr Gly Asp Lys Gly Ala Pro Phe Ile Val Asn Gly Val
     50                  55                  60

Glu Met Ala Asn Ile Arg Leu Val Gly Met Val Asn Ala Lys Val Glu
 65                  70                  75                  80

Arg Thr Thr Asp Val Thr Phe Thr Leu Asp Asp Gly Thr Gly Arg Leu
                     85                  90                  95

Asp Phe Ile Arg Trp Val Asn Asp Ala Ser Asp Ser Phe Glu Thr Ala
                100                 105                 110

Ala Ile Gln Asn Gly Met Tyr Ile Ala Val Ile Gly Ser Leu Lys Gly
            115                 120                 125

Leu Gln Glu Arg Lys Arg Ala Thr Ala Phe Ser Ile Arg Pro Ile Thr
    130                 135                 140

Asp Phe Asn Glu Val Thr Leu His Phe Ile Gln Cys Val Arg Met His
145                 150                 155                 160

Ile Glu Asn Ile Glu Leu Lys Ala Gly Ser Pro Ala Arg Ile Ser Ser
                165                 170                 175

Ser Met Gly Val Ser Phe Ser Asn Gly Phe Ser Glu Ser Ser Thr Pro
            180                 185                 190

Thr Ser Leu Lys Ser Ser Pro Ala Pro Val Thr Ser Gly Ser Ser Asp
    195                 200                 205

Thr Asp Leu His Thr Gln Val Leu Asn Phe Phe Asn Glu Pro Ala Asn
210                 215                 220

Leu Glu Ser Glu His Gly Val His Val Asp Glu Val Leu Lys Arg Phe
225                 230                 235                 240

Lys Leu Leu Pro Lys Lys Gln Ile Thr Asp Ala Ile Asp Tyr Asn Met
                245                 250                 255

Asp Ser Gly Arg Leu Tyr Ser Thr Ile Asp Glu Phe His Tyr Lys Ala
            260                 265                 270
Thr
```

<210> SEQ ID NO 15
<211> LENGTH: 1051
<212> TYPE: DNA
<213> ORGANISM: Zea mays
<220> FEATURE:
<221> NAME/KEY: misc_feature
<222> LOCATION: (0)...(0)
<223> OTHER INFORMATION: Maize RPA Middle Subunit Homologue-4
<220> FEATURE:
<221> NAME/KEY: CDS
<222> LOCATION: (76)...(894)

<400> SEQUENCE: 15

```
tcgacccacg cgtccgatcc tcccatctgc gcacccgcaa gcctattcgc cgcacctcct      60
caggtgaccg ggaag atg atg ccg ttg agc caa acc gac ttc tcg ccg tcg     111
              Met Met Pro Leu Ser Gln Thr Asp Phe Ser Pro Ser
                1               5                  10 cag ttc acc tcc tcc cag aat gcc gcc gcc gac tcc acc acg cct tcc     159
Gln Phe Thr Ser Ser Gln Asn Ala Ala Ala Asp Ser Thr Thr Pro Ser
```

|  |  |  |  |  |  |  |  |  |  |  |  |  |  |  |  |
|---|---|---|---|---|---|---|---|---|---|---|---|---|---|---|---|
|  | 15 |  |  |  | 20 |  |  |  |  | 25 |  |  |  |  |  |

```
aag atg cgc ggc gcg tcc agc acc atg ccg ctc acc gtg aag cag gtc      207
Lys Met Arg Gly Ala Ser Ser Thr Met Pro Leu Thr Val Lys Gln Val
     30                  35                  40 gtc gac gcg cag cag tct ggc acg ggc gag aag ggc gct ccg ttc atc      255
Val Asp Ala Gln Gln Ser Gly Thr Gly Glu Lys Gly Ala Pro Phe Ile
 45                  50                  55                  60 gtc aat ggc gtc gag atg gct aac att cga ctt gtg ggg atg gtc aat      303
Val Asn Gly Val Glu Met Ala Asn Ile Arg Leu Val Gly Met Val Asn
                     65                  70                  75 gcc aag gtg gag cgg acg acc gat gtg acc ttc acg ctc gac gat ggc      351
Ala Lys Val Glu Arg Thr Thr Asp Val Thr Phe Thr Leu Asp Asp Gly
                 80                  85                  90 acc ggc cgc ctc gat ttc atc aga tgg gtg aat gat gct tca gat tct      399
Thr Gly Arg Leu Asp Phe Ile Arg Trp Val Asn Asp Ala Ser Asp Ser
             95                 100                 105 ttt gaa act gct gct att cag aat ggt atg tac att gcg gtc att gga      447
Phe Glu Thr Ala Ala Ile Gln Asn Gly Met Tyr Ile Ala Val Ile Gly
        110                 115                 120 agc ctc aag gga ctg caa gag agg aag cgt gct act gct ttc tca atc      495
Ser Leu Lys Gly Leu Gln Glu Arg Lys Arg Ala Thr Ala Phe Ser Ile
125                 130                 135                 140 agg cct ata acc gat ttc aat gag gtt acg ctg cat ttc att cag tgt      543
Arg Pro Ile Thr Asp Phe Asn Glu Val Thr Leu His Phe Ile Gln Cys
                145                 150                 155 gtt cgg atg cat ata gag aac act gaa tta aag gct ggc agt cct gca      591
Val Arg Met His Ile Glu Asn Thr Glu Leu Lys Ala Gly Ser Pro Ala
            160                 165                 170 cga atc aat tct tct atg gga gtg tca ttc tca aat gga ttc agt gaa      639
Arg Ile Asn Ser Ser Met Gly Val Ser Phe Ser Asn Gly Phe Ser Glu
        175                 180                 185 tca agc aca ccg aca tct ttg aaa tcc agt ccc gca ccg gtg acc agc      687
Ser Ser Thr Pro Thr Ser Leu Lys Ser Ser Pro Ala Pro Val Thr Ser
    190                 195                 200 ggg tca tcc gat act gat ctg cac acg cag gtc ctg aat ttt ttt aat      735
Gly Ser Ser Asp Thr Asp Leu His Thr Gln Val Leu Asn Phe Phe Asn
205                 210                 215                 220 gaa cca gcg aac ctc gag agt gag cat ggg gtg cac gtt gat gaa gta      783
Glu Pro Ala Asn Leu Glu Ser Glu His Gly Val His Val Asp Glu Val
                225                 230                 235 ctc aag cgg ttc aaa ctt ttg ccg aag aag cag atc acg gat gct att      831
Leu Lys Arg Phe Lys Leu Leu Pro Lys Lys Gln Ile Thr Asp Ala Ile
            240                 245                 250 gat tac aat atg gac tcg ggg cgt ctt tac tca aca att gat gaa ttc      879
Asp Tyr Asn Met Asp Ser Gly Arg Leu Tyr Ser Thr Ile Asp Glu Phe
        255                 260                 265 cac tac aag gca act taaccgattt gaaggtcagc ctgctggaaa tggcagagga      934
His Tyr Lys Ala Thr
        270 ctaagtatca cttgtactaa accaaagtct ggaaatgtca tgttgtgtca tgaaatgcat      994 ggttggttta tggaaacaaa aaaaaaaaaa aaaaaaaaaa aaaaaaaaaa aaaaaa         1051
```

<210> SEQ ID NO 16
<211> LENGTH: 273
<212> TYPE: PRT
<213> ORGANISM: Zea mays

<400> SEQUENCE: 16

Met Met Pro Leu Ser Gln Thr Asp Phe Ser Pro Ser Gln Phe Thr Ser

```
                1               5                  10                 15
           Ser Gln Asn Ala Ala Asp Ser Thr Thr Pro Ser Lys Met Arg Gly
                           20                  25                  30

Ala Ser Ser Thr Met Pro Leu Thr Val Lys Gln Val Val Asp Ala Gln
                       35                  40                  45

Gln Ser Gly Thr Gly Glu Lys Gly Ala Pro Phe Ile Val Asn Gly Val
                   50                  55                  60

Glu Met Ala Asn Ile Arg Leu Val Gly Met Val Asn Ala Lys Val Glu
           65                  70                  75                  80

Arg Thr Thr Asp Val Thr Phe Thr Leu Asp Asp Gly Thr Gly Arg Leu
                               85                  90                  95

Asp Phe Ile Arg Trp Val Asn Asp Ala Ser Asp Ser Phe Glu Thr Ala
                           100                 105                 110

Ala Ile Gln Asn Gly Met Tyr Ile Ala Val Ile Gly Ser Leu Lys Gly
                       115                 120                 125

Leu Gln Glu Arg Lys Arg Ala Thr Ala Phe Ser Ile Arg Pro Ile Thr
                   130                 135                 140

Asp Phe Asn Glu Val Thr Leu His Phe Ile Gln Cys Val Arg Met His
           145                 150                 155                 160

Ile Glu Asn Thr Glu Leu Lys Ala Gly Ser Pro Ala Arg Ile Asn Ser
                               165                 170                 175

Ser Met Gly Val Ser Phe Ser Asn Gly Phe Ser Glu Ser Ser Thr Pro
                           180                 185                 190

Thr Ser Leu Lys Ser Ser Pro Ala Pro Val Thr Ser Gly Ser Ser Asp
                       195                 200                 205

Thr Asp Leu His Thr Gln Val Leu Asn Phe Phe Asn Glu Pro Ala Asn
                   210                 215                 220

Leu Glu Ser Glu His Gly Val His Val Asp Glu Val Leu Lys Arg Phe
           225                 230                 235                 240

Lys Leu Leu Pro Lys Lys Gln Ile Thr Asp Ala Ile Asp Tyr Asn Met
                               245                 250                 255

Asp Ser Gly Arg Leu Tyr Ser Thr Ile Asp Glu Phe His Tyr Lys Ala
                           260                 265                 270
           Thr

<210> SEQ ID NO 17
<211> LENGTH: 1087
<212> TYPE: DNA
<213> ORGANISM: Zea mays
<220> FEATURE:
<221> NAME/KEY: misc_feature
<222> LOCATION: (0)...(0)
<223> OTHER INFORMATION: Maize RPA Middle Subunit Homologue-5
<220> FEATURE:
<221> NAME/KEY: CDS
<222> LOCATION: (91)...(1044)

<400> SEQUENCE: 17
aattccgggg ccgacccacg cgtccgcatc gatcctccca tctgcgcacc cgcaagccta        60
ttcgccgcac ctcctcaggt gaccgggaag atg atg ccg ttg agc caa acc gac       114
                                 Met Met Pro Leu Ser Gln Thr Asp
                                  1               5 ttc tcg ccg tcg cag ttc acc tcc tcc cag aat gcc gcc gcc gac tcc        162
Phe Ser Pro Ser Gln Phe Thr Ser Ser Gln Asn Ala Ala Ala Asp Ser
     10                  15                  20 acc acg cct tcc aag atg cgc ggc gcg tcc agc acc atg ccg ctc acc        210
Thr Thr Pro Ser Lys Met Arg Gly Ala Ser Ser Thr Met Pro Leu Thr
```

-continued

```
        25                  30                  35                  40
gtg aag car gtc gtc gac gcg cag cag tct ggc acg ggc gag aag ggc      258
Val Lys Xaa Val Val Asp Ala Gln Gln Ser Gly Thr Gly Glu Lys Gly
                    45                  50                  55 gct ccg ttc atc gtc aat ggc gtc gag atg gct aac att cga ctt gtg      306
Ala Pro Phe Ile Val Asn Gly Val Glu Met Ala Asn Ile Arg Leu Val
                    60                  65                  70 ggg atg gtc aat gcc aag gtg gag cgg acg acc gat gtg acc ttc acg      354
Gly Met Val Asn Ala Lys Val Glu Arg Thr Thr Asp Val Thr Phe Thr
                75                  80                  85 ctc gac gat ggc acc ggc cgc ctc gat ttc atc aga tgg gtg aat gat      402
Leu Asp Asp Gly Thr Gly Arg Leu Asp Phe Ile Arg Trp Val Asn Asp
            90                  95                  100 gct tca gat tct ttt gaa act gct gct att cag aat ggt atg tac att      450
Ala Ser Asp Ser Phe Glu Thr Ala Ala Ile Gln Asn Gly Met Tyr Ile
105                 110                 115                 120 gcg gtc att gga agc ctc aag gga ctg caa gag agg aag cgt gct act      498
Ala Val Ile Gly Ser Leu Lys Gly Leu Gln Glu Arg Lys Arg Ala Thr
                125                 130                 135 gct ttc tca atc agg cct ata acc gat ttc aat gag gtt acg ctg cat      546
Ala Phe Ser Ile Arg Pro Ile Thr Asp Phe Asn Glu Val Thr Leu His
            140                 145                 150 ttc att cag tgt gtt cgg atg cat ata gag aac act gaa tta aag gct      594
Phe Ile Gln Cys Val Arg Met His Ile Glu Asn Thr Glu Leu Lys Ala
        155                 160                 165 ggc agt cct gca cga atc aat tct tct atg gga gtg tca ttc tca aat      642
Gly Ser Pro Ala Arg Ile Asn Ser Ser Met Gly Val Ser Phe Ser Asn
    170                 175                 180 gga ttc agt gaa tca agc aca ccg aca tct ttg aaa tcc agt ccc gca      690
Gly Phe Ser Glu Ser Ser Thr Pro Thr Ser Leu Lys Ser Ser Pro Ala
185                 190                 195                 200 ccg gtg acc agc ggg tca tcc gat act gat ctg cac acg cag gtc ctg      738
Pro Val Thr Ser Gly Ser Ser Asp Thr Asp Leu His Thr Gln Val Leu
                205                 210                 215 aat ttt ttt aat gaa cca gcg aac ctc gag agt gag cat ggg gtg cac      786
Asn Phe Phe Asn Glu Pro Ala Asn Leu Glu Ser Glu His Gly Val His
            220                 225                 230 gtt gat gaa gta ctc aag cgg ttc aac ttt tgc cga aga agc aga tca      834
Val Asp Glu Val Leu Lys Arg Phe Asn Phe Cys Arg Arg Ser Arg Ser
        235                 240                 245 cgg atg cta ttg att aca ata tgg act cgg ggc gtc ttt act caa caa      882
Arg Met Leu Leu Ile Thr Ile Trp Thr Arg Gly Val Phe Thr Gln Gln
    250                 255                 260 ttg atg aat tcc act aca agg caa ctt aac cga ttt gaa ggt cag cct      930
Leu Met Asn Ser Thr Thr Arg Gln Leu Asn Arg Phe Glu Gly Gln Pro
265                 270                 275                 280 gct gga aat ggc aga gga cta agt atc act tgt act aaa cca aag tct      978
Ala Gly Asn Gly Arg Gly Leu Ser Ile Thr Cys Thr Lys Pro Lys Ser
                285                 290                 295 gga aat gtc atg ttg tgt cat gaa atg cat ggt tgg ttt atg gaa aca     1026
Gly Asn Val Met Leu Cys His Glu Met His Gly Trp Phe Met Glu Thr
            300                 305                 310 ttt ata tct tgt atc aac tagttgattt gtatctcttg tgtcaaaaaa            1074
Phe Ile Ser Cys Ile Asn
            315 aaaaaaaaaa aaa                                                      1087

<210> SEQ ID NO 18
<211> LENGTH: 318
```

```
<212> TYPE: PRT
<213> ORGANISM: Zea mays
<220> FEATURE:
<221> NAME/KEY: VARIANT
<222> LOCATION: (1)...(318)
<223> OTHER INFORMATION: Xaa = Any Amino Acid

<400> SEQUENCE: 18
```

Met Met Pro Leu Ser Gln Thr Asp Phe Ser Pro Ser Gln Phe Thr Ser
1               5                   10                  15

Ser Gln Asn Ala Ala Ala Asp Ser Thr Thr Pro Ser Lys Met Arg Gly
            20                  25                  30

Ala Ser Ser Thr Met Pro Leu Thr Val Lys Xaa Val Val Asp Ala Gln
        35                  40                  45

Gln Ser Gly Thr Gly Glu Lys Gly Ala Pro Phe Ile Val Asn Gly Val
    50                  55                  60

Glu Met Ala Asn Ile Arg Leu Val Gly Met Val Asn Ala Lys Val Glu
65                  70                  75                  80

Arg Thr Thr Asp Val Thr Phe Thr Leu Asp Asp Gly Thr Gly Arg Leu
                85                  90                  95

Asp Phe Ile Arg Trp Val Asn Asp Ala Ser Asp Ser Phe Glu Thr Ala
            100                 105                 110

Ala Ile Gln Asn Gly Met Tyr Ile Ala Val Ile Gly Ser Leu Lys Gly
        115                 120                 125

Leu Gln Glu Arg Lys Arg Ala Thr Ala Phe Ser Ile Arg Pro Ile Thr
    130                 135                 140

Asp Phe Asn Glu Val Thr Leu His Phe Ile Gln Cys Val Arg Met His
145                 150                 155                 160

Ile Glu Asn Thr Glu Leu Lys Ala Gly Ser Pro Ala Arg Ile Asn Ser
                165                 170                 175

Ser Met Gly Val Ser Phe Ser Asn Gly Phe Ser Glu Ser Ser Thr Pro
            180                 185                 190

Thr Ser Leu Lys Ser Ser Pro Ala Pro Val Thr Ser Gly Ser Ser Asp
        195                 200                 205

Thr Asp Leu His Thr Gln Val Leu Asn Phe Phe Asn Glu Pro Ala Asn
    210                 215                 220

Leu Glu Ser Glu His Gly Val His Val Asp Glu Val Leu Lys Arg Phe
225                 230                 235                 240

Asn Phe Cys Arg Arg Ser Arg Ser Arg Met Leu Leu Ile Thr Ile Trp
                245                 250                 255

Thr Arg Gly Val Phe Thr Gln Gln Leu Met Asn Ser Thr Thr Arg Gln
            260                 265                 270

Leu Asn Arg Phe Glu Gly Gln Pro Ala Gly Asn Gly Arg Gly Leu Ser
        275                 280                 285

Ile Thr Cys Thr Lys Pro Lys Ser Gly Asn Val Met Leu Cys His Glu
    290                 295                 300

Met His Gly Trp Phe Met Glu Thr Phe Ile Ser Cys Ile Asn
305                 310                 315

```
<210> SEQ ID NO 19
<211> LENGTH: 1074
<212> TYPE: DNA
<213> ORGANISM: Zea mays
<220> FEATURE:
<221> NAME/KEY: misc_feature
<222> LOCATION: (0)...(0)
<223> OTHER INFORMATION: Maize RPA Middle Subunit Homologue-6
<220> FEATURE:
```

```
<221> NAME/KEY: CDS
<222> LOCATION: (55)...(873)

<400> SEQUENCE: 19
gacccacgcg tccgcgcaag cctattcgcc gcacctcctc aggtgaccgg gaag atg         57
                                                            Met
                                                            1 atg ccg ttg agc caa acc gac ttc tcg ccg tcg cag ttc acc tcc tcc        105
Met Pro Leu Ser Gln Thr Asp Phe Ser Pro Ser Gln Phe Thr Ser Ser
         5                  10                  15 cag aat gcc gcc gcc gac tcc acc acg cct tcc aag atg cgc ggc gcg        153
Gln Asn Ala Ala Ala Asp Ser Thr Thr Pro Ser Lys Met Arg Gly Ala
         20                  25                  30 tcc agc acc atg ccg ctc acc gtg aag cag gtc gtc gac gcg cag cag        201
Ser Ser Thr Met Pro Leu Thr Val Lys Gln Val Val Asp Ala Gln Gln
 35                  40                  45 tct ggc acg ggc gag aag ggc gct ccg ttc atc gtc aat ggc gtc gag        249
Ser Gly Thr Gly Glu Lys Gly Ala Pro Phe Ile Val Asn Gly Val Glu
 50                  55                  60                  65 atg gct aac att cga ctt gtg ggg atg gtc aat gcc aag gtg gag cgg        297
Met Ala Asn Ile Arg Leu Val Gly Met Val Asn Ala Lys Val Glu Arg
             70                  75                  80 acg acc gat gtg acc ttc acg ctc gat gat ggc acc ggc cgc ctc gat        345
Thr Thr Asp Val Thr Phe Thr Leu Asp Asp Gly Thr Gly Arg Leu Asp
         85                  90                  95 ttc atc aga tgg gtg aat gat gct tca gat tct ttt gaa act gct gct        393
Phe Ile Arg Trp Val Asn Asp Ala Ser Asp Ser Phe Glu Thr Ala Ala
     100                 105                 110 att cag aat ggt atg tac att gcg gtc att gga agc ctc aag gga ctg        441
Ile Gln Asn Gly Met Tyr Ile Ala Val Ile Gly Ser Leu Lys Gly Leu
 115                 120                 125 caa gag agg aag cgt gct act gct ttc tca atc agg cct ata acc gat        489
Gln Glu Arg Lys Arg Ala Thr Ala Phe Ser Ile Arg Pro Ile Thr Asp
130                 135                 140                 145 ttc aat gag gtt acg ctg cat ttc att cag tgt gtt cgg atg cat ata        537
Phe Asn Glu Val Thr Leu His Phe Ile Gln Cys Val Arg Met His Ile
             150                 155                 160 gag aac act gaa tta aag gct ggc agt cct gca cga atc aat tct tct        585
Glu Asn Thr Glu Leu Lys Ala Gly Ser Pro Ala Arg Ile Asn Ser Ser
         165                 170                 175 atg gga gtg tca ttc tca aat gga ttc agt gaa tca agc aca ccg aca        633
Met Gly Val Ser Phe Ser Asn Gly Phe Ser Glu Ser Ser Thr Pro Thr
     180                 185                 190 tct ttg aaa tcc agt ccc gca ccg gtg acc agc ggg tca tcc gat act        681
Ser Leu Lys Ser Ser Pro Ala Pro Val Thr Ser Gly Ser Ser Asp Thr
 195                 200                 205 gat ctg cac acg cag gtc ctg aat ttt ttt aat gaa cca gcg aac ctc        729
Asp Leu His Thr Gln Val Leu Asn Phe Phe Asn Glu Pro Ala Asn Leu
210                 215                 220                 225 gag agt gag cat ggg gtg cac gtt gat gaa gta ctc aag cgg ttc aaa        777
Glu Ser Glu His Gly Val His Val Asp Glu Val Leu Lys Arg Phe Lys
             230                 235                 240 ctt ttg ccg aag aag cag atc acg gat gct att gat tac aat atg gac        825
Leu Leu Pro Lys Lys Gln Ile Thr Asp Ala Ile Asp Tyr Asn Met Asp
         245                 250                 255 tcg ggg cgt ctt tac tca aca att gat gaa ttc cac tac aag gca act        873
Ser Gly Arg Leu Tyr Ser Thr Ile Asp Glu Phe His Tyr Lys Ala Thr
     260                 265                 270 taaccgattt gaaggtcagc ctgctggaaa tggcagagga ctaagtatca cttgtactaa     933
```

```
accaaagtct ggaaatgtca tgttgtgtca tgaaatgcat ggttggttta tggaaacatt      993
tatatcttgt atcaactagt tgatttgtat ctcttgtgtc aacttaatga ctgagccaac     1053
aaaaggaaaa aaaaaaaaaa a                                               1074
```

<210> SEQ ID NO 20
<211> LENGTH: 273
<212> TYPE: PRT
<213> ORGANISM: Zea mays

<400> SEQUENCE: 20

```
Met Met Pro Leu Ser Gln Thr Asp Phe Ser Pro Ser Gln Phe Thr Ser
 1               5                  10                  15

Ser Gln Asn Ala Ala Asp Ser Thr Thr Pro Ser Lys Met Arg Gly
            20                  25                  30

Ala Ser Ser Thr Met Pro Leu Thr Val Lys Gln Val Val Asp Ala Gln
        35                  40                  45

Gln Ser Gly Thr Gly Glu Lys Gly Ala Pro Phe Ile Val Asn Gly Val
    50                  55                  60

Glu Met Ala Asn Ile Arg Leu Val Gly Met Val Asn Ala Lys Val Glu
65                  70                  75                  80

Arg Thr Thr Asp Val Thr Phe Thr Leu Asp Asp Gly Thr Gly Arg Leu
                85                  90                  95

Asp Phe Ile Arg Trp Val Asn Asp Ala Ser Asp Ser Phe Glu Thr Ala
            100                 105                 110

Ala Ile Gln Asn Gly Met Tyr Ile Ala Val Ile Gly Ser Leu Lys Gly
        115                 120                 125

Leu Gln Glu Arg Lys Arg Ala Thr Ala Phe Ser Ile Arg Pro Ile Thr
    130                 135                 140

Asp Phe Asn Glu Val Thr Leu His Phe Ile Gln Cys Val Arg Met His
145                 150                 155                 160

Ile Glu Asn Thr Glu Leu Lys Ala Gly Ser Pro Ala Arg Ile Asn Ser
                165                 170                 175

Ser Met Gly Val Ser Phe Ser Asn Gly Phe Ser Glu Ser Ser Thr Pro
            180                 185                 190

Thr Ser Leu Lys Ser Ser Pro Ala Pro Val Thr Ser Gly Ser Ser Asp
        195                 200                 205

Thr Asp Leu His Thr Gln Val Leu Asn Phe Asn Glu Pro Ala Asn
    210                 215                 220

Leu Glu Ser Glu His Gly Val His Val Asp Glu Val Leu Lys Arg Phe
225                 230                 235                 240

Lys Leu Leu Pro Lys Lys Gln Ile Thr Asp Ala Ile Asp Tyr Asn Met
                245                 250                 255

Asp Ser Gly Arg Leu Tyr Ser Thr Ile Asp Glu Phe His Tyr Lys Ala
            260                 265                 270
Thr
```

<210> SEQ ID NO 21
<211> LENGTH: 1231
<212> TYPE: DNA
<213> ORGANISM: Zea mays
<220> FEATURE:
<221> NAME/KEY: misc_feature
<222> LOCATION: (0)...(0)
<223> OTHER INFORMATION: Maize RPA Middle Subunit Homologue-7
<220> FEATURE:
<221> NAME/KEY: CDS
<222> LOCATION: (85)...(903)

-continued

```
<400> SEQUENCE: 21
tcccgggtcg acccacgcgt ccgcgatcct cccatctgcg cacccgcaag cctattcgcc          60
gcacctcctc aggtgaccgg gaag atg atg ccg ttg agc caa acc gac ttc           111
                            Met Met Pro Leu Ser Gln Thr Asp Phe
                              1               5 tcg ccg tcg cag ttc acc tcc tcc cag aat gcc gcc gcc gac tcc acc          159
Ser Pro Ser Gln Phe Thr Ser Ser Gln Asn Ala Ala Ala Asp Ser Thr
 10              15                  20                  25 acg cct tcc aag atg cgc ggc gcg tcc agc acc atg ccg ctc acc gtg          207
Thr Pro Ser Lys Met Arg Gly Ala Ser Ser Thr Met Pro Leu Thr Val
             30                  35                  40 aag cag gtc gtc gac gcg cag cag tct ggc acg ggc gag aag ggc gct          255
Lys Gln Val Val Asp Ala Gln Gln Ser Gly Thr Gly Glu Lys Gly Ala
             45                  50                  55 ccg ttc atc gtc aat ggc gtc gag atg gct aac att cga ctt gtg ggg          303
Pro Phe Ile Val Asn Gly Val Glu Met Ala Asn Ile Arg Leu Val Gly
             60                  65                  70 atg gtc aat gcc aag gtg gag cgg acg acc gat gtg acc ttc acg ctc          351
Met Val Asn Ala Lys Val Glu Arg Thr Thr Asp Val Thr Phe Thr Leu
 75              80                  85 gac gat ggc acc ggc cgc ctc gat ttc atc aga tgg gtg aat gat gct          399
Asp Asp Gly Thr Gly Arg Leu Asp Phe Ile Arg Trp Val Asn Asp Ala
 90                  95                 100                 105 tca gat tct ttt gaa act gct gct att cag aat ggt atg tac att gcg          447
Ser Asp Ser Phe Glu Thr Ala Ala Ile Gln Asn Gly Met Tyr Ile Ala
                    110                 115                 120 gtc att gga agc ctc aag gga ctg caa gag agg aag cgt gct act gct          495
Val Ile Gly Ser Leu Lys Gly Leu Gln Glu Arg Lys Arg Ala Thr Ala
                125                 130                 135 ttc tca atc agg cct ata acc gat ttc aat gag gtt acg ctg cat ttc          543
Phe Ser Ile Arg Pro Ile Thr Asp Phe Asn Glu Val Thr Leu His Phe
                140                 145                 150 att cag tgt gtt cgg atg cat ata gag aac act gaa tta aag gct ggc          591
Ile Gln Cys Val Arg Met His Ile Glu Asn Thr Glu Leu Lys Ala Gly
                155                 160                 165 agt cct gca cga atc aat tct tct atg gga gtg tca ttc tca aat gga          639
Ser Pro Ala Arg Ile Asn Ser Ser Met Gly Val Ser Phe Ser Asn Gly
170                 175                 180                 185 ttc agt gaa tca agc aca ccg aca tct ttg aaa tcc agt ccc gca ccg          687
Phe Ser Glu Ser Ser Thr Pro Thr Ser Leu Lys Ser Ser Pro Ala Pro
                    190                 195                 200 gtg acc agc ggg tca tcc gat act gat ctg cac acg cag gtc ctg aat          735
Val Thr Ser Gly Ser Ser Asp Thr Asp Leu His Thr Gln Val Leu Asn
                205                 210                 215 ttt ttt aat gaa cca gcg aac ctc gag agt gag cat ggg gtg cac gtt          783
Phe Phe Asn Glu Pro Ala Asn Leu Glu Ser Glu His Gly Val His Val
                220                 225                 230 gat gaa gta ctc aag cgg ttc aaa ctt ttg ccg aag aag cag atc acg          831
Asp Glu Val Leu Lys Arg Phe Lys Leu Leu Pro Lys Lys Gln Ile Thr
235                 240                 245 gat gct att gat tac aat atg gac tcg ggc cgt ctt tac tca aca att          879
Asp Ala Ile Asp Tyr Asn Met Asp Ser Gly Arg Leu Tyr Ser Thr Ile
250                 255                 260                 265 gat gaa ttc cac tac aag gca act taaccgattt gaaggtcagc ctgctggaaa         933
Asp Glu Phe His Tyr Lys Ala Thr
                    270 tggcagagga ctaagtatca cttgtactaa accaaagtct ggaaatgtca tgttgtgtca         993 tgaaatgcat ggttggttta tggaaacatt tatatcttgt atcaactagt tgatttgtat        1053
```

-continued

```
ctcttgtgtc aacttaatga ctgagccaac aaaaggaaga tgtagaggca gacagacatt    1113
tgtagattgg ctgatagctg attcgggtag ctggtccaat tgcaatctgg ggcccaataa    1173
ttcagatgca aaagcagaaa gatatttcaa aaaaaaaaaa aaaaaaaaaa aaaaaaa       1231

<210> SEQ ID NO 22
<211> LENGTH: 273
<212> TYPE: PRT
<213> ORGANISM: Zea mays

<400> SEQUENCE: 22

Met Met Pro Leu Ser Gln Thr Asp Phe Ser Pro Ser Gln Phe Thr Ser
 1               5                  10                  15

Ser Gln Asn Ala Ala Asp Ser Thr Thr Pro Ser Lys Met Arg Gly
             20                  25                  30

Ala Ser Ser Thr Met Pro Leu Thr Val Lys Gln Val Val Asp Ala Gln
             35                  40                  45

Gln Ser Gly Thr Gly Glu Lys Gly Ala Pro Phe Ile Val Asn Gly Val
         50                  55                  60

Glu Met Ala Asn Ile Arg Leu Val Gly Met Val Asn Ala Lys Val Glu
 65                  70                  75                  80

Arg Thr Thr Asp Val Thr Phe Thr Leu Asp Asp Gly Thr Gly Arg Leu
                 85                  90                  95

Asp Phe Ile Arg Trp Val Asn Asp Ala Ser Asp Ser Phe Glu Thr Ala
                100                 105                 110

Ala Ile Gln Asn Gly Met Tyr Ile Ala Val Ile Gly Ser Leu Lys Gly
            115                 120                 125

Leu Gln Glu Arg Lys Arg Ala Thr Ala Phe Ser Ile Arg Pro Ile Thr
    130                 135                 140

Asp Phe Asn Glu Val Thr Leu His Phe Ile Gln Cys Val Arg Met His
145                 150                 155                 160

Ile Glu Asn Thr Glu Leu Lys Ala Gly Ser Pro Ala Arg Ile Asn Ser
                165                 170                 175

Ser Met Gly Val Ser Phe Ser Asn Gly Phe Ser Glu Ser Ser Thr Pro
            180                 185                 190

Thr Ser Leu Lys Ser Ser Pro Ala Pro Val Thr Ser Gly Ser Ser Asp
        195                 200                 205

Thr Asp Leu His Thr Gln Val Leu Asn Phe Phe Asn Glu Pro Ala Asn
    210                 215                 220

Leu Glu Ser Glu His Gly Val His Val Asp Glu Val Leu Lys Arg Phe
225                 230                 235                 240

Lys Leu Leu Pro Lys Lys Gln Ile Thr Asp Ala Ile Asp Tyr Asn Met
                245                 250                 255

Asp Ser Gly Arg Leu Tyr Ser Thr Ile Asp Glu Phe His Tyr Lys Ala
            260                 265                 270

Thr
```